(12) United States Patent
Kapeller-Libermann et al.

(10) Patent No.: US 6,730,491 B2
(45) Date of Patent: May 4, 2004

(54) 2504, 15977, AND 14760, NOVEL PROTEIN KINASE FAMILY MEMBERS AND USES THEREFOR

(75) Inventors: Rosana Kapeller-Libermann, Chestnut Hill, MA (US); Rachel A. Meyers, Newton, MA (US); Rory A. J. Curtis, Southborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/797,039

(22) Filed: Feb. 28, 2001

(65) Prior Publication Data

US 2002/0042099 A1 Apr. 11, 2002

Related U.S. Application Data

(60) Provisional application No. 60/186,061, filed on Feb. 29, 2000.

(51) Int. Cl.[7] .............................. C12Q 1/48; C12Q 1/68; C12N 15/00; C12N 5/00; C12N 9/12
(52) U.S. Cl. .............................. 435/15; 435/194; 435/6; 435/320.1; 435/325; 435/252.3
(58) Field of Search .......................... 435/194, 6, 252.3, 435/320.1, 325, 15

(56) References Cited

U.S. PATENT DOCUMENTS

| | | | | |
|---|---|---|---|---|
| 5,686,412 A | * | 11/1997 | Hoekstra et al. | 514/12 |
| 6,331,424 B1 | * | 12/2001 | Beraud et al. | 435/196 |

FOREIGN PATENT DOCUMENTS

| | | |
|---|---|---|
| EP | 1 130 094 A2 | 9/2001 |
| WO | 99/27080 | 6/1999 |
| WO | 00/55177 | 9/2000 |
| WO | 00/58473 | 10/2000 |
| WO | 01/12659 A2 | 2/2001 |
| WO | 01/20004 A2 | 3/2001 |
| WO | WO 01/29228 A1 | 4/2001 |
| WO | WO 01/53493 A2 | 7/2001 |
| WO | 01/81555 A2 | 11/2001 |

OTHER PUBLICATIONS

ATCC catalogue of Cell Lines and Hybridomas, 7th edition, 1992, pp. 4–5.*
Zhai et al., J.B.C., 270(21), pp. 12717–12724, 1995.*
GenBank Accession No. L22557, Nov. 21, 1993.
GenBank Accession No. AU079481, Oct. 19, 1999.
GenBank Accession No. Q9YGM4, May 1, 1999.
GenBank Accession No. AX086278, Mar. 9, 2001.
GenBank Accession No. AX086279, Mar. 6, 2001.
GenBank Accession No. AX086280, Mar. 6, 2001.
GenBank Accession No. AX086281, Mar. 6, 2001.
GenBank Accession No. AAM93379, Nov. 6, 2001.
GenBank Accession No. AAM93404, Nov. 6, 2001.
GenBank Accession No. AAM93679, Nov. 6, 2001.
Birchmeier et al., "Tyrosine Kinase Receptors in . . . ," BioEssays 15(3):185–190, 1993.
D'Urso et al., "Cell Cycle Control of DNA . . . ," Science, 250:786–790, 1990.
GenBank Accession No. AA197072, Mar. 12, 1998.
GenBank Accession No. R02824, Mar. 31, 1995.
GenBank Accession No. A28798, Dec. 19, 1997.
GenBank Accession No. P20689, Jul. 15, 1998.
GenBank Accession No. AAA41625, Apr. 27, 1993.
GenBank Accession No. AAA31400, Apr. 27, 1993.
GenBank Accession No. AAA73168, Sep. 27, 1993.
GenBank Accession No. AI939489, Dec. 13, 1999.
GenBank Accession No. AW173082, Nov. 16, 1999.
GenBank Accession No. AL137522, Feb. 18, 2000.
GenBank Accession No. Q62761, Jul. 15, 1999.
GenBank Accession No. Q62763, Jul. 15, 1999.
GenBank Accession No. L22557, Mar. 10, 1994.
GenBank Accession No. AAA16633, Mar. 10, 1994.
GenBank Accession No. CAA09101, Feb. 24, 1999.

* cited by examiner

Primary Examiner—Maryam Monshipouri
(74) Attorney, Agent, or Firm—Millennium Pharmaceuticals, Inc.

(57) ABSTRACT

The invention provides isolated nucleic acids molecules, designated 2504, 15977, or 14760 nucleic acid molecules, which encode novel protein kinase family members. The invention also provides antisense nucleic acid molecules, recombinant expression vectors containing 2504, 15977, or 14760 nucleic acid molecules, host cells into which the expression vectors have been introduced, and nonhuman transgenic animals in which a 2504, 15977, or 14760 gene has been introduced or disrupted. The invention still further provides isolated 2504, 15977, or 14760 proteins, fusion proteins, antigenic peptides and anti-2504, 15977, or 14760 antibodies. Diagnostic methods utilizing compositions of the invention are also provided.

6 Claims, 18 Drawing Sheets

BEGIN SEQ ID NO:1

CACGCGTCCGCGAAGCGGCTGCATCTGGCGCCGCGTCTGCCCCGCGTGCTCGGAGCGGATTCTGCCCGCCGTCCCCGGA

BEGIN SEQ ID NO:2

BEGIN SEQ ID NO:3 M  1

GCCCTCGGCGCCCCGCTGAGCCCGCGATCACTTCCTCCCTGTGACCAACCGGCGCTGCAGGTTAGAGCCTGGCA ATG  3

```
     F   F   G   C   V   T   L   G   D   K   K   N   Y   N   Q   P   S   E   V   T    21
    CCG TTT GGG TGT GTG ACT CTG GGC GAC AAG AAG AAC TAT AAC CAG CCA TCG GAG GTG ACT    63

D   R   Y   D   L   G   Q   V   I   K   T   E   E   F   C   E   I   F   R   A    41
    GAC AGA TAT GAT TTG GGA CAG GTC ATC AAG ACT GAG GAG TTT TGT GAA ATC TTC CGG GCC   123

K   D   K   T   T   G   K   L   H   T   C   K   K   F   Q   K   R   D   G   R    61
    AAG GAC AAG ACG ACA GGC AAG CTG CAC ACC TGC AAG AAG TTC CAG AAG CGG GAC GGC CGC   183

K   V   R   K   A   A   K   N   E   I   G   I   L   K   M   V   K   H   P   N    81
    AAG GTG CGG AAA GCT GCC AAG AAC GAG ATA GGC ATC CTC AAG ATG GTG AAG CAT CCC AAC   243

I   L   Q   L   V   D   V   F   V   T   R   K   E   Y   F   I   F   L   E   L   101
    ATC CTA CAG CTG GTG GAT GTG TTT GTG ACC CGC AAG GAG TAC TTT ATC TTC CTG GAG CTG   303

A   T   G   R   E   V   F   D   W   I   L   D   Q   G   Y   Y   S   E   R   D   121
    GCC ACG GGG AGG GAG GTG TTT GAC TGG ATC CTG GAC CAG GGC TAC TAC TCG GAG CGA GAC   363

T   S   N   V   V   R   Q   V   L   E   A   V   A   Y   L   H   S   L   K   I   141
    ACA AGC AAC GTG GTA CGG CAA GTC CTG GAG GCC GTG GCC TAT TTG CAC TCA CTC AAG ATC   423

V   H   R   N   L   K   L   E   N   L   V   Y   Y   N   R   L   K   N   S   K   161
    GTG CAC AGG AAT CTC AAG CTG GAG AAC CTG GTT TAC TAC AAC CGG CTG AAG AAC TCG AAG   483

I   V   I   S   D   F   H   L   A   K   L   E   N   G   L   I   K   E   P   C   181
    ATT GTC ATC AGT GAC TTC CAT CTG GCT AAG CTA GAA AAT GGC CTC ATC AAG GAG CCC TGT   543

G   T   P   E   Y   L   A   P   E   V   V   G   R   Q   R   Y   G   R   P   V   201
    GGG ACC CCC GAG TAT CTG GCC CCA GAG GTG GTA GGC CGG CAG CGG TAT GGA CGC CCT GTG   603

D   C   W   A   I   G   V   I   M   Y   I   L   L   S   G   N   P   P   F   Y   221
    GAC TGC TGG GCC ATT GGA GTC ATC ATG TAC ATC CTG CTT TCA GGC AAT CCA CCT TTC TAT   663

E   E   V   E   E   D   D   Y   E   N   H   D   K   N   L   F   R   K   I   L   241
    GAG GAG GTG GAA GAA GAT GAT TAT GAG AAC CAT GAT AAG AAT CTC TTC CGC AAG ATC CTG   723

A   G   D   Y   E   F   D   S   P   Y   W   D   D   I   S   Q   A   A   K   D   261
    GCT GGT GAC TAT GAG TTT GAC TCT CCA TAT TGG GAT GAT ATT TCG CAG GCA GCC AAA GAC   783
```

Fig. 1A

| | | | | | | | | | | | | | | | | | | | | |
|---|---|---|---|---|---|---|---|---|---|---|---|---|---|---|---|---|---|---|---|---|
|L|V|T|R|L|M|E|V|E|Q|D|Q|R|I|T|A|E|E|A|I|281|
|CTG|GTC|ACA|AGG|CTG|ATG|GAG|GTG|GAG|CAA|GAC|CAG|CGG|ATC|ACT|GCA|GAA|GAG|GCC|ATC|843|
|S|H|E|W|I|S|G|N|A|A|S|D|K|N|I|K|D|G|V|C|301|
|TCC|CAT|GAG|TGG|ATT|TCT|GGC|AAT|GCT|GCT|TCT|GAT|AAG|AAC|ATC|AAG|GAT|GGT|GTC|TGT|903|
|A|Q|I|E|K|N|F|A|R|A|K|W|K|K|A|V|R|V|T|T|321|
|GCC|CAG|ATT|GAA|AAG|AAC|TTT|GCC|AGG|GCC|AAG|TGG|AAG|AAG|GCT|GTC|CGA|GTG|ACC|ACC|963|
|L|M|K|R|L|R|A|P|E|Q|S|S|T|A|A|A|Q|S|A|S|341|
|CTC|ATG|AAA|CGG|CTC|CGG|GCA|CCA|GAG|CAG|TCC|AGC|ACG|GCT|GCA|GCC|CAG|TCG|GCC|TCA|1023|
|A|T|D|T|A|T|P|G|A|A|G|G|A|T|A|A|A|A|S|G|361|
|GCC|ACA|GAC|ACT|GCC|ACC|CCC|GGG|GCT|GCA|GGT|GGG|GCC|ACA|GCT|GCA|GCT|GCG|AGT|GGA|1083|
|A|T|S|A|P|E|G|D|A|A|R|A|A|K|S|D|N|V|A|P|381|
|GCT|ACC|TCA|GCC|CCT|GAG|GGT|GAT|GCT|GCT|CGT|GCT|GCA|AAG|AGT|GAT|AAT|GTG|GCC|CCC|1143|
|A|D|R|S|A|T|P|A|T|D|G|S|A|T|P|A|T|D|G|S|401|
|GCA|GAC|CGT|AGT|GCC|ACC|CCA|GCC|ACA|GAT|GGA|AGT|GCC|ACC|CCA|GCC|ACT|GAT|GGC|AGT|1203|
|V|T|P|A|T|D|G|S|I|T|P|A|T|D|G|S|V|T|P|A|421|
|GTC|ACC|CCA|GCC|ACC|GAT|GGA|AGC|ATC|ACT|CCA|GCC|ACT|GAT|GGG|AGT|GTC|ACC|CCA|GCC|1263|
|T|D|R|S|A|T|P|A|T|D|G|R|A|T|P|A|T|E|E|S|441|
|ACT|GAC|AGG|AGC|GCT|ACT|CCA|GCC|ACT|GAT|GGG|AGA|GCC|ACA|CCA|GCC|ACA|GAA|GAG|AGC|1323|
|T|V|P|T|T|Q|S|S|A|M|L|A|T|K|A|A|A|T|P|E|461|
|ACT|GTG|CCC|ACC|ACC|CAA|AGC|AGT|GCC|ATG|CTG|GCC|ACC|AAG|GCA|GCT|GCC|ACC|CCT|GAG|1383|
|P|A|M|A|Q|P|D|S|T|A|P|E|G|A|T|G|Q|A|P|P|481|
|CCG|GCT|ATG|GCC|CAG|CCG|GAC|AGC|ACA|GCC|CCA|GAG|GGC|GCC|ACA|GGC|CAG|GCT|CCA|CCC|1443|

END SEQ ID NO:2

| | | | | | | | | | | | | | | | | | | | | |
|---|---|---|---|---|---|---|---|---|---|---|---|---|---|---|---|---|---|---|---|---|
|S|S|K|G|E|E|A|A|G|Y|A|Q|E|S|Q|R|E|E|A|S|501|
|TCT|AGT|AAA|GGG|GAA|GAG|GCT|GCT|GGT|TAT|GCC|CAG|GAG|TCT|CAA|AGG|GAG|GAG|GCC|AGC|1503|
|*| | | | | | | | | | | | | | | | | | | |502|
|TGA| | | | | | | | | | | | | | | | | | | |1506|

END SEQ ID NO:3

GTAGGCAGCCTGGTGAGGGGGGGCAGGGGATGGGCAGGAGGGTGGGAGAGTGGATGAGGGGCTTCTCACTGTACATAGA

GTCACTGGCATGATGCCCTCGCTCCCCCATGCCCCCACATCCCAGTGGGGCATAACTAGGGGTCACGGGAGAGCAGTCT

CGTCTCCTGTGTGTATGTGTGTGAGTGGTGGGCAGGCCAGTGGCAGGGCCGGCCCCAGCCCCTGCATGGATTCCTTGTG

GCTTTTCTGTCTTTTGCTAGCTTCACCAGTTTCTGTTCCTTGTGGGATGCTGCTCTAGGGATACTCAGGGGGCTCCTGC

TCTCCTTCCCCTTCCCTTCTTGCCTCACCATTCCCCTAGGCAGGCCCTGCAGGTCCCACACTCTCCCAGGCCCTAAACT

TGGGCGGCCTTGCCCTGAGAGCTGGTCCTCCAGCGAGGCCCTGTCAGCGGTCTTAGGCTCCTGCACATGAAGGTGTGTG

CCTGTGGTGTGTGGGCTGCTCTAGGAGCAGATACAGGCTGGTATAGAGGATGCAGAAAGGTAGGGCAGTATGTTTAAGT

CCAGACTTGGCACATGGCTAGGGATACTGCTCACTAGCTGTGGAGGTCCTCAGGAGTGGAGAGAATGAGTAGGANGGCA

GAANCT

END SEQ ID NO:1

Fig. 1B

Alignments of top-scoring domains:
pkinase: domain 1 of 1, from 37 to 286: score 229.1, E = 6.5e-65
```
   SEQ ID NO:10   *->kVykakhk.tgkivAvKilk.kesls.....lrEiqilkrlsHpNIv
                     ++++ak+k+tgk+   K++ +++  + ++    +Ei ilk+++HpNI+
         2504   37  EIFRAKDKtTGKLHTCKKFQkRDGRKvrkaaKNEIGILKMVKHPNIL  83 rllgvfedtddhlylvmEymegGdLfdylrrngplsekeakkialQilrG
                     +l +vf  t +++ + +E++ g + fd++ ++g++se++  ++++Q+l++
         2504   84  QLVDVFV-TRKEYFIFLELATGREVFDWILDQGYYSERDTSNVVRQVLEA 132 lEYLHsngivHRDLKpeNILlden...gtvKiaDFGLArll.ekltttfvG
                     ++YLHs +ivHR LK eN+    ++ ++ ++ i+DF LA+l ++   +G
         2504  133  VAYLHSLKIVHRNLKLENLVYYNRlknSKIVISDFHLAKLEnGLIKEPCG 182

TpwYmmAPEvilegrgysskvDvWSlGviLyElltggplfpgadlpaftg
                     Tp+Y  APEv + ++ y+++vD W++Gvi+y  ll+g
         2504  183  TPEYL-APEV-VGRQRYGRPVDCWAIGVIMYILLSG------------- 216 gdevdqliifvlklPfsdelp.ktridpleelfrikkr.....rlplpsn
                                   +Pf++e++++  ++  ++lfr ++ ++ +  +p ++
         2504  217  -----------NPPFYEEVEeDDYENHDKNLFRKILAgdyefDSPYWDD 254 cSeelkdLlkkcLnkDPskRpGsatakeilnhpwf<-*
                     +S ++kdL++++ ++    +R+  ta+e++ h w+
         2504  255  ISQAAKDLVTRLMEVEQDQRI---TAEEAISHEWI      286
```

Fig. 3A

Alignments of top-scoring domains:
serkin_6: domain 1 of 1, from 24 to 286: score 284.1, E= 1.8e-81
```
   SEQ ID NO:11   *->YellkklGkGaFGkVylardkktgrlvAiKvik........erilrE
                     Y+l++++    F + ++a+dk tg+l  +K+   ++++++ ++ +++E
         2504   24  YDLGQVIKTEEFCEIFRAKDKTTGKLHTCKKFQkrdgrkvrKAAKNE  70 ikiLkk.dHPNIVkLydvfed.dklylVmEyceGdlGdLfdllkkrgrrg
                     i iLk+ +HPNI +L dvf++++++++++++E++ G    ++fd + ++g+
         2504   71  IGILKMvKHPNILQLVDVFVTrKEYFIFLELATG--REVFDWILDQGY-- 116 lrkvlsE.earfyfrQilsaLeYLHsqgIiHRDLKpeNiLLds.....hv
                     +sE+++   ++rQ+l+a++YLHs++I+HR LK eN+    ++ +++ +
         2504  117  ----YSErDTSNVVRQVLEAVAYLHSLKIVHRNLKLENLVYYNrlknsKI 162

KlaDFGlArql....ttfvGTpeYmAPEvl...gYgkpavDiWSlGcily
                     ++DF lA++ ++    + +GTpeY+APEv++++ Yg+ +vD W++G+i+y
         2504  163  VISDFHLAKLEngliKEPCGTPEYLAPEVVgrqRYGR-PVDCWAIGVIMY 211

ElltGkpPFp.........qldlifkkig............Speakd
                     +ll+G pPF+++ ++++ +++++ +f+ki+ ++++ +++++++ S+ akd
         2504  212  ILLSGNPPFYeeveeddyenHDKNLFRKILagdyefdspywddiSQAAKD 261

LikklLvkdPekRlta.eaLedeldikaHPff<-*
                     L+ +l++++ ++R+ta+ea       H+++
         2504  262  LVTRLMEVEQDQRITAeEAIS-------HEWI   286
```

Fig. 3B

BEGIN SEQ ID NO:4

GGGAGCGCCCCGCGTCCGGGACAAGCCGCAGACAAAACCCCTCAGACACCAAAGGGCTTTATTCGGCCGGGAGCATCAG

CAAACTTAGGTCTCAAAAAACCAAGCTCTCCAAGTTACAAGATGTTCACCTAAGATTGAGACCTAGTGACTACGTTTCC

TACGGGAACAAATAAATGGTTTTTCATCTCCCGGAGATACATTACAAACAAATATGGTGCTAAAAGAACTCCTTACCTT

TCTCTGACTACAATTTATTTGGACATACTTTTGTATTGAAGAGAGGTATACATACTGAAGCTACTTGCTGTACTATAGG
BEGIN SEQ ID NO:5
BEGIN SEQ ID NO:6

|  |  |  |  |  |  |  |  |  | M | D | H | P | S | R | E | K | D | E | R | Q | R | T | 14 |
|---|---|---|---|---|---|---|---|---|---|---|---|---|---|---|---|---|---|---|---|---|---|---|---|
| AGACTCTGTCCTGTAGGATC | | | | | | | | | ATG | GAC | CAT | CCT | AGT | AGG | GAA | AAG | GAT | GAA | AGA | CAA | CGG | ACG | 42 |

| T | K | P | M | A | Q | R | S | A | H | C | S | R | P | S | G | S | S | S | S | 34 |
|---|---|---|---|---|---|---|---|---|---|---|---|---|---|---|---|---|---|---|---|---|
| ACT | AAA | CCC | ATG | GCA | CAA | AGG | AGT | GCA | CAC | TGC | TCT | CGA | CCA | TCT | GGC | TCC | TCA | TCG | TCC | 102 |

| S | G | V | L | M | V | G | P | N | F | R | V | G | K | K | I | G | C | G | N | 54 |
|---|---|---|---|---|---|---|---|---|---|---|---|---|---|---|---|---|---|---|---|---|
| TCT | GGG | GTT | CTT | ATG | GTG | GGA | CCC | AAC | TTC | AGG | GTT | GGC | AAG | AAG | ATA | GGA | TGT | GGG | AAC | 162 |

| F | G | E | L | R | L | G | K | N | L | Y | T | N | E | Y | V | A | I | K | L | 74 |
|---|---|---|---|---|---|---|---|---|---|---|---|---|---|---|---|---|---|---|---|---|
| TTC | GGA | GAG | CTC | AGA | TTA | GGT | AAA | AAT | CTC | TAC | ACC | AAT | GAA | TAT | GTA | GCA | ATC | AAA | CTG | 222 |

| E | P | I | K | S | R | A | P | Q | L | H | L | E | Y | R | F | Y | K | Q | L | 94 |
|---|---|---|---|---|---|---|---|---|---|---|---|---|---|---|---|---|---|---|---|---|
| GAA | CCA | ATA | AAA | TCA | CGT | GCT | CCA | CAG | CTT | CAT | TTA | GAG | TAC | AGA | TTT | TAT | AAA | CAG | CTT | 282 |

| G | S | A | G | E | G | L | P | Q | V | Y | Y | F | G | P | C | G | K | Y | N | 114 |
|---|---|---|---|---|---|---|---|---|---|---|---|---|---|---|---|---|---|---|---|---|
| GGC | AGT | GCA | GGT | GAA | GGT | CTC | CCA | CAG | GTG | TAT | TAC | TTT | GGA | CCA | TGT | GGG | AAA | TAT | AAT | 342 |

| A | M | V | L | E | L | L | G | P | S | L | E | D | L | F | D | L | C | D | R | 134 |
|---|---|---|---|---|---|---|---|---|---|---|---|---|---|---|---|---|---|---|---|---|
| GCC | ATG | GTG | CTG | GAG | CTC | CTT | GGC | CCT | AGC | TTG | GAG | GAC | TTG | TTT | GAC | CTC | TGT | GAC | CGA | 402 |

| T | F | T | L | K | T | V | L | M | I | A | I | Q | L | L | S | R | M | E | Y | 154 |
|---|---|---|---|---|---|---|---|---|---|---|---|---|---|---|---|---|---|---|---|---|
| ACA | TTT | ACT | TTG | AAG | ACG | GTG | TTA | ATG | ATA | GCC | ATC | CAG | CTG | CTT | TCT | CGA | ATG | GAA | TAC | 462 |

| V | H | S | K | N | L | I | Y | R | D | V | K | P | E | N | F | L | I | G | R | 174 |
|---|---|---|---|---|---|---|---|---|---|---|---|---|---|---|---|---|---|---|---|---|
| GTG | CAC | TCA | AAG | AAC | CTC | ATT | TAC | CGA | GAT | GTC | AAG | CCA | GAG | AAC | TTC | CTG | ATT | GGT | CGA | 522 |

| Q | G | N | K | K | E | H | V | I | H | I | I | D | F | G | L | A | K | E | Y | 194 |
|---|---|---|---|---|---|---|---|---|---|---|---|---|---|---|---|---|---|---|---|---|
| CAA | GGC | AAT | AAG | AAA | GAG | CAT | GTT | ATA | CAC | ATT | ATA | GAC | TTT | GGA | CTG | GCC | AAG | GAA | TAC | 582 |

| I | D | P | E | T | K | K | H | I | P | Y | R | E | H | K | S | L | T | G | T | 214 |
|---|---|---|---|---|---|---|---|---|---|---|---|---|---|---|---|---|---|---|---|---|
| ATT | GAC | CCC | GAA | ACC | AAA | AAA | CAC | ATA | CCT | TAT | AGG | GAA | CAC | AAA | AGT | TTA | ACT | GGA | ACT | 642 |

| A | R | Y | M | S | I | N | T | H | L | G | K | E | Q | S | R | R | D | D | L | 234 |
|---|---|---|---|---|---|---|---|---|---|---|---|---|---|---|---|---|---|---|---|---|
| GCG | AGA | TAT | ATG | TCT | ATC | AAC | ACG | CAT | CTT | GGC | AAA | GAG | CAA | AGC | CGG | AGA | GAT | GAT | TTG | 702 |

Fig. 4A

```
    E   A   L   G   H   M   F   M   Y   F   L   R   G   S   L   P   W   Q   G   L   254
   GAA GCC CTA GGC CAT ATG TTC ATG TAT TTC CTT CGA GGC AGC CTC CCC TGG CAA GGA CTC  762

K   A   D   T   L   K   E   R   Y   Q   K   I   G   D   T   K   R   N   T   P   274
   AAG GCT GAC ACA TTA AAA GAG AGA TAT CAA AAA ATT GGT GAC ACC AAA AGG AAT ACT CCC  822

I   E   A   L   C   E   N   F   P   E   E   M   A   T   Y   L   R   Y   V   R   294
   ATT GAA GCT CTC TGT GAG AAC TTT CCA GAG GAG ATG GCA ACC TAC CTT CGA TAT GTC AGG  882

R   L   D   F   F   E   K   P   D   Y   E   Y   L   R   T   L   F   T   D   L   314
   CGA CTG GAC TTC TTT GAA AAA CCT GAT TAT GAG TAT TTA CGG ACC CTC TTC ACA GAC CTC  942

F   E   K   K   G   Y   T   F   D   Y   A   Y   D   W   V   G   R   P   I   P   334
   TTT GAA AAG AAA GGC TAC ACC TTT GAC TAT GCC TAT GAT TGG GTT GGG AGA CCT ATT CCT 1002

T   P   V   G   S   V   H   V   D   S   G   A   S   A   I   T   R   E   S   H   354
   ACT CCA GTA GGG TCA GTT CAC GTA GAT TCT GGT GCA TCT GCA ATA ACT CGA GAA AGC CAC 1062

T   H   R   D   R   P   S   Q   Q   Q   P   L   R   N   Q   N   V   S   S   E   374
   ACA CAT AGG GAT CGG CCA TCA CAA CAG CAG CCT CTT CGA AAT CAG AAT GTA TCA TCA GAG 1122

R   R   G   E   W   E   I   Q   P   S   R   Q   T   N   T   S   Y   L   T   S   394
   CGC CGA GGA GAG TGG GAA ATT CAG CCC AGC CGG CAG ACC AAT ACC TCA TAC CTA ACG TCT 1182

H   L   A   A   D   R   H   G   G   S   V   Q   V   V   S   S   T   N   G   E   414
   CAC TTG GCT GCA GAC CGC CAT GGG GGA TCA GTG CAG GTG GTT AGC TCA ACC AAT GGA GAG 1242

L   N   V   D   D   P   T   G   A   H   S   N   A   P   I   T   A   H   A   E   434
   CTG AAT GTT GAT GAT CCC ACG GGA GCC CAC TCC AAT GCA CCA ATC ACA GCT CAT GCC GAG 1302

V   E   V   V   E   E   A   K   C   C   C   F   F   K   R   K   R   K   K   T   454
   GTG GAG GTA GTG GAG GAA GCT AAG TGC TGC TGT TTC TTT AAG AGG AAA AGG AAG AAG ACT 1362
                                     ⌐END SEQ ID NO:5
    A   Q   R   H   K ⤎   *   ⌐END SEQ ID NO:6                                      460
   GCT CAG CGC CAC AAG TGA⤎                                                        1380

CCAGTGCCTCCCAGGAGTCCTCAGGCCCTGGGGACTCTGACTCAATTGTACCTGCAGCTCCTGCCATTTCTCATTGGAA

GGGACTCCTCTTTGGGGGAGGGTGGATATCCAAACCAAAAAGAAGAAAACAGATGCCCCCAGAAGGGGCCAGTGCGGGC

AGCCAGGGCCTAGTGGGTCATTGGCCATCTCCGCCTGCCTAAGGCTCTGAGCAGGTCCCAGAGCTGCTGTTCCTCCACT

GCTTGCCCATAGGGCTGCCTGGTTGACTCTCCTTCCCATTGTTTACAGTGAAGGTGTCATTCACAAAAACTCAAGGACT

GCTATTCTCCTTCTTCCCCTTAGTTTACTCCTGGTTTTTACCCCACCCTCAACCCTCTCCAGCATAAAACCTAGTGAGC

TAAAGGCTTTGTCTGCAGAAGGAGATCAAGAGGCTGGGGGTAAGGCCAAGAAGGTAGGAGGAAAATGGCAGACCTGGGC

TGGAGAAGAACCTTCTCCGTATCCCAGGTGTGCCTGGCAGTATGGTTTCCTCTTCCTCTGTGCCTGTGCAGCATTCATC
```

Fig. 4B

```
CCAGCTGGCCTTGGGGTTCAGGTTCCTTCTTCCCTCCCTCCTGTGAAGTTACACTGTAGGACACAAGCTGTGAGCAATC
TGCAGTCTACTGTCCCTGTGTGTTGGCGTTCTTAGCTTTTTTGACAAACTCTTTTCTCCAGGTAGTAGGACAATGAAAA
TTGTTCTAAGCAAAGGAAAGAAAACTGACTTTGTTGCACTTTTAGTTTTTTTAAAAAAAACAAAAACAAAAACATGGCA
GATGCATATTGTGTCTGGTTATATTGGGGGTTTTACTTTTACCTGTTTTGAGGGGGATGGGCCGGCCAAGCCATTCAG
AGAGAACATGGGTCCAGAGGACATTCTCAGTGGAAAGAGTTTGATCTGCAGCACCCAGAAGAGAAGCCAAACTCGGTGT
CATTCTGAGTGAACACTCAGGTTGGCAAGAAAACATACTTGAATTTTCATTCATCTTCTCAGCAGCTGAAGAATGTCCC
TACCAGAGCATCTTGACCTAATCAGCTTACAGTTTGAAAACCTAGCTCTCCAGAACATGAGATGAGCCAGCCGAGCCAG
ACTGTGACCAGGAAACAGCTCATCCCAGAGAAGGAGATGCTTAACAAAAAAAAATTGAAATTGTTTCCCATGCTGCCAG
GGACTTCCAACTAGATAGCCATGTGACGTCCTGGTGACTTGGGGGAAAAATTAGTGATGAAACAGCCACCACCATATTG
CCATTAGTGGAAAAAAAGAGGACAGTGAACCTGCCTTCCACCTGCCAGAGGGACCTCAGGGTGTGGCATTATAGGGCCA
GGAAAAGAAAATCGGTGTATCCTATCTGCCCCAATAGCTGAGCTGTAGCATTTGGGCTGGCCTGCCTTATCAGAAACCA
AGCTTATGAAGATCTTCTCCCAGCAGGTCCATAGCAGTAGGCTTAGGATGCAGTATATGGGGCCGCATTTAAAAGGAGG
GAAAGATTGTTTGGTGCTGGAACATTCCAGGGAAAAGGAGACTGGAATGAAAGGTCTGAAATTATCTTCTCAATTGGAC
TCCTTCCAGAAAGGTGGCCGTGCCTCTAAGCATGTTTTTCCCAGTATGCCCTAGGCCTCCCCCCATGGTGTTTTCATAT
GAGGTACTACTGTGAAGGATCTGGTTCCTCATTCACTGTTTGACAAGTCTTTCATGTGTGGAGTTACTCTTCTCATGCC
CAATTTTCATTTGAGTTTAGTGGCTTAACCAAACAATGACTCCTCATTCCAGCGGTGACAGAAGAGAAAGGGTCATTTA
CATCAGGAAAGAGGTCTTGTATCTGGGAGTAGAGAGCTAACCATGGAGCACAGTGGCTGGTGGGTGACTTAGTCTGATG
GTTTGTGGACCATAGAAGTCTTCACCTCTGGTTTGAGGTGCAGGGCTGTCTTTTGTACTGGAGGGTGTGGGATATTTT
CTGATAGTTGCCATTTCTTGAAAAATTCCCTTGATGTACCTTACACAGAGCAGAAATAACATTAACATGGATCAGAGGT
ACTGGGCTTCATCTGTTCCATTGGACCTTGGCTAGGGAATATCATTTCACTGGCATCAAACCTGCTTAGCTTATGAAAA
GATGGTAATATGTCATTTCTATAAATGTTTCTATATATGAAACATAAAGTGGCAGGGAGATACAATATCACACCCCTTC
CCCACAAGGACTGTGAATATTGGGATTTATGTCCTTGCCATTACCTAGTGGTTACAGCCCTATCACTAAAATTTACATC
GTTTCTCAGTTGGGATTTGGGCATTGCTAACTTACTGTATAGAAAGTTTAACTTTTCCTCACCCCTGTATAGAAAATGC
CTTGCCTCTCAAGAGAGGGCAGAGGGGGGGCCAGGTGCAGTGGCTCACGCCTGTAATCCCAGCAGTTTGGGAGGCCAAG
GCAAGTGGATCATGTGAGGTCAAGAGTTCGAGACCAGCCTGGCCAACATGGTGAAACCCCGTCTCTACAAAAAATACAA
AAATTAGCTGGGCATGGTGGCATGCTCCCGTAGTCCCAGCTACTCGGAGGCTGAGGCAGGAGAATCACTTGAGCCTGGG
AGGCAGAAGTTGCAGTGAGCCGAGATCGCACCACTGCACTCCAGCCTGGGCAACAGAGTGAGACTCTGTCTAAAAAAAA
AAAAAAAAAAGGGCG
```
END SEQ ID NO:4

Fig. 4C

```
pkinase: domain 1 of 1, from 44 to 276: score 123.3, E = 4.3e-33
                  *->yelleklGeGsfGkVykakhk.tgkivAvKilkkesls...lrEiqi
SEQ ID NO:12        +++++k+G G+fG+ +++k++ t++ vA+K  + +s  ++   E +
 15977       44    FRVGKKIGCGNFGELRLGKNLyTNEYVAIKLEPIKSRApqlHLEYRF   90 lkrls..HpNIvrllgvfedtddhlylvmEymegGdLfdylrrng.plse
                   +k+l +  + + +++++   +++   +v+E+++  +L d++  +++ ++
 15977       91    YKQLGsaGEGLPQVYYFGP-CGKYNAMVLELLGP-SLEDLFDLCDrTFTL  138 keakkialQilrGleYLHsngivHRDLKpeNILlden.....gtvKiaDF
                   k +++ia Q+l+ +eY Hs++ ++RD+KpeN+L+ ++++++++++ i+DF
 15977      139    KTVLMIAIQLLSRMEYVHSKNLIYRDVKPENFLIGRQgnkkaHVIHIIDF  188

GLArll..........eklttfvGTpwYmmAPEvilegrgysskvDvWS
                   GLA+++ +++++++ +   +++++GT +Ym +    +g++ s++ D  +
 15977      189    GLAKEYidpetkkhipyREHKSLTGTARYM-SINT-HLGKEQSRRDDLEA  236 lGviLyElltggplfpgadlpaftggdevdqliifvlklPfsdelpktri
                   lG ++  + l g                           lP+++  +t +
 15977      237    LGHMFMYFLRG-------------------------SLPWQGLKADTLK  260 dpleelfrikkr.rlp<-*
                   + ++++ + k++++++
 15977      261    ERYQKIGDTKRNtPIE     276
```

Fig. 6A

```
serkin_6: domain 1 of 1, from 44 to 329: score 64.9, E = 1.8e-15
                  *->YellkklGkGaFGkVylardkktgrlvAiKvik.....erilrEiki
SEQ ID NO:11        ++++kk+G G FG+ +l+++  t+++vAiK  + +++  ++   E +
 15977       44    FRVGKKIGCGNFGELRLGKNLYTNEYVAIKLEPiksraPQLHLEYRF    90

Lkk...dHPNIVkLydvfed.dklylVmEyceGdlGdLfdllkkrgrrgl
                   k+ ++  + + + y++    +++  +V+E+++ +l dLfdl ++
 15977       91    YKQlgsAGEGLPQVYYFGPCgKYNAMVLELLGPSLEDLFDLCDRT-----  135 rkvlsE.earfyfrQilsaLeYLHsqgIiHRDLKpeNiLLds.......h
                   ++ +++   ++ Q+ls +eY Hs++ i+RD+KPeN L+ +++++++++
 15977      136    ---FTLkTVLMIAIQLLSRMEYVHSKNLIYRDVKPENFLIGRqgnkkehV  182 vKlaDFGlArql..............ttfvGTpeYmAPEvl...gYgkpa
                   + ++DFGlA+++ +++++++ +  ++++++ GT  Ym+    ++ ++ +
 15977      183    IHIIDFGLAKEYidpetkkhipyrehKSLTGTARYMSINTHlgkEQSR-R  231 vDiWSlGcilyElltGkpPFp.....qldlifkkig..............
                   D +lG ++  +l G P+++  + ++l++ ++kig+++++++ +    ++
 15977      232    DDLEALGHMFMYFLRGSLPWQglkadTLKERYQKIGdtkrntpiealcen  281

.....................SpeakdLikklLvkdPekRlta.eaLed
                   +++   ++ ++ ++ +   ++++ + ++ L   l++k       + +   +
 15977      282    fpeematylryvrrldffekpdYEYLRTLFTDLFEKK-----GYtFDYA-  325 eldikaHPff<-*
                              ++
 15977      326    ------YDWV    329
```

Fig. 6B

```
                 ┌─BEGIN SEQ ID NO:7
                 ▼
             CCACGCGTCCGCTGCTCCTGAGCAGCCGCTGGGAGACAGACGGCAACCAGGTTGCCCCTCTTTGCTCCAGCTAGAAAGA
                                      BEGIN SEQ ID NO:8 ┐
                                      BEGIN SEQ ID NO:9 ┐  M    A    T    E    N    G    A    V    E    L       10
             CTTGAGTTAGACAAGCAGCAGCACACGCCTCCCTACCTC     ATG  GCG  ACA  GAA  AAT  GGA  GCA  GTT  GAG  CTG       30

G    I    Q    N    P    S    T    D    K    A    P    K    G    P    T    G    E    R    P    L       30
             GGA  ATT  CAG  AAC  CCA  TCA  ACA  GAC  AAG  GCA  CCT  AAA  GGT  CCC  ACA  GGT  GAA  AGA  CCC  CTG       90

A    A    G    K    D    P    G    P    P    D    P    K    K    A    P    D    P    P    T    L       50
             GCT  GCA  GGG  AAA  GAC  CCT  GGC  CCC  CCA  GAC  CCA  AAG  AAA  GCT  CCG  GAT  CCA  CCC  ACC  CTG      150

K    K    D    A    K    A    P    A    S    E    K    G    D    G    T    L    A    Q    P    S       70
             AAG  AAA  GAT  GCC  AAA  GCC  CCT  GCC  TCA  GAG  AAA  GGG  GAT  GGT  ACC  CTG  GCC  CAA  CCC  TCA      210

T    S    S    Q    G    P    K    G    E    G    D    R    G    G    G    P    A    E    G    S       90
             ACT  AGC  AGC  CAA  GGC  CCC  AAA  GGA  GAG  GGT  GAC  AGG  GGC  GGG  GGG  CCC  GCG  GAG  GGC  AGT      270

A    G    P    P    A    A    L    P    Q    Q    T    A    T    P    E    T    S    V    K    K      110
             GCT  GGG  CCC  CCG  GCA  GCC  CTG  CCC  CAG  CAG  ACT  GCG  ACA  CCT  GAG  ACC  AGC  GTC  AAG  AAG      330

P    K    A    E    Q    G    A    S    G    S    Q    D    P    G    K    P    R    V    G    K      130
             CCC  AAG  GCT  GAG  CAG  GGA  GCC  TCA  GGC  AGC  CAG  GAT  CCT  GGA  AAG  CCC  AGG  GTG  GGC  AAG      390

K    A    A    E    G    Q    A    A    A    R    R    G    S    P    A    F    L    H    S    P      150
             AAG  GCA  GCA  GAG  GGC  CAA  GCA  GCA  GCC  AGG  AGG  GGC  TCA  CCT  GCC  TTT  CTG  CAT  AGC  CCC      450

S    C    P    A    I    I    S    S    S    E    K    L    L    A    K    K    P    P    S    E      170
             AGC  TGT  CCT  GCC  ATC  ATC  TCC  AGT  TCT  GAG  AAG  CTG  CTG  GCC  AAG  AAG  CCC  CCA  AGC  GAG      510

A    S    E    L    T    F    E    G    V    P    M    T    H    S    P    T    D    P    R    P      190
             GCA  TCA  GAG  CTC  ACC  TTT  GAA  GGG  GTG  CCC  ATG  ACC  CAC  AGC  CCC  ACG  GAT  CCC  AGG  CCA      570

A    K    A    E    E    G    K    N    I    L    A    E    S    Q    K    E    V    G    E    K      210
             GCC  AAG  GCA  GAA  GAA  GGA  AAG  AAC  ATC  CTG  GCA  GAG  AGC  CAG  AAG  GAA  GTG  GGA  GAG  AAA      630

T    P    G    Q    A    G    Q    A    K    M    Q    G    D    T    S    R    G    I    E    F      230
             ACC  CCA  GGC  CAG  GCT  GGC  CAG  GCT  AAG  ATG  CAA  GGG  GAC  ACC  TCG  AGG  GGG  ATT  GAG  TTC      690

Q    A    V    P    S    E    K    S    E    V    G    Q    A    L    C    L    T    A    R    E      250
             CAG  GCT  GTT  CCC  TCA  GAG  AAA  TCC  GAG  GTG  GGG  CAG  GCC  CTC  TGT  CTC  ACA  GCC  AGG  GAG      750

E    D    C    F    Q    I    L    D    D    C    P    P    P    A    P    F    P    H    R      270
             GAG  GAC  TGC  TTC  CAG  ATT  TTG  GAT  GAT  TGC  CCG  CCA  CCT  CCG  GCC  CCC  TTC  CCT  CAC  CGC      810

M    V    E    L    R    T    G    N    V    S    S    E    F    S    M    N    S    K    E    A      290
             ATG  GTG  GAG  CTG  AGG  ACC  GGG  AAT  GTC  AGC  AGT  GAA  TTC  AGT  ATG  AAC  TCC  AAG  GAG  GCG      870
```

Fig. 7A

```
    L   G   G   G   K   F   G   A   V   C   T   C   M   E   K   A   T   G   L   K    310
   CTC GGA GGT GGC AAG TTT GGG GCA GTC TGT ACC TGC ATG GAG AAA GCC ACA GGC CTC AAG    930

L   A   A   K   V   I   K   K   Q   T   P   K   D   K   E   M   V   L   L   E    330
   CTG GCA GCC AAG GTC ATC AAG AAA CAG ACT CCC AAA GAC AAG GAA ATG GTG TTG CTG GAG    990

I   E   V   M   N   Q   L   N   H   R   N   L   I   Q   L   Y   A   A   I   E    350
   ATT GAG GTC ATG AAC CAG CTG AAC CAC CGC AAT CTG ATC CAG CTG TAT GCA GCC ATC GAG   1050

T   P   H   E   I   V   L   F   M   E   Y   I   E   G   G   E   L   F   E   R    370
   ACT CCG CAT GAG ATC GTC CTG TTC ATG GAG TAC ATC GAG GGC GGA GAG CTC TTC GAG AGG   1110

I   V   D   E   D   Y   H   L   T   E   V   D   T   M   V   F   V   R   Q   I    390
   ATT GTG GAT GAG GAC TAC CAT CTG ACC GAG GTG GAC ACC ATG GTG TTT GTC AGG CAG ATC   1170

C   D   G   I   L   F   M   H   K   M   R   V   L   H   L   D   L   K   P   E    410
   TGT GAC GGG ATC CTC TTC ATG CAC AAG ATG AGG GTT TTG CAC CTG GAC CTC AAG CCA GAG   1230

N   I   L   C   V   N   T   T   G   H   L   V   K   I   I   D   F   G   L   A    430
   AAC ATC CTG TGT GTC AAC ACC ACC GGG CAT TTG GTG AAG ATC ATT GAC TTT GGC CTG GCA   1290

R   R   Y   N   P   N   E   K   L   K   V   N   F   G   T   P   E   P   L   S    450
   CGG AGG TAT AAC CCC AAC GAG AAG CTG AAG GTG AAC TTT GGG ACC CCA GAG TTC CTG TCA   1350

P   E   V   V   N   Y   D   Q   I   S   D   K   T   D   M   W   S   M   G   V    470
   CCT GAG GTG GTG AAT TAT GAC CAA ATC TCC GAT AAG ACA GAC ATG TGG AGT ATG GGG GTG   1410

I   T   Y   M   L   L   S   G   L   S   P   F   L   G   D   D   D   T   E   T    490
   ATC ACC TAC ATG CTG CTG AGC GGC CTC TCC CCC TTC CTG GGA GAT GAT GAC ACA GAG ACC   1470

L   N   N   V   L   S   G   N   W   Y   F   D   E   E   T   F   E   A   V   S    510
   CTA AAC AAC GTT CTA TCT GGC AAC TGG TAC TTT GAT GAA GAG ACC TTT GAG GCC GTA TCA   1530

D   E   A   K   D   F   V   S   N   L   I   V   K   D   Q   R   A   R   M   N    530
   GAC GAG GCC AAA GAC TTT GTC TCC AAC CTC ATC GTC AAG GAC CAG AGG GCC CGG ATG AAC   1590

A   A   Q   C   L   A   H   P   W   L   N   N   L   A   E   K   A   K   R   C    550
   GCT GCC CAG TGT CTC GCC CAT CCC TGG CTC AAC AAC CTG GCG GAG AAA GCC AAA CGC TGT   1650

N   R   R   L   K   S   Q   I   L   L   K   K   Y   L   M   K   R   R   W   K    570
   AAC CGA CGC CTT AAG TCC CAG ATC TTG CTT AAG AAA TAC CTC ATG AAG AGG CGC TGG AAG   1710

K   N   F   I   A   V   S   A   A   N   R   F   K   K   I   S   S   S   G   A    590
   AAA AAC TTC ATT GCT GTC AGC GCT GCC AAC CGC TTC AAG AAG ATC AGC AGC TCG GGG GCA   1770
                                        ┌END SEQ ID NO:8
    L   M   A   L   G   V  ◄─ *     ┌END SEQ ID NO:9                                  597
   CTG ATG GCT CTG GGG GTC TGA ◄┘                                                    1791

GCCCTGGGCGCANTGGAAAGCCTGGACGCAGCCACACAGTGGCGGGGGCTTGAAGCCACACAGCCCAGAAGGCCAGAAA
                                                                    ┌END SEQ ID NO:7
   AGGCAGCCAGATCCCCAGGGCAGCCTCGTTAGGACAAGGCTGTGCCAAGGGCTGGGAA◄┘
```

Fig. 7B pkinase: domain 1 of 1, from 285 to 540: score 251.1, E = 1.5e-71

SEQ ID NO:13 *->yelleklGeGsfGkVykakhk.tgkivAvKilkkesls.....lrEi
+e lG G fG V + +k tg + A K++kk++ ++++ l Ei
14760  285  MNSKEALGGGKFGAVCTCMEKaTGLKLAAKVIKKQTPKdkemvLLEI  331 qilkrlsHpNIvrllgvfedtddhlylvmEymegGdLfdylrrng.plse
+++++l+H N+++l+ + e t+ ++ l mEy egG+Lf+++++++ +l+e
14760  332  EVNMQLNHRNLIQLYAAIE-TPHEIVLFMEYIEGGELFERIVDEDyHLTE  380 keakkialQilrGleYLHsngivHRDLKpeNILlden..gtvKiaDFGLA
+ +++Qi+ G+ ++H ++++H DLKpeNIL+++ +++ vKi+DFGLA
14760  381  VDTMVFVRQICDGILFMHKMRVLHLKLKPENILCVNTtgHLVKIIDFGLA  430 rll...ekltttfvGTpwYmmAPEvilegrgysskvDvWSlGviLyElltg
r ++++ekl+ + GTp++ +PEv ++++ +s k D+WS+Gvi y ll+g
14760  431  RRYnpnEKLKVNFGTPEFL-SPEV-VNYDQISDKTDMWSMGVITYMLLSG  478 gplfpgadlpaftggdevdqliifvlklPfsdelpktridpleelfrikk
+Pf + + ++++l++++++++
14760  479  ------------------------LSPFLG---DDDTETLNNVLSGNW  499 r.rlplpsncSeelkdLlkkcLnkDPskRpGsatakeilnhpwf<-*
+ ++ +S+e+kd+++ ++ kD R +a ++l+hpw+
14760  500  YfDEETFEAVSDEAKDFVSNLIVKDQRARM---NAAQCLAHPWL  540

Fig. 9A serkin_6: domain 1 of 1, from 285 to 540: score 296.2, E = 4e-85

SEQ ID NO:11 *->YellkklGkGaFGkVylardkktgrlvAiKvik.......erilrEi
+ lG G FG V+ + +k tg + A Kvik++++++e++l Ei
14760  285  MNSKEALGGGKFGAVCTCMEKATGLKLAAKVIKkqtpkdkEMVLLEI  331 kiLkk.dHPNIVkLydvfed.dklylVmEyceGdlGdLfdllkkrgrrgl
+++ + +H N+++Ly ++e+++++ l+mEy+eG G+Lf+++++ ++
14760  332  EVMNQlNHRNLIQLYAAIETpHEIVLFMEYIEG--GELFERIVDEDYH--  377 rkvlsE.earfyfrQilsaLeYLHsqgIiHRDLKpeNiLLds....hvKl
l+E ++ ++rQi++++ ++H+++++H DLKpeNiL+ +++++ vK+
14760  378  ---LTEvDTMVFVRQICDGILFMHKMRVLHLDLKPENILCVNttghLVKI  424 aDFGlArql......ttfvGTpeYmAPEvl...gYgkpavDiWSlGcily
+DFGlAr+++++++ + GTpe+++PEv++ ++ + + D+WS G+i y
14760  425  IDFGLARRYnpneklKVNFGTPEFLSPEVVnydQISD-KTDMWSMGVITY  473

ElltGkpPFp..qldlifkkig..............SpeakdLikklLvk
ll+G PF ++++ +++++++++++++ ++++ + S+eakd++++l vk
14760  474  MLLSGLSPFLgdDDTETLNNVLsgnwyfdeetfeavSDEAKDFVSNLIVK  523 dPekRlta.eaLedeldikaHPff<-*
d + R+ a ++L+ HP++
14760  524  DQRARMNAaQCLA-------HPWL  540

Fig. 9B

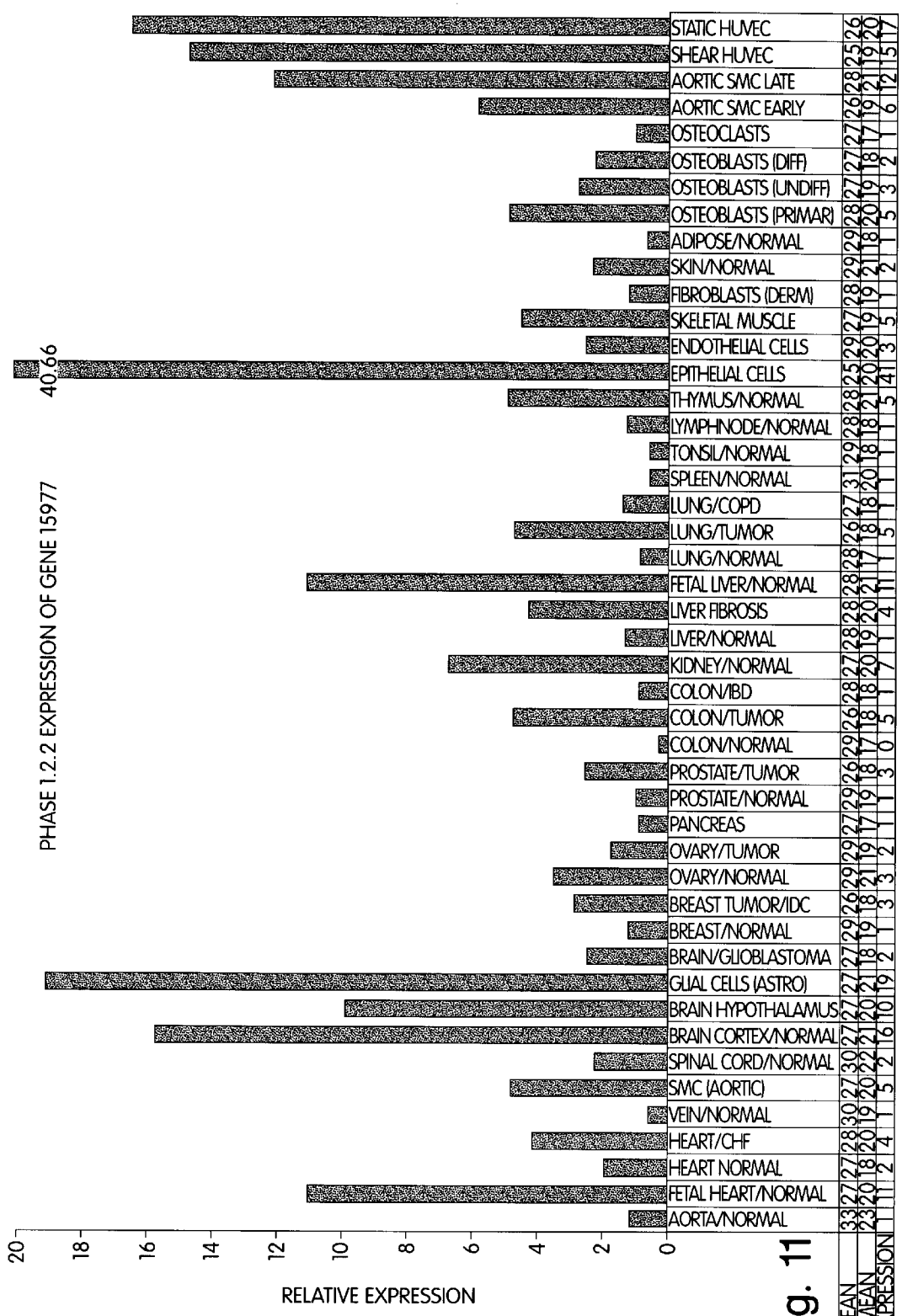

SEQUENCE LISTING

<160> NUMBER OF SEQ ID NOS: 13

<210> SEQ ID NO 1
<211> LENGTH: 2297
<212> TYPE: DNA
<213> ORGANISM: Homo sapiens
<220> FEATURE:
<221> NAME/KEY: CDS
<222> LOCATION: (154)...(1656)
<221> NAME/KEY: misc_feature
<222> LOCATION: (1)...(2297)
<223> OTHER INFORMATION: n = A,T,C or G

<400> SEQUENCE: 1

```
cacgcgtccg cgaagcggct gcatctggcg ccgcgtctgc cccgcgtgct cggagcggat      60
tctgcccgcc gtccccggag ccctcggcgc ccgctgagc ccgcgatcac ttcctccctg     120
tgaccaaccg gcgctgcagg ttagagcctg gca atg ccg ttt ggg tgt gtg act     174
                                    Met Pro Phe Gly Cys Val Thr
                                     1               5 ctg ggc gac aag aag aac tat aac cag cca tcg gag gtg act gac aga      222
Leu Gly Asp Lys Lys Asn Tyr Asn Gln Pro Ser Glu Val Thr Asp Arg
             10                  15                  20 tat gat ttg gga cag gtc atc aag act gag gag ttt tgt gaa atc ttc      270
Tyr Asp Leu Gly Gln Val Ile Lys Thr Glu Glu Phe Cys Glu Ile Phe
         25                  30                  35 cgg gcc aag gac aag acg aca ggc aag ctg cac acc tgc aag aag ttc      318
Arg Ala Lys Asp Lys Thr Thr Gly Lys Leu His Thr Cys Lys Lys Phe
 40                  45                  50                  55 cag aag cgg gac ggc cgc aag gtg cgg aaa gct gcc aag aac gag ata      366
Gln Lys Arg Asp Gly Arg Lys Val Arg Lys Ala Ala Lys Asn Glu Ile
                 60                  65                  70 ggc atc ctc aag atg gtg aag cat ccc aac atc cta cag ctg gtg gat      414
Gly Ile Leu Lys Met Val Lys His Pro Asn Ile Leu Gln Leu Val Asp
             75                  80                  85 gtg ttt gtg acc cgc aag gag tac ttt atc ttc ctg gag ctg gcc acg      462
Val Phe Val Thr Arg Lys Glu Tyr Phe Ile Phe Leu Glu Leu Ala Thr
         90                  95                 100 ggg agg gag gtg ttt gac tgg atc ctg gac cag ggc tac tac tcg gag      510
Gly Arg Glu Val Phe Asp Trp Ile Leu Asp Gln Gly Tyr Tyr Ser Glu
105                 110                 115 cga gac aca agc aac gtg gta cgg caa gtc ctg gag gcc gtg gcc tat      558
Arg Asp Thr Ser Asn Val Val Arg Gln Val Leu Glu Ala Val Ala Tyr
120                 125                 130                 135 ttg cac tca ctc aag atc gtg cac agg aat ctc aag ctg gag aac ctg      606
Leu His Ser Leu Lys Ile Val His Arg Asn Leu Lys Leu Glu Asn Leu
                140                 145                 150 gtt tac tac aac cgg ctg aag aac tcg aag att gtc atc agt gac ttc      654
Val Tyr Tyr Asn Arg Leu Lys Asn Ser Lys Ile Val Ile Ser Asp Phe
            155                 160                 165 cat ctg gct aag cta gaa aat ggc ctc atc aag gag ccc tgt ggg acc      702
His Leu Ala Lys Leu Glu Asn Gly Leu Ile Lys Glu Pro Cys Gly Thr
        170                 175                 180 ccc gag tat ctg gcc cca gag gtg gta ggc cgg cag cgg tat gga cgc      750
Pro Glu Tyr Leu Ala Pro Glu Val Val Gly Arg Gln Arg Tyr Gly Arg
    185                 190                 195 cct gtg gac tgc tgg gcc att gga gtc atc atg tac atc ctg ctt tca      798
Pro Val Asp Cys Trp Ala Ile Gly Val Ile Met Tyr Ile Leu Leu Ser
200                 205                 210                 215 ggc aat cca cct ttc tat gag gag gtg gaa gaa gat gat tat gag aac      846
```

```
                    Gly Asn Pro Pro Phe Tyr Glu Glu Val Glu Glu Asp Tyr Glu Asn
                                220                 225                 230 cat gat aag aat ctc ttc cgc aag atc ctg gct ggt gac tat gag ttt              894
His Asp Lys Asn Leu Phe Arg Lys Ile Leu Ala Gly Asp Tyr Glu Phe
            235                 240                 245 gac tct cca tat tgg gat gat att tcg cag gca gcc aaa gac ctg gtc              942
Asp Ser Pro Tyr Trp Asp Asp Ile Ser Gln Ala Ala Lys Asp Leu Val
        250                 255                 260 aca agg ctg atg gag gtg gag caa gac cag cgg atc act gca gaa gag              990
Thr Arg Leu Met Glu Val Glu Gln Asp Gln Arg Ile Thr Ala Glu Glu
    265                 270                 275 gcc atc tcc cat gag tgg att tct ggc aat gct gct tct gat aag aac             1038
Ala Ile Ser His Glu Trp Ile Ser Gly Asn Ala Ala Ser Asp Lys Asn
280                 285                 290                 295 atc aag gat ggt gtc tgt gcc cag att gaa aag aac ttt gcc agg gcc             1086
Ile Lys Asp Gly Val Cys Ala Gln Ile Glu Lys Asn Phe Ala Arg Ala
                300                 305                 310 aag tgg aag aag gct gtc cga gtg acc acc ctc atg aaa cgg ctc cgg             1134
Lys Trp Lys Lys Ala Val Arg Val Thr Thr Leu Met Lys Arg Leu Arg
            315                 320                 325 gca cca gag cag tcc agc acg gct gca gcc cag tcg gcc tca gcc aca             1182
Ala Pro Glu Gln Ser Ser Thr Ala Ala Ala Gln Ser Ala Ser Ala Thr
        330                 335                 340 gac act gcc acc ccc ggg gct gca ggt ggg gcc aca gct gca gct gcg             1230
Asp Thr Ala Thr Pro Gly Ala Ala Gly Gly Ala Thr Ala Ala Ala Ala
    345                 350                 355 agt gga gct acc tca gcc cct gag ggt gat gct gct cgt gct gca aag             1278
Ser Gly Ala Thr Ser Ala Pro Glu Gly Asp Ala Ala Arg Ala Ala Lys
360                 365                 370                 375 agt gat aat gtg gcc ccc gca gac cgt agt gcc acc cca gcc aca gat             1326
Ser Asp Asn Val Ala Pro Ala Asp Arg Ser Ala Thr Pro Ala Thr Asp
                380                 385                 390 gga agt gcc acc cca gcc act gat ggc agt gtc acc cca gcc acc gat             1374
Gly Ser Ala Thr Pro Ala Thr Asp Gly Ser Val Thr Pro Ala Thr Asp
            395                 400                 405 gga agc atc act cca gcc act gat ggg agt gtc acc cca gcc act gac             1422
Gly Ser Ile Thr Pro Ala Thr Asp Gly Ser Val Thr Pro Ala Thr Asp
        410                 415                 420 agg agc gct act cca gcc act gat ggg aga gcc aca cca gcc aca gaa             1470
Arg Ser Ala Thr Pro Ala Thr Asp Gly Arg Ala Thr Pro Ala Thr Glu
    425                 430                 435 gag agc act gtg ccc acc acc caa agc agt gcc atg ctg gcc acc aag             1518
Glu Ser Thr Val Pro Thr Thr Gln Ser Ser Ala Met Leu Ala Thr Lys
440                 445                 450                 455 gca gct gcc acc cct gag ccg gct atg gcc cag ccg gac agc aca gcc             1566
Ala Ala Ala Thr Pro Glu Pro Ala Met Ala Gln Pro Asp Ser Thr Ala
                460                 465                 470 cca gag ggc gcc aca ggc cag gct cca ccc tct agt aaa ggg gaa gag             1614
Pro Glu Gly Ala Thr Gly Gln Ala Pro Pro Ser Ser Lys Gly Glu Glu
            475                 480                 485 gct gct ggt tat gcc cag gag tct caa agg gag gag gcc agc                     1656
Ala Ala Gly Tyr Ala Gln Glu Ser Gln Arg Glu Glu Ala Ser
        490                 495                 500 tgagtaggca gcctggtgag ggggggcagg ggatgggcag gagggtggga gagtggatga          1716
ggggcttctc actgtacata gagtcactgg catgatgccc tcgctccccc atgccccac           1776 atcccagtgg ggcataacta gggtcacgg gagagcagtc tcgtctcctg tgtgtatgtg           1836
tgtgagtggt gggcaggcca gtggcagggc cggccccagc ccctgcatgg attccttgtg          1896
```

-continued

```
gcttttctgt cttttgctag cttcaccagt ttctgttcct tgtgggatgc tgctctaggg    1956
atactcaggg ggctcctgct ctccttcccc ttcccttctt gcctcaccat tccctaggc    2016 aggccctgca gtcccacac tctcccaggc cctaaacttg gcggccttg ccctgagagc    2076 tggtcctcca gcgaggccct gtcagcggtc ttaggctcct gcacatgaag gtgtgtgcct    2136
gtggtgtgtg ggctgctcta ggagcagata caggctggta tagaggatgc agaaaggtag    2196
ggcagtatgt ttaagtccag acttggcaca tggctaggga tactgctcac tagctgtgga    2256
ggtcctcagg agtggagaga atgagtagga nggcagaanc t                        2297
```

<210> SEQ ID NO 2
<211> LENGTH: 501
<212> TYPE: PRT
<213> ORGANISM: Homo sapiens

<400> SEQUENCE: 2

```
Met Pro Phe Gly Cys Val Thr Leu Gly Asp Lys Lys Asn Tyr Asn Gln
  1               5                  10                  15

Pro Ser Glu Val Thr Asp Arg Tyr Asp Leu Gly Gln Val Ile Lys Thr
             20                  25                  30

Glu Glu Phe Cys Glu Ile Phe Arg Ala Lys Asp Lys Thr Thr Gly Lys
         35                  40                  45

Leu His Thr Cys Lys Lys Phe Gln Lys Arg Asp Gly Arg Lys Val Arg
     50                  55                  60

Lys Ala Lys Asn Glu Ile Gly Ile Leu Lys Met Val Lys His Pro
 65                  70                  75                  80

Asn Ile Leu Gln Leu Val Asp Val Phe Val Thr Arg Lys Glu Tyr Phe
                 85                  90                  95

Ile Phe Leu Glu Leu Ala Thr Gly Arg Glu Val Phe Asp Trp Ile Leu
            100                 105                 110

Asp Gln Gly Tyr Tyr Ser Glu Arg Asp Thr Ser Asn Val Val Arg Gln
        115                 120                 125

Val Leu Glu Ala Val Ala Tyr Leu His Ser Leu Lys Ile Val His Arg
    130                 135                 140

Asn Leu Lys Leu Glu Asn Leu Val Tyr Tyr Asn Arg Leu Lys Asn Ser
145                 150                 155                 160

Lys Ile Val Ile Ser Asp Phe His Leu Ala Lys Leu Glu Asn Gly Leu
                165                 170                 175

Ile Lys Glu Pro Cys Gly Thr Pro Glu Tyr Leu Ala Pro Glu Val Val
            180                 185                 190

Gly Arg Gln Arg Tyr Gly Arg Pro Val Asp Cys Trp Ala Ile Gly Val
        195                 200                 205

Ile Met Tyr Ile Leu Leu Ser Gly Asn Pro Pro Phe Tyr Glu Glu Val
    210                 215                 220

Glu Glu Asp Asp Tyr Glu Asn His Asp Lys Asn Leu Phe Arg Lys Ile
225                 230                 235                 240

Leu Ala Gly Asp Tyr Glu Phe Asp Ser Pro Tyr Trp Asp Asp Ile Ser
                245                 250                 255

Gln Ala Ala Lys Asp Leu Val Thr Arg Leu Met Glu Val Glu Gln Asp
            260                 265                 270

Gln Arg Ile Thr Ala Glu Glu Ala Ile Ser His Glu Trp Ile Ser Gly
        275                 280                 285

Asn Ala Ala Ser Asp Lys Asn Ile Lys Asp Gly Val Cys Ala Gln Ile
    290                 295                 300
```

-continued

```
Glu Lys Asn Phe Ala Arg Ala Lys Trp Lys Lys Ala Val Arg Val Thr
305                 310                 315                 320

Thr Leu Met Lys Arg Leu Arg Ala Pro Glu Gln Ser Ser Thr Ala Ala
                325                 330                 335

Ala Gln Ser Ala Ser Ala Thr Asp Thr Ala Thr Pro Gly Ala Ala Gly
            340                 345                 350

Gly Ala Thr Ala Ala Ala Ala Ser Gly Ala Thr Ser Ala Pro Glu Gly
        355                 360                 365

Asp Ala Ala Arg Ala Ala Lys Ser Asp Asn Val Ala Pro Ala Asp Arg
    370                 375                 380

Ser Ala Thr Pro Ala Thr Asp Gly Ser Ala Thr Pro Ala Thr Asp Gly
385                 390                 395                 400

Ser Val Thr Pro Ala Thr Asp Gly Ser Ile Thr Pro Ala Thr Asp Gly
                405                 410                 415

Ser Val Thr Pro Ala Thr Asp Arg Ser Ala Thr Pro Ala Thr Asp Gly
            420                 425                 430

Arg Ala Thr Pro Ala Thr Glu Glu Ser Thr Val Pro Thr Thr Gln Ser
        435                 440                 445

Ser Ala Met Leu Ala Thr Lys Ala Ala Ala Thr Pro Glu Pro Ala Met
    450                 455                 460

Ala Gln Pro Asp Ser Thr Ala Pro Glu Gly Ala Thr Gly Gln Ala Pro
465                 470                 475                 480

Pro Ser Ser Lys Gly Glu Glu Ala Ala Gly Tyr Ala Gln Glu Ser Gln
                485                 490                 495

Arg Glu Glu Ala Ser
            500

<210> SEQ ID NO 3
<211> LENGTH: 1503
<212> TYPE: DNA
<213> ORGANISM: Homo sapiens

<400> SEQUENCE: 3
atgccgtttg ggtgtgtgac tctgggcgac aagaagaact ataaccagcc atcggaggtg      60
actgacagat atgatttggg acaggtcatc aagactgagg agttttgtga aatcttccgg     120
gccaaggaca agacgacagg caagctgcac acctgcaaga agttccagaa gcgggacggc     180
cgcaaggtgc ggaaagctgc caagaacgag ataggcatcc tcaagatggt gaagcatccc     240
aacatcctac agctggtgga tgtgtttgtg acccgcaagg agtactttat cttcctggag     300
ctggccacgg ggagggaggt gtttgactgg atcctggacc agggctacta ctcggagcga     360
gacacaagca acgtggtacg gcaagtcctg gaggccgtgg cctatttgca ctcactcaag     420
atcgtgcaca ggaatctcaa gctggagaac ctggtttact acaaccggct gaagaactcg     480
aagattgtca tcagtgactt ccatctggct aagctagaaa atggcctcat caaggagccc     540
tgtgggaccc ccgagtatct ggccccagag gtggtaggcc ggcagcggta tggacgccct     600
gtggactgct gggccattgg agtcatcatg tacatcctgc tttcaggcaa tccacctttc     660
tatgaggagg tggaagaaga tgattatgag aaccatgata agaatctctt ccgcaagatc     720
ctggctggtg actatgagtt tgactctcca tattgggatg atatttcgca ggcagccaaa     780
gacctggtca aaggctgatg gaggtggag caagaccagc ggatcactgc agaagaggcc     840
atctcccatg agtggatttc tggcaatgct gcttctgata agaacatcaa ggatggtgtc     900
tgtgcccaga ttgaaaagaa ctttgccagg gccaagtgga agaaggctgt ccgagtgacc     960
```

```
accctcatga acggctccg ggcaccagag cagtccagca cggctgcagc ccagtcggcc    1020
tcagccacag acactgccac ccccggggct gcaggtgggg ccacagctgc agctgcgagt    1080
ggagctacct cagcccctga gggtgatgct gctcgtgctg caaagagtga taatgtggcc    1140
cccgcagacc gtagtgccac cccagccaca gatggaagtg ccaccccagc cactgatggc    1200
agtgtcaccc cagccaccga tggaagcatc actccagcca ctgatgggag tgtcacccca    1260
gccactgaca ggagcgctac tccagccact gatgggagac cacaccagc cacagaagag    1320 agcactgtgc ccaccaccca agcagtgcca tgctggcca ccaaggcagc tgccaccct    1380 gagccggcta tggcccagcc ggacagcaca gccccagagg gcgccacagg ccaggctcca    1440
ccctctagta aggggaaga ggctgctggt tatgcccagg agtctcaaag ggaggaggcc    1500
agc                                                                1503

<210> SEQ ID NO 4
<211> LENGTH: 4417
<212> TYPE: DNA
<213> ORGANISM: Homo sapiens
<220> FEATURE:
<221> NAME/KEY: CDS
<222> LOCATION: (337)...(1713)

<400> SEQUENCE: 4
gggagcgccc cgcgtccggg acaagccgca gacaaaaccc ctcagacacc aaagggcttt     60
attcggccgg gagcatcagc aaacttaggt ctcaaaaaac caagctctcc aagttacaag    120
atgttcacct aagattgaga cctagtgact acgtttccta cgggaacaaa taatggtttt    180
tcatctcccc ggagatacat tacaaacaaa tatggtgcta aaagaactcc ttacctttct    240
ctgactacaa tttatttgga catacttttg tattgaagag aggtatacat actgaagcta    300
cttgctgtac tataggagac tctgtcctgt aggatc atg gac cat cct agt agg     354
                                        Met Asp His Pro Ser Arg
                                          1               5 gaa aag gat gaa aga caa cgg aca act aaa ccc atg gca caa agg agt     402
Glu Lys Asp Glu Arg Gln Arg Thr Thr Lys Pro Met Ala Gln Arg Ser
            10                  15                  20 gca cac tgc tct cga cca tct ggc tcc tca tcg tcc tct ggg gtt ctt     450
Ala His Cys Ser Arg Pro Ser Gly Ser Ser Ser Ser Ser Gly Val Leu
        25                  30                  35 atg gtg gga ccc aac ttc agg gtt ggc aag aag ata gga tgt ggg aac     498
Met Val Gly Pro Asn Phe Arg Val Gly Lys Lys Ile Gly Cys Gly Asn
    40                  45                  50 ttc gga gag ctc aga tta ggt aaa aat ctc tac acc aat gaa tat gta     546
Phe Gly Glu Leu Arg Leu Gly Lys Asn Leu Tyr Thr Asn Glu Tyr Val
55                  60                  65                  70 gca atc aaa ctg gaa cca ata aaa tca cgt gct cca cag ctt cat tta     594
Ala Ile Lys Leu Glu Pro Ile Lys Ser Arg Ala Pro Gln Leu His Leu
                75                  80                  85 gag tac aga ttt tat aaa cag ctt ggc agt gca ggt gaa ggt ctc cca     642
Glu Tyr Arg Phe Tyr Lys Gln Leu Gly Ser Ala Gly Glu Gly Leu Pro
            90                  95                 100 cag gtg tat tac ttt gga cca tgt ggg aaa tat aat gcc atg gtg ctg     690
Gln Val Tyr Tyr Phe Gly Pro Cys Gly Lys Tyr Asn Ala Met Val Leu
        105                 110                 115 gag ctc ctt ggc cct agc ttg gag gac ttg ttt gac ctc tgt gac cga     738
Glu Leu Leu Gly Pro Ser Leu Glu Asp Leu Phe Asp Leu Cys Asp Arg
    120                 125                 130 aca ttt act ttg aag acg gtg tta atg ata gcc atc cag ctg ctt tct     786
Thr Phe Thr Leu Lys Thr Val Leu Met Ile Ala Ile Gln Leu Leu Ser
```

-continued

```
         135                 140                 145                 150
cga atg gaa tac gtg cac tca aag aac ctc att tac cga gat gtc aag          834
Arg Met Glu Tyr Val His Ser Lys Asn Leu Ile Tyr Arg Asp Val Lys
                    155                 160                 165 cca gag aac ttc ctg att ggt cga caa ggc aat aag aaa gag cat gtt          882
Pro Glu Asn Phe Leu Ile Gly Arg Gln Gly Asn Lys Lys Glu His Val
                170                 175                 180 ata cac att ata gac ttt gga ctg gcc aag gaa tac att gac ccc gaa          930
Ile His Ile Ile Asp Phe Gly Leu Ala Lys Glu Tyr Ile Asp Pro Glu
            185                 190                 195 acc aaa aaa cac ata cct tat agg gaa cac aaa agt tta act gga act          978
Thr Lys Lys His Ile Pro Tyr Arg Glu His Lys Ser Leu Thr Gly Thr
        200                 205                 210 gcg aga tat atg tct atc aac acg cat ctt ggc aaa gag caa agc cgg         1026
Ala Arg Tyr Met Ser Ile Asn Thr His Leu Gly Lys Glu Gln Ser Arg
215                 220                 225                 230 aga gat gat ttg gaa gcc cta ggc cat atg ttc atg tat ttc ctt cga         1074
Arg Asp Asp Leu Glu Ala Leu Gly His Met Phe Met Tyr Phe Leu Arg
                    235                 240                 245 ggc agc ctc ccc tgg caa gga ctc aag gct gac aca tta aaa gag aga         1122
Gly Ser Leu Pro Trp Gln Gly Leu Lys Ala Asp Thr Leu Lys Glu Arg
                250                 255                 260 tat caa aaa att ggt gac acc aaa agg aat act ccc att gaa gct ctc         1170
Tyr Gln Lys Ile Gly Asp Thr Lys Arg Asn Thr Pro Ile Glu Ala Leu
            265                 270                 275 tgt gag aac ttt cca gag gag atg gca acc tac ctt cga tat gtc agg         1218
Cys Glu Asn Phe Pro Glu Glu Met Ala Thr Tyr Leu Arg Tyr Val Arg
        280                 285                 290 cga ctg gac ttc ttt gaa aaa cct gat tat gag tat tta cgg acc ctc         1266
Arg Leu Asp Phe Phe Glu Lys Pro Asp Tyr Glu Tyr Leu Arg Thr Leu
295                 300                 305                 310 ttc aca gac ctc ttt gaa aag aaa ggc tac acc ttt gac tat gcc tat         1314
Phe Thr Asp Leu Phe Glu Lys Lys Gly Tyr Thr Phe Asp Tyr Ala Tyr
                    315                 320                 325 gat tgg gtt ggg aga cct att cct act cca gta ggg tca gtt cac gta         1362
Asp Trp Val Gly Arg Pro Ile Pro Thr Pro Val Gly Ser Val His Val
                330                 335                 340 gat tct ggt gca tct gca ata act cga gaa agc cac aca cat agg gat         1410
Asp Ser Gly Ala Ser Ala Ile Thr Arg Glu Ser His Thr His Arg Asp
            345                 350                 355 cgg cca tca caa cag cag cct ctt cga aat cag aat gta tca tca gag         1458
Arg Pro Ser Gln Gln Gln Pro Leu Arg Asn Gln Asn Val Ser Ser Glu
        360                 365                 370 cgc cga gga gag tgg gaa att cag ccc agc cgg cag acc aat acc tca         1506
Arg Arg Gly Glu Trp Glu Ile Gln Pro Ser Arg Gln Thr Asn Thr Ser
375                 380                 385                 390 tac cta acg tct cac ttg gct gca gac cgc cat ggg gga tca gtg cag         1554
Tyr Leu Thr Ser His Leu Ala Ala Asp Arg His Gly Gly Ser Val Gln
                    395                 400                 405 gtg gtt agc tca acc aat gga gag ctg aat gtt gat gat ccc acg gga         1602
Val Val Ser Ser Thr Asn Gly Glu Leu Asn Val Asp Asp Pro Thr Gly
                410                 415                 420 gcc cac tcc aat gca cca atc aca gct cat gcc gag gtg gag gta gtg         1650
Ala His Ser Asn Ala Pro Ile Thr Ala His Ala Glu Val Glu Val Val
            425                 430                 435 gag gaa gct aag tgc tgc tgt ttc ttt aag agg aaa agg aag aag act         1698
Glu Glu Ala Lys Cys Cys Cys Phe Phe Lys Arg Lys Arg Lys Lys Thr
        440                 445                 450 gct cag cgc cac aag tgaccagtgc ctcccaggag tcctcaggcc ctggggactc         1753
Ala Gln Arg His Lys
```

Ala Gln Arg His Lys
455

```
tgactcaatt gtacctgcag ctcctgccat ttctcattgg aagggactcc tctttgggg   1813
agggtggata tccaaaccaa aaagaagaaa acagatgccc ccagaagggg ccagtgcggg   1873
cagccagggc ctagtgggtc attggccatc tccgcctgcc taaggctctg agcaggtccc   1933
agagctgctg ttcctccact gcttgccat agggctgcct ggttgactct ccttcccatt   1993
gtttacagtg aaggtgtcat tcacaaaaac tcaaggactg ctattctcct tcttcccctt   2053
agtttactcc tggtttttac cccaccctca accctctcca gcataaaacc tagtgagcta   2113
aaggctttgt ctgcagaagg agatcaagag gctgggggta aggccaagaa ggtaggagga   2173
aaatggcaga cctgggctgg agaagaacct tctccgtatc ccaggtgtgc ctggcagtat   2233
ggtttcctct tcctctgtgc ctgtgcagca ttcatcccag ctggccttgg ggttcaggtt   2293
ccttcttccc tccctcctgt gaagttacac tgtaggacaa aagctgtgag caatctgcag   2353
tctactgtcc ctgtgtgttg gcgttcttag cttttttgac aaactctttt ctccaggtag   2413
taggacaatg aaaattgttc taagcaaagg aaagaaaact gactttgttg cactttagt   2473
ttttttaaaa aaacaaaaa caaaaacatg gcagatgcat attgtgtctg gttatattgg   2533
gggttttact tttacctgtt ttgagggggga tggggccggc caagccattc agagagaaca   2593
tgggtccaga ggacattctc agtggaaaga gtttgatctg cagcacccag aagagaagcc   2653
aaactcggtg tcattctgag tgaacactca ggttggcaag aaaacatact tgaatttca   2713
ttcatcttct cagcagctga agaatgtccc taccagagca tcttgaccta atcagcttac   2773
agtttgaaaa cctagctctc cagaacatga gatgagccag ccgagccaga ctgtgaccag   2833
gaaacagctc atcccagaga aggagatgct taacaaaaaa aaattgaaat tgtttcccat   2893
gctgccaggg acttccaact agatagccat gtgacgtcct ggtgacttgg gggaaaaatt   2953
agtgatgaaa cagccaccac catattgcca ttagtggaaa aaagaggac agtgaacctg   3013
ccttccacct gccagaggga cctcaggtg tggcattata gggccaggaa aagaaaatcg   3073
gtgtatccta tctgccccaa tagctgagct gtagcatttg ggctggcctg ccttatcaga   3133
aaccaagctt atgaagatct tctcccagca ggtccatagc agtaggctta ggatgcagta   3193
tatggggccg catttaaaag gagggaaaga ttgtttggtg ctggaacatt ccagggaaaa   3253
ggagactgga atgaaaggtc tgaaattatc ttctcaattg gactccttcc agaaggtgg   3313
ccgtgcctct aagcatgttt ttcccagtat gccctaggcc tcccccatg gtgttttcat   3373
atgaggtact actgtgaagg atctggttcc tcattcactg tttgacaagt cttttcatgtg   3433
tggagttact cttctcatgc ccaatttca tttgagttta gtggcttaac caaacaatga   3493
ctcctcattc cagcggtgac agaagagaaa gggtcattta catcaggaaa gaggtcttgt   3553
atctgggagt agagagctaa ccatggagca cagtggctgg tgggtgactt agtctgatgg   3613
tttgtggacc atagaagtct tcacctctgg tttgaggtgc agggctgtct tttgtactgg   3673
agggtgtggg gatattttct gatagttgcc atttcttgaa aaattccctt gatgtacctt   3733
acacagagca gaaataacat taacatggat cagaggtact gggcttcatc tgttccattg   3793
gaccttggct agggaatatc atttcactgg catcaaacct gcttagctta tgaaaagatg   3853
gtaatatgtc atttctataa atgtttctat atatgaaaca taaagtggca gggagataca   3913
atatcacacc cctttcccac aaggactgtg aatattggga tttatgtcct tgccattacc   3973
tagtggttac agccctatca ctaaaattta catcgtttct cagttgggat ttgggcattg   4033
```

-continued

```
ctaacttact gtatagaaag tttaactttt cctcacccct gtatagaaaa tgccttgcct    4093
ctcaagagag ggcagagggg gggccaggtg cagtggctca cgcctgtaat cccagcagtt    4153
tgggaggcca aggcaagtgg atcatgtgag gtcaagagtt cgagaccagc ctggccaaca    4213
tggtgaaacc ccgtctctac aaaaaataca aaaattagct gggcatggtg gcatgctccc    4273
gtagtcccag ctactcggag gctgaggcag gagaatcact tgagcctggg aggcagaagt    4333
tgcagtgagc cgagatcgca ccactgcact ccagcctggg caacagagtg agactctgtc    4393
taaaaaaaaa aaaaaaaaag ggcg                                          4417
```

<210> SEQ ID NO 5
<211> LENGTH: 459
<212> TYPE: PRT
<213> ORGANISM: Homo sapiens

<400> SEQUENCE: 5

```
Met Asp His Pro Ser Arg Glu Lys Asp Glu Arg Gln Arg Thr Thr Lys
 1               5                  10                  15

Pro Met Ala Gln Arg Ser Ala His Cys Ser Arg Pro Ser Gly Ser Ser
                20                  25                  30

Ser Ser Ser Gly Val Leu Met Val Gly Pro Asn Phe Arg Val Gly Lys
            35                  40                  45

Lys Ile Gly Cys Gly Asn Phe Gly Glu Leu Arg Leu Gly Lys Asn Leu
        50                  55                  60

Tyr Thr Asn Glu Tyr Val Ala Ile Lys Leu Glu Pro Ile Lys Ser Arg
 65                  70                  75                  80

Ala Pro Gln Leu His Leu Glu Tyr Arg Phe Tyr Lys Gln Leu Gly Ser
                85                  90                  95

Ala Gly Glu Gly Leu Pro Gln Val Tyr Tyr Phe Gly Pro Cys Gly Lys
            100                 105                 110

Tyr Asn Ala Met Val Leu Glu Leu Leu Gly Pro Ser Leu Glu Asp Leu
        115                 120                 125

Phe Asp Leu Cys Asp Arg Thr Phe Thr Leu Lys Thr Val Leu Met Ile
    130                 135                 140

Ala Ile Gln Leu Leu Ser Arg Met Glu Tyr Val His Ser Lys Asn Leu
145                 150                 155                 160

Ile Tyr Arg Asp Val Lys Pro Glu Asn Phe Leu Ile Gly Arg Gln Gly
                165                 170                 175

Asn Lys Lys Glu His Val Ile His Ile Ile Asp Phe Gly Leu Ala Lys
            180                 185                 190

Glu Tyr Ile Asp Pro Glu Thr Lys Lys His Ile Pro Tyr Arg Glu His
        195                 200                 205

Lys Ser Leu Thr Gly Thr Ala Arg Tyr Met Ser Ile Asn Thr His Leu
    210                 215                 220

Gly Lys Glu Gln Ser Arg Arg Asp Asp Leu Glu Ala Leu Gly His Met
225                 230                 235                 240

Phe Met Tyr Phe Leu Arg Gly Ser Leu Pro Trp Gln Gly Leu Lys Ala
                245                 250                 255

Asp Thr Leu Lys Glu Arg Tyr Gln Lys Ile Gly Asp Thr Lys Arg Asn
            260                 265                 270

Thr Pro Ile Glu Ala Leu Cys Glu Asn Phe Pro Glu Glu Met Ala Thr
        275                 280                 285

Tyr Leu Arg Tyr Val Arg Arg Leu Asp Phe Phe Glu Lys Pro Asp Tyr
    290                 295                 300
```

```
Glu Tyr Leu Arg Thr Leu Phe Thr Asp Leu Phe Glu Lys Lys Gly Tyr
305                 310                 315                 320

Thr Phe Asp Tyr Ala Tyr Asp Trp Val Gly Arg Pro Ile Pro Thr Pro
                325                 330                 335

Val Gly Ser Val His Val Asp Ser Gly Ala Ser Ala Ile Thr Arg Glu
            340                 345                 350

Ser His Thr His Arg Asp Arg Pro Ser Gln Gln Pro Leu Arg Asn
        355                 360                 365

Gln Asn Val Ser Ser Glu Arg Arg Gly Glu Trp Glu Ile Gln Pro Ser
    370                 375                 380

Arg Gln Thr Asn Thr Ser Tyr Leu Thr Ser His Leu Ala Ala Asp Arg
385                 390                 395                 400

His Gly Gly Ser Val Gln Val Val Ser Ser Thr Asn Gly Glu Leu Asn
                405                 410                 415

Val Asp Asp Pro Thr Gly Ala His Ser Asn Ala Pro Ile Thr Ala His
                420                 425                 430

Ala Glu Val Glu Val Val Glu Glu Ala Lys Cys Cys Cys Phe Phe Lys
            435                 440                 445

Arg Lys Arg Lys Lys Thr Ala Gln Arg His Lys
    450                 455

<210> SEQ ID NO 6
<211> LENGTH: 1377
<212> TYPE: DNA
<213> ORGANISM: Homo sapiens

<400> SEQUENCE: 6
atggaccatc ctagtaggga aaaggatgaa agacaacgga caactaaacc catggcacaa      60
aggagtgcac actgctctcg accatctggc tcctcatcgt cctctgggt tcttatggtg     120 ggacccaact tcagggttgg caagaagata ggatgtggga acttcggaga gctcagatta     180
ggtaaaaatc tctacaccaa tgaatatgta gcaatcaaac tggaaccaat aaaatcacgt     240
gctccacagc ttcatttaga gtacagattt tataaacagc ttggcagtgc aggtgaaggt     300
ctcccacagg tgtattactt tggaccatgt gggaaatata tgccatggt gctggagctc     360 cttggcccta gctggaggaa cttgtttgac ctctgtgacc gaacatttac tttgaagacg     420
gtgttaatga tagccatcca gctgctttct cgaatggaat acgtgcactc aaagaaccctc     480 atttaccgag atgtcaagcc agagaacttc ctgattggtc gacaaggcaa taagaaagag     540
catgttatac acattataga ctttggactg gccaaggaat acattgaccc cgaaaccaaa     600
aaacacatac cttatagga acacaaaagt ttaactggaa ctgcgagata tatgtctatc     660
aacacgcatc ttggcaaaga gcaaagccgg agagatgatt tggaagccct aggccatatg     720
ttcatgtatt tccttcgagg cagcctcccc tggcaaggac tcaaggctga cacattaaaa     780
gagagatatc aaaaaattgg tgacaccaaa aggaatactc ccattgaagc tctctgtgag     840
aactttccag aggagatggc aacctaccctt cgatatgtca ggcgactgga cttctttgaa     900
aaacctgatt atgagtattt acggaccctc ttcacagacc tctttgaaaa gaaaggctac     960
acctttgact atgcctatga ttgggttggg agaccatattc ctactccagt agggtcagtt    1020
cacgtagatt ctggtgcatc tgcaataact cgagaaagcc acacacatag ggatcggcca    1080
tcacaacagc agcctcttcg aaatcagaat gtatcatcag agcgccgagg agagtgggaa    1140
attcagccca gccggcagac caatacctca tacctaacgt ctcacttggc tgcagaccgc    1200
catgggggat cagtgcaggt ggttagctca accaatggag agctgaatgt tgatgatccc    1260
```

```
acgggagccc actccaatgc accaatcaca gctcatgccg aggtggaggt agtggaggaa   1320
gctaagtgct gctgtttctt taagaggaaa aggaagaaga ctgctcagcg ccacaag      1377

<210> SEQ ID NO 7
<211> LENGTH: 2046
<212> TYPE: DNA
<213> ORGANISM: Homo sapiens
<220> FEATURE:
<221> NAME/KEY: CDS
<222> LOCATION: (119)...(1906)
<221> NAME/KEY: misc_feature
<222> LOCATION: (1)...(2046)
<223> OTHER INFORMATION: n = A,T,C or G

<400> SEQUENCE: 7
ccacgcgtcc gctgctcctg agcagccgct gggagacaga cggcaaccag gttgcccctc   60
tttgctccag ctagaaagac ttgagttaga caagcagcag cacacgcctc cctacctc    118 atg gcg aca gaa aat gga gca gtt gag ctg gga att cag aac cca tca    166
Met Ala Thr Glu Asn Gly Ala Val Glu Leu Gly Ile Gln Asn Pro Ser
 1               5                  10                  15 aca gac aag gca cct aaa ggt ccc aca ggt gaa aga ccc ctg gct gca    214
Thr Asp Lys Ala Pro Lys Gly Pro Thr Gly Glu Arg Pro Leu Ala Ala
                 20                  25                  30 ggg aaa gac cct ggc ccc cca gac cca aag aaa gct ccg gat cca ccc    262
Gly Lys Asp Pro Gly Pro Pro Asp Pro Lys Lys Ala Pro Asp Pro Pro
             35                  40                  45 acc ctg aag aaa gat gcc aaa gcc cct gcc tca gag aaa ggg gat ggt    310
Thr Leu Lys Lys Asp Ala Lys Ala Pro Ala Ser Glu Lys Gly Asp Gly
         50                  55                  60 acc ctg gcc caa ccc tca act agc agc caa ggc ccc aaa gga gag ggt    358
Thr Leu Ala Gln Pro Ser Thr Ser Ser Gln Gly Pro Lys Gly Glu Gly
 65                  70                  75                  80 gac agg ggc ggg ggg ccc gcg gag ggc agt gct ggg ccc ccg gca gcc    406
Asp Arg Gly Gly Gly Pro Ala Glu Gly Ser Ala Gly Pro Pro Ala Ala
                 85                  90                  95 ctg ccc cag cag act gcg aca cct gag acc agc gtc aag aag ccc aag    454
Leu Pro Gln Gln Thr Ala Thr Pro Glu Thr Ser Val Lys Lys Pro Lys
                100                 105                 110 gct gag cag gga gcc tca ggc agc cag gat cct gga aag ccc agg gtg    502
Ala Glu Gln Gly Ala Ser Gly Ser Gln Asp Pro Gly Lys Pro Arg Val
            115                 120                 125 ggc aag aag gca gca gag ggc caa gca gca gcc agg agg ggc tca cct    550
Gly Lys Lys Ala Ala Glu Gly Gln Ala Ala Ala Arg Arg Gly Ser Pro
        130                 135                 140 gcc ttt ctg cat agc ccc agc tgt cct gcc atc atc tcc agt tct gag    598
Ala Phe Leu His Ser Pro Ser Cys Pro Ala Ile Ile Ser Ser Ser Glu
145                 150                 155                 160 aag ctg ctg gcc aag aag ccc cca agc gag gca tca gag ctc acc ttt    646
Lys Leu Leu Ala Lys Lys Pro Pro Ser Glu Ala Ser Glu Leu Thr Phe
                165                 170                 175 gaa ggg gtg ccc atg acc cac agc ccc acg gat ccc agg cca gcc aag    694
Glu Gly Val Pro Met Thr His Ser Pro Thr Asp Pro Arg Pro Ala Lys
            180                 185                 190 gca gaa gaa gga aag aac atc ctg gca gag agc cag aag gaa gtg gga    742
Ala Glu Glu Gly Lys Asn Ile Leu Ala Glu Ser Gln Lys Glu Val Gly
        195                 200                 205 gag aaa acc cca ggc cag gct ggc cag gct aag atg caa ggg gac acc    790
Glu Lys Thr Pro Gly Gln Ala Gly Gln Ala Lys Met Gln Gly Asp Thr
    210                 215                 220
```

```
tcg agg ggg att gag ttc cag gct gtt ccc tca gag aaa tcc gag gtg      838
Ser Arg Gly Ile Glu Phe Gln Ala Val Pro Ser Glu Lys Ser Glu Val
225                 230                 235                 240 ggg cag gcc ctc tgt ctc aca gcc agg gag gag gac tgc ttc cag att      886
Gly Gln Ala Leu Cys Leu Thr Ala Arg Glu Glu Asp Cys Phe Gln Ile
                245                 250                 255 ttg gat gat tgc ccg cca cct ccg gcc ccc ttc cct cac cgc atg gtg      934
Leu Asp Asp Cys Pro Pro Pro Pro Ala Pro Phe Pro His Arg Met Val
            260                 265                 270 gag ctg agg acc ggg aat gtc agc agt gaa ttc agt atg aac tcc aag      982
Glu Leu Arg Thr Gly Asn Val Ser Ser Glu Phe Ser Met Asn Ser Lys
        275                 280                 285 gag gcg ctc gga ggt ggc aag ttt ggg gca gtc tgt acc tgc atg gag     1030
Glu Ala Leu Gly Gly Gly Lys Phe Gly Ala Val Cys Thr Cys Met Glu
    290                 295                 300 aaa gcc aca ggc ctc aag ctg gca gcc aag gtc atc aag aaa cag act     1078
Lys Ala Thr Gly Leu Lys Leu Ala Ala Lys Val Ile Lys Lys Gln Thr
305                 310                 315                 320 ccc aaa gac aag gaa atg gtg ttg ctg gag att gag gtc atg aac cag     1126
Pro Lys Asp Lys Glu Met Val Leu Leu Glu Ile Glu Val Met Asn Gln
                325                 330                 335 ctg aac cac cgc aat ctg atc cag ctg tat gca gcc atc gag act ccg     1174
Leu Asn His Arg Asn Leu Ile Gln Leu Tyr Ala Ala Ile Glu Thr Pro
            340                 345                 350 cat gag atc gtc ctg ttc atg gag tac atc gag ggc gga gag ctc ttc     1222
His Glu Ile Val Leu Phe Met Glu Tyr Ile Glu Gly Gly Glu Leu Phe
        355                 360                 365 gag agg att gtg gat gag gac tac cat ctg acc gag gtg gac acc atg     1270
Glu Arg Ile Val Asp Glu Asp Tyr His Leu Thr Glu Val Asp Thr Met
    370                 375                 380 gtg ttt gtc agg cag atc tgt gac ggg atc ctc ttc atg cac aag atg     1318
Val Phe Val Arg Gln Ile Cys Asp Gly Ile Leu Phe Met His Lys Met
385                 390                 395                 400 agg gtt ttg cac ctg gac ctc aag cca gag aac atc ctg tgt gtc aac     1366
Arg Val Leu His Leu Asp Leu Lys Pro Glu Asn Ile Leu Cys Val Asn
                405                 410                 415 acc acc ggg cat ttg gtg aag atc att gac ttt ggc ctg gca cgg agg     1414
Thr Thr Gly His Leu Val Lys Ile Ile Asp Phe Gly Leu Ala Arg Arg
            420                 425                 430 tat aac ccc aac gag aag ctg aag gtg aac ttt ggg acc cca gag ttc     1462
Tyr Asn Pro Asn Glu Lys Leu Lys Val Asn Phe Gly Thr Pro Glu Phe
        435                 440                 445 ctg tca cct gag gtg gtg aat tat gac caa atc tcc gat aag aca gac     1510
Leu Ser Pro Glu Val Val Asn Tyr Asp Gln Ile Ser Asp Lys Thr Asp
    450                 455                 460 atg tgg agt atg ggg gtg atc acc tac atg ctg ctg agc ggc ctc tcc     1558
Met Trp Ser Met Gly Val Ile Thr Tyr Met Leu Leu Ser Gly Leu Ser
465                 470                 475                 480 ccc ttc ctg gga gat gat gac aca gag acc cta aac aac gtt cta tct     1606
Pro Phe Leu Gly Asp Asp Asp Thr Glu Thr Leu Asn Asn Val Leu Ser
                485                 490                 495 ggc aac tgg tac ttt gat gaa gag acc ttt gag gcc gta tca gac gag     1654
Gly Asn Trp Tyr Phe Asp Glu Glu Thr Phe Glu Ala Val Ser Asp Glu
            500                 505                 510 gcc aaa gac ttt gtc tcc aac ctc atc gtc aag gac cag agg gcc cgg     1702
Ala Lys Asp Phe Val Ser Asn Leu Ile Val Lys Asp Gln Arg Ala Arg
        515                 520                 525 atg aac gct gcc cag tgt ctc gcc cat ccc tgg ctc aac aac ctg gcg     1750
Met Asn Ala Ala Gln Cys Leu Ala His Pro Trp Leu Asn Asn Leu Ala
    530                 535                 540
```

```
gag aaa gcc aaa cgc tgt aac cga cgc ctt aag tcc cag atc ttg ctt    1798
Glu Lys Ala Lys Arg Cys Asn Arg Arg Leu Lys Ser Gln Ile Leu Leu
545                 550                 555                 560 aag aaa tac ctc atg aag agg cgc tgg aag aaa aac ttc att gct gtc    1846
Lys Lys Tyr Leu Met Lys Arg Arg Trp Lys Lys Asn Phe Ile Ala Val
                565                 570                 575 agc gct gcc aac cgc ttc aag aag atc agc agc tcg ggg gca ctg atg    1894
Ser Ala Ala Asn Arg Phe Lys Lys Ile Ser Ser Ser Gly Ala Leu Met
            580                 585                 590 gct ctg ggg gtc tgagcctgg gcgcantgga aagcctggac gcagccacac         1946
Ala Leu Gly Val
            595 agtggcgggg gcttgaagcc acacagccca gaaggccaga aaaggcagcc agatccccag  2006 ggcagcctcg ttaggacaag gctgtgccaa gggctgggaa                       2046

<210> SEQ ID NO 8
<211> LENGTH: 596
<212> TYPE: PRT
<213> ORGANISM: Homo sapiens

<400> SEQUENCE: 8

Met Ala Thr Glu Asn Gly Ala Val Glu Leu Gly Ile Gln Asn Pro Ser
1               5                   10                  15

Thr Asp Lys Ala Pro Lys Gly Pro Thr Gly Glu Arg Pro Leu Ala Ala
            20                  25                  30

Gly Lys Asp Pro Gly Pro Pro Asp Pro Lys Lys Ala Pro Asp Pro Pro
        35                  40                  45

Thr Leu Lys Lys Asp Ala Lys Ala Pro Ala Ser Glu Lys Gly Asp Gly
    50                  55                  60

Thr Leu Ala Gln Pro Ser Thr Ser Ser Gln Gly Pro Lys Gly Glu Gly
65                  70                  75                  80

Asp Arg Gly Gly Gly Pro Ala Glu Gly Ser Ala Gly Pro Pro Ala Ala
                85                  90                  95

Leu Pro Gln Gln Thr Ala Thr Pro Glu Thr Ser Val Lys Pro Lys
            100                 105                 110

Ala Glu Gln Gly Ala Ser Gly Ser Gln Asp Pro Gly Lys Pro Arg Val
        115                 120                 125

Gly Lys Lys Ala Ala Glu Gly Gln Ala Ala Arg Arg Gly Ser Pro
130                 135                 140

Ala Phe Leu His Ser Pro Ser Cys Pro Ala Ile Ile Ser Ser Ser Glu
145                 150                 155                 160

Lys Leu Leu Ala Lys Lys Pro Pro Ser Glu Ala Ser Glu Leu Thr Phe
                165                 170                 175

Glu Gly Val Pro Met Thr His Ser Pro Thr Asp Pro Arg Pro Ala Lys
            180                 185                 190

Ala Glu Glu Gly Lys Asn Ile Leu Ala Glu Ser Gln Lys Glu Val Gly
        195                 200                 205

Glu Lys Thr Pro Gly Gln Ala Gly Gln Ala Lys Met Gln Gly Asp Thr
    210                 215                 220

Ser Arg Gly Ile Glu Phe Gln Ala Val Pro Ser Glu Lys Ser Glu Val
225                 230                 235                 240

Gly Gln Ala Leu Cys Leu Thr Ala Arg Glu Glu Asp Cys Phe Gln Ile
                245                 250                 255

Leu Asp Asp Cys Pro Pro Pro Ala Pro Phe Pro His Arg Met Val
            260                 265                 270
```

-continued

```
Glu Leu Arg Thr Gly Asn Val Ser Ser Glu Phe Ser Met Asn Ser Lys
            275                 280                 285
Glu Ala Leu Gly Gly Gly Lys Phe Gly Ala Val Cys Thr Cys Met Glu
        290                 295                 300
Lys Ala Thr Gly Leu Lys Leu Ala Ala Lys Val Ile Lys Lys Gln Thr
305                 310                 315                 320
Pro Lys Asp Lys Glu Met Val Leu Leu Glu Ile Glu Val Met Asn Gln
                325                 330                 335
Leu Asn His Arg Asn Leu Ile Gln Leu Tyr Ala Ala Ile Glu Thr Pro
            340                 345                 350
His Glu Ile Val Leu Phe Met Glu Tyr Ile Glu Gly Gly Glu Leu Phe
        355                 360                 365
Glu Arg Ile Val Asp Glu Asp Tyr His Leu Thr Glu Val Asp Thr Met
370                 375                 380
Val Phe Val Arg Gln Ile Cys Asp Gly Ile Leu Phe Met His Lys Met
385                 390                 395                 400
Arg Val Leu His Leu Asp Leu Lys Pro Glu Asn Ile Leu Cys Val Asn
                405                 410                 415
Thr Thr Gly His Leu Val Lys Ile Ile Asp Phe Gly Leu Ala Arg Arg
            420                 425                 430
Tyr Asn Pro Asn Glu Lys Leu Lys Val Asn Phe Gly Thr Pro Glu Phe
        435                 440                 445
Leu Ser Pro Glu Val Val Asn Tyr Asp Gln Ile Ser Asp Lys Thr Asp
    450                 455                 460
Met Trp Ser Met Gly Val Ile Thr Tyr Met Leu Leu Ser Gly Leu Ser
465                 470                 475                 480
Pro Phe Leu Gly Asp Asp Asp Thr Glu Thr Leu Asn Asn Val Leu Ser
                485                 490                 495
Gly Asn Trp Tyr Phe Asp Glu Glu Thr Phe Glu Ala Val Ser Asp Glu
            500                 505                 510
Ala Lys Asp Phe Val Ser Asn Leu Ile Val Lys Asp Gln Arg Ala Arg
        515                 520                 525
Met Asn Ala Ala Gln Cys Leu Ala His Pro Trp Leu Asn Asn Leu Ala
    530                 535                 540
Glu Lys Ala Lys Arg Cys Asn Arg Arg Leu Lys Ser Gln Ile Leu Leu
545                 550                 555                 560
Lys Lys Tyr Leu Met Lys Arg Arg Trp Lys Lys Asn Phe Ile Ala Val
                565                 570                 575
Ser Ala Ala Asn Arg Phe Lys Lys Ile Ser Ser Ser Gly Ala Leu Met
            580                 585                 590
Ala Leu Gly Val
        595
```

<210> SEQ ID NO 9
<211> LENGTH: 1788
<212> TYPE: DNA
<213> ORGANISM: Homo sapiens

<400> SEQUENCE: 9

```
atggcgacag aaaatggagc agttgagctg ggaattcaga acccatcaac agacaaggca    60
cctaaaggtc ccacaggtga agacccctg gctgcaggga agaccctgg ccccccagac    120
ccaaagaaag ctccggatcc acccaccctg aagaaagatg ccaaagcccc tgcctcagag    180
aaagggggatg gtaccctggc ccaaccctca actagcagcc aaggccccaa aggagagggt    240
```

```
gacaggggcg gggggcccgc ggagggcagt gctgggcccc cggcagccct gccccagcag    300
actgcgacac ctgagaccag cgtcaagaag cccaaggctg agcagggagc ctcaggcagc    360
caggatcctg gaaagcccag ggtgggcaag aaggcagcag agggccaagc agcagccagg    420
aggggctcac ctgcctttct gcatagcccc agctgtcctg ccatcatctc cagttctgag    480
aagctgctgg ccaagaagcc cccaagcgag gcatcagagc tcacctttga aggggtgccc    540
atgacccaca gccccacgga tcccaggcca gccaaggcag aagaaggaaa gaacatcctg    600
gcagagagcc agaaggaagt gggagagaaa accccaggcc aggctggcca ggctaagatg    660 caagggggaca cctcgagggg gattgagttc caggctgttc cctcagagaa atccgaggtg    720
gggcaggccc tctgtctcac agccagggag gaggactgct tccagatttt ggatgattgc    780
ccgccacctc cggcccccctt ccctcaccgc atggtggagc tgaggaccgg aatgtcagc    840 agtgaattca gtatgaactc caaggaggcg ctcggaggtg gcaagtttgg ggcagtctgt    900
acctgcatgg agaaagccac aggcctcaag ctggcagcca aggtcatcaa gaaacagact    960
cccaaagaca aggaaatggt gttgctggag attgaggtca tgaaccagct gaaccaccgc   1020
aatctgatcc agctgtatgc agccatcgag actccgcatg agatcgtcct gttcatggag   1080
tacatcgagg gcggagagct cttcgagagg attgtggatg aggactacca tctgaccgag   1140
gtggacacca tggtgtttgt caggcagatc tgtgacggga tcctcttcat gcacaagatg   1200 aggttttgc acctggacct caagccagag aacatcctgt gtgtcaacac caccgggcat   1260
ttggtgaaga tcattgactt tggcctggca cggaggtata accccaacga gaagctgaag   1320
gtgaactttg gaccccccaga gttcctgtca cctgaggtgg tgaattatga ccaaatctcc   1380
gataagacag acatgtggag tatgggggtg atcacctaca tgctgctgag cggcctctcc   1440
cccttcctgg gagatgatga cacagagacc ctaaacaacg ttctatctgg caactggtac   1500
tttgatgaag agacctttga ggccgtatca gacgaggcca aagctttgt ctccaacctc   1560 atcgtcaagg accagagggc ccggatgaac gctgcccagt gtctcgccca tccctggctc   1620
aacaacctgg cggagaaagc caaacgctgt aaccgacgcc ttaagtccca gatcttgctt   1680
aagaaatacc tcatgaagag gcgctggaag aaaaacttca ttgctgtcag cgctgccaac   1740
cgcttcaaga agatcagcag ctcgggggca ctgatggctc tgggggtc              1788
```

<210> SEQ ID NO 10
<211> LENGTH: 265
<212> TYPE: PRT
<213> ORGANISM: Artificial Sequence
<220> FEATURE:
<223> OTHER INFORMATION: consensus sequence

<400> SEQUENCE: 10

```
Lys Val Tyr Lys Ala Lys His Lys Thr Gly Lys Ile Val Ala Val Lys
 1               5                  10                  15

Ile Leu Lys Lys Glu Ser Leu Ser Leu Arg Glu Ile Gln Ile Leu Lys
            20                  25                  30

Arg Leu Ser His Pro Asn Ile Val Arg Leu Leu Gly Val Phe Glu Asp
        35                  40                  45

Thr Asp Asp His Leu Tyr Leu Val Met Glu Tyr Met Glu Gly Gly Asp
    50                  55                  60

Leu Phe Asp Tyr Leu Arg Arg Asn Gly Pro Leu Ser Glu Lys Glu Ala
65                  70                  75                  80

Lys Lys Ile Ala Leu Gln Ile Leu Arg Gly Leu Glu Tyr Leu His Ser
```

-continued

```
                    85                  90                  95
Asn Gly Ile Val His Arg Asp Leu Lys Pro Glu Asn Ile Leu Leu Asp
                100                 105                 110
Glu Asn Gly Thr Val Lys Ile Ala Asp Phe Gly Leu Ala Arg Leu Leu
            115                 120                 125
Glu Lys Leu Thr Thr Phe Val Gly Thr Pro Trp Tyr Met Met Ala Pro
        130                 135                 140
Glu Val Ile Leu Glu Gly Arg Gly Tyr Ser Ser Lys Val Asp Val Trp
145                 150                 155                 160
Ser Leu Gly Val Ile Leu Tyr Glu Leu Leu Thr Gly Pro Leu Phe
                165                 170                 175
Pro Gly Ala Asp Leu Pro Ala Phe Thr Gly Gly Asp Glu Val Asp Gln
            180                 185                 190
Leu Ile Ile Phe Val Leu Lys Leu Pro Phe Ser Asp Glu Leu Pro Lys
        195                 200                 205
Thr Arg Ile Asp Pro Leu Glu Glu Leu Phe Arg Ile Lys Lys Arg Arg
    210                 215                 220
Leu Pro Leu Pro Ser Asn Cys Ser Glu Glu Leu Lys Asp Leu Leu Lys
225                 230                 235                 240
Lys Cys Leu Asn Lys Asp Pro Ser Lys Arg Pro Gly Ser Ala Thr Ala
                245                 250                 255
Lys Glu Ile Leu Asn His Pro Trp Phe
            260                 265

<210> SEQ ID NO 11
<211> LENGTH: 230
<212> TYPE: PRT
<213> ORGANISM: Artificial Sequence
<220> FEATURE:
<223> OTHER INFORMATION: consensus sequence

<400> SEQUENCE: 11

Tyr Glu Leu Leu Lys Lys Leu Gly Lys Gly Ala Phe Gly Lys Val Tyr
1               5                   10                  15
Leu Ala Arg Asp Lys Lys Thr Gly Arg Leu Val Ala Ile Lys Val Ile
            20                  25                  30
Lys Glu Arg Ile Leu Arg Glu Ile Lys Ile Leu Lys Lys Asp His Pro
        35                  40                  45
Asn Ile Val Lys Leu Tyr Asp Val Phe Glu Asp Lys Leu Tyr Leu
    50                  55                  60
Val Met Glu Tyr Cys Glu Gly Asp Leu Gly Asp Leu Phe Asp Leu Leu
65                  70                  75                  80
Lys Lys Arg Gly Arg Gly Leu Arg Lys Val Leu Ser Glu Glu Ala
                85                  90                  95
Arg Phe Tyr Phe Arg Gln Ile Leu Ser Ala Leu Glu Tyr Leu His Ser
            100                 105                 110
Gln Gly Ile Ile His Arg Asp Leu Lys Pro Glu Asn Ile Leu Leu Asp
        115                 120                 125
Ser Val Lys Leu Ala Asp Phe Gly Leu Ala Arg Gln Leu Thr Thr Phe
    130                 135                 140
Val Gly Thr Pro Glu Tyr Met Ala Pro Glu Val Leu Gly Tyr Gly Lys
145                 150                 155                 160
Pro Ala Val Asp Ile Trp Ser Leu Gly Cys Ile Leu Tyr Glu Leu Leu
                165                 170                 175
Thr Gly Lys Pro Pro Phe Pro Gln Leu Asp Leu Ile Phe Lys Lys Ile
```

```
                    180                 185                 190
Gly Ser Pro Glu Ala Lys Asp Leu Ile Lys Lys Leu Leu Val Lys Asp
        195                 200                 205
Pro Glu Lys Arg Leu Thr Ala Glu Ala Leu Glu Asp Glu Leu Asp Ile
    210                 215                 220
Lys Ala His Pro Phe Phe
225                 230

<210> SEQ ID NO 12
<211> LENGTH: 239
<212> TYPE: PRT
<213> ORGANISM: Artificial Sequence
<220> FEATURE:
<223> OTHER INFORMATION: consensus sequence

<400> SEQUENCE: 12

Tyr Glu Leu Leu Glu Lys Leu Gly Glu Gly Ser Phe Gly Lys Val Tyr
1               5                   10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
        35                  40                  45

His Pro Asn Ile Val Arg Leu Leu Gly Val Phe Glu Asp Thr Asp Asp
    50                  55                  60

His Leu Tyr Leu Val Met Glu Tyr Met Glu Gly Gly Asp Leu Phe Asp
65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
    130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Arg Leu Pro
225                 230                 235

<210> SEQ ID NO 13
<211> LENGTH: 278
<212> TYPE: PRT
<213> ORGANISM: Artificial Sequence
<220> FEATURE:
<223> OTHER INFORMATION: consensus sequence

<400> SEQUENCE: 13

Tyr Glu Leu Leu Glu Lys Leu Gly Glu Gly Ser Phe Gly Lys Val Tyr
1               5                   10                  15
```

-continued

```
Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
            35                  40                  45

His Pro Asn Ile Val Arg Leu Leu Gly Val Phe Glu Asp Thr Asp Asp
        50                  55                  60

His Leu Tyr Leu Val Met Glu Tyr Met Glu Gly Gly Asp Leu Phe Asp
 65             70                  75                      80

Tyr Leu Arg Arg Asn Gly Pro Leu Ser Glu Lys Glu Ala Lys Lys Ile
            85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
            115                 120                 125

Thr Val Lys Ile Ala Asp Phe Gly Leu Ala Arg Leu Leu Glu Lys Leu
            130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
            165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
            195                 200                 205

Phe Val Leu Lys Leu Pro Phe Ser Asp Glu Leu Pro Lys Thr Arg Ile
            210                 215                 220

Asp Pro Leu Glu Glu Leu Phe Arg Ile Lys Lys Arg Arg Leu Pro Leu
225                 230                 235                 240

Pro Ser Asn Cys Ser Glu Glu Leu Lys Asp Leu Leu Lys Lys Cys Leu
            245                 250                 255

Asn Lys Asp Pro Ser Lys Arg Pro Gly Ser Ala Thr Ala Lys Glu Ile
            260                 265                 270

Leu Asn His Pro Trp Phe
            275
```

US 6,730,491 B2

2504, 15977, AND 14760, NOVEL PROTEIN KINASE FAMILY MEMBERS AND USES THEREFOR

RELATED APPLICATIONS

This application claims priority to U.S. provisional application number 60/186,061 filed on Feb. 29, 2000, the contents of which are incorporated herein by reference.

BACKGROUND OF THE INVENTION

Phosphate tightly associated with protein has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated proteins implies the existence of one or more protein kinases capable of phosphorylating amino acid residues on proteins, and also of protein phosphatases capable of hydrolyzing phosphorylated amino acid residues on proteins.

Protein kinases play critical roles in the regulation of biochemical and morphological changes associated with cellular growth and division (D'Urso, G. et al. (1990) *Science* 250: 786–791; Birchmeier. C. et al. (1993) *Bioessays* 15: 185–189). They serve as growth factor receptors and signal transducers and have been implicated in cellular transformation and malignancy (Hunter, T. et al. (1992) *Cell* 70: 375–387; Posada, J. et al. (1992) *Mol. Biol. Cell* 3: 583–592; Hunter, T. et al. (1994) *Cell* 79: 573–582). For example, protein kinases have been shown to participate in the transmission of signals from growth-factor receptors (Sturgill, T. W. et al. (1988) *Nature* 344: 715–718; Gomez, N. et al. (1991) *Nature* 353: 170–173), control of entry of cells into mitosis (Nurse, P. (1990) *Nature* 344: 503–508; Maller, J. L. (1991) *Curr. Opin. Cell Biol.* 3: 269–275) and regulation of actin bundling (Husain-Chishti, A. et al. (1988) *Nature* 334: 718–721). Protein kinases can be divided into two main groups based on either amino acid sequence similarity or specificity for either serine/threonine or tyrosine residues. A small number of dual-specificity kinases are structurally like the serine/threonine-specific group. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks, S. K. et al. (1988) *Science* 241: 42–52).

SUMMARY OF THE INVENTION

The present invention is based, in part, on the discovery of novel protein kinase family members, referred to herein as "2504, 15977, and 14760". The nucleotide sequence of a cDNA encoding 2504 is shown in SEQ ID NO:1, and the amino acid sequence of a 2504 polypeptide is shown in SEQ ID NO:2. In addition, the nucleotide sequences of the coding region are depicted in SEQ ID NO:3. The nucleotide sequence of a cDNA encoding 15977 is shown in SEQ ID NO:4, and the amino acid sequence of a 15977 polypeptide is shown in SEQ ID NO:5. In addition, the nucleotide sequences of the coding region are depicted in SEQ ID NO:6. The nucleotide sequence of a cDNA encoding 14760 is shown in SEQ ID NO:7, and the amino acid sequence of a 14760 polypeptide is shown in SEQ ID NO:8. In addition, the nucleotide sequences of the coding region are depicted in SEQ ID NO:9.

Accordingly, in one aspect, the invention features a nucleic acid molecule which encodes a 2504, 15977, or 14760 protein or polypeptide, e.g., a biologically active portion of the 2504, 15977, or 14760 protein. In a preferred embodiment the isolated nucleic acid molecule encodes a polypeptide having the amino acid sequence of SEQ ID NO:2, SEQ ID NO:5, or SEQ ID NO:8. In other embodiments, the invention provides isolated 2504, 15977, or 14760 nucleic acid molecules having the nucleotide sequence shown in SEQ ID NO:1, SEQ ID NO:3, SEQ ID NO:4, SEQ ID NO:6, SEQ ID NO:7, SEQ ID NO:9, or the sequence of the DNA insert of the plasmid deposited with ATCC Accession Number 1843. In still other embodiments, the invention provides nucleic acid molecules that are substantially identical (e.g., naturally occurring allelic variants) to the nucleotide sequence shown in SEQ ID NO:1, SEQ ID NO:3, SEQ ID NO:4, SEQ ID NO:6, SEQ ID NO:7, SEQ ID NO:9, or the sequence of the DNA insert of the plasmid deposited with ATCC Accession Number 1843. In other embodiments, the invention provides a nucleic acid molecule which hybridizes under a stringent hybridization condition described herein to a nucleic acid molecule comprising the nucleotide sequence of SEQ ID NO:1, SEQ ID NO:3, SEQ ID NO:4, SEQ ID NO:6, SEQ ID NO:7, SEQ ID NO:9, or the sequence of the DNA insert of the plasmid deposited with ATCC Accession Number 1843. wherein the nucleic acid encodes a full length 2504, 15977, or 14760 protein or an active fragment thereof.

In a related aspect, the invention further provides nucleic acid constructs which include a 2504, 15977, or 14760 nucleic acid molecule described herein. In certain embodiments, the nucleic acid molecules of the invention are operatively linked to native or heterologous regulatory sequences. Also included, are vectors and host cells containing the 2504, 15977, or 14760 nucleic acid molecules of the invention e.g., vectors and host cells suitable for producing 2504, 15977, or 14760 nucleic acid molecules and polypeptides.

In another related aspect, the invention provides nucleic acid fragments suitable as primers or hybridization probes for the detection of 2504, 15977, or 14760-encoding nucleic acids.

In still another related aspect, isolated nucleic acid molecules that are antisense to a 2504, 15977, or 14760 encoding nucleic acid molecule are provided.

In another aspect, the invention features, 2504, 15977, or 14760 polypeptides, and biologically active or antigenic fragments thereof that are useful, e.g., as reagents or targets in assays applicable to treatment and diagnosis of 2504, 15977, or 14760 mediated or related disorders. In another embodiment, the invention provides 2504, 15977, or 14760 polypeptides having a 2504, 15977, or 14760 activity. Preferred polypeptides are 2504, 15977, or 14760 proteins including at least one protein kinase domain, e.g. a serine/threonine kinase domain, and, preferably, having a 2504, 15977, or 14760 activity, e.g., a 2504, 15977, or 14760 activity as described herein.

In other embodiments, the invention provides 2504, 15977, or 14760 polypeptides, e.g., a 2504, 15977, or 14760 polypeptide having the amino acid sequence shown in SEQ ID NO:2, SEQ ID NO:5, or SEQ ID NO:8; the amino acid sequence encoded by the cDNA insert of the plasmid deposited with ATCC Accession Number 1843; an amino acid sequence that is substantially identical to the amino acid sequence shown in SEQ ID NO:2, SEQ ID NO:5, or SEQ ID NO:8; or an amino acid sequence encoded by a nucleic acid molecule having a nucleotide sequence which hybridizes under a stringent hybridization condition described herein to a nucleic acid molecule comprising the nucleotide sequence of SEQ ID NO:1, SEQ ID NO:3, SEQ ID NO:4, SEQ ID NO:6, SEQ ID NO:7, SEQ ID NO:9, or the sequence of the DNA insert of the plasmid deposited with ATCC Accession Number 1843, wherein the nucleic acid encodes a full length 2504, 15977, or 14760 protein or an active fragment thereof.

In a related aspect, the invention further provides nucleic acid constructs which include a 2504, 15977, or 14760 nucleic acid molecule described herein.

In a related aspect, the invention provides 2504, 15977, or 14760 polypeptides or fragments operatively linked to non-2504, 15977, or 14760 polypeptides to form fusion proteins.

In another aspect, the invention features antibodies and antigen-binding fragments thereof, that react with, or more preferably specifically bind 2504, 15977, or 14760 polypeptides.

In another aspect, the invention provides methods of screening for compounds that modulate the expression or activity of the 2504, 15977, or 14760 polypeptides or nucleic acids.

In still another aspect, the invention features a method of modulating (e.g., enhancing or inhibiting) the proliferation, survival, and/or differentiation of a cell, e.g., a 2504-, 15977-, or a 14760-expressing cell, e.g., a neural cell (e.g., a brain or glial cell), a cardiovascular cell (e.g., a heart or blood vessel cell, e.g., a smooth muscle cell), a liver cell, a hematopoietic cell (e.g., a bone marrow cell such as a glycophorin-positive cell). The method includes contacting the cell with an agent (e.g., a screened compound) that modulates the activity or expression of a 2504-, 15977-, or a 14760 polypeptide or nucleic acid, in an amount effective to modulate the proliferation and/or differentiation of the cell.

In a preferred embodiment, the 2504-, 15977-, or a 14760 polypeptide has an amino acid sequence identical to, or substantially identical to, SEQ ID NO:2, 5 or 8. In other embodiments, the 2504-, 15977-, or a 14760 polypeptide is a fragment of at least 15, 20, 50, 100, 150, or more contiguous amino acids of SEQ ID NO:2, 5 or 8.

In a preferred embodiment, the 2504-, 15977-, or a 14760 nucleic acid has a nucleotide sequence identical to, or substantially identical to, SEQ ID NO:1, 3, 4, 6, 7, or 9. In other embodiments, the 2504-, 15977-, or a 14760 nucleic acid is a fragment of at least 50, 100, 150, 200, 250, 300, 350, 400, 450, 500, or more contiguous nucleotides of SEQ ID NO:1, 3, 4, 6, 7, or 9.

In a preferred embodiment, the agent modulates (e.g., increases or decreases) protein kinase activity.

In a preferred embodiment, the agent modulates (e.g., increases or decreases) expression of the 2504-, 15977-, or a 14760 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or a 2504-, 15977-, or 14760 nucleic acid, or any combination thereof.

In a preferred embodiment, the agent is administered in combination with a cytotoxic agent.

In a preferred embodiment, the cell, e.g., the 2504-, 15977-, or a 14760-expressing cell, is a neural cell (e.g., a neuronal or glial cell), a cardiovascular cell (e.g., a heart or blood vessel cell, e.g., a smooth muscle cell), a liver cell, a hematopoietic cell, e.g., a myeloid, lymphoid or erythroid cell, or a precursor cell thereof. Examples of such cells include myelocytic cells (polymorphonuclear cells), erythrocytic cells, lymphocytes, monocytes, reticular cells, plasma cells and megakaryocytes, as well as stem cells for the different lineages, and precursors for the committed progenitor cells, for example, precursors of blood cells (e.g., red blood cells, such as erythroblasts), macrophages (monoblasts), platelets (megakaryocytes), polymorphonuclear leucocytes (myeloblasts), and lymphocytes (lymphoblasts).

In a preferred embodiment, the cell, e.g., the 14760-expressing cell, is a bone marrow erythroid cell, e.g., an erythroid progenitor (e.g., a glycophorin A expressing cell) or a differentiated cell, e.g., an erythrocyte or a megakaryocyte.

In a preferred embodiment, the cell, e.g., the 2504-, 15977-, or a 14760-expressing cell, is further contacted with a protein, e.g., a cytokine or a hormone. Exemplary proteins include, but are not limited to, G-CSF, GM-CSF, stem cell factor, interleukin-3 (IL-3), IL-4, Flt-3 ligand, thrombopoietin, and erythropoietin. Most preferably, the protein is erythropoietin. The protein contacting step can occur before, at the same time, or after the agent is contacted. The protein contacting step can be effected in vitro or ex vivo. For example, the cell, e.g., the 14760-expressing cell is obtained from a subject, e.g., a patient, and contacted with the protein ex vivo. The treated cell can be re-introduced into the subject. Alternatively, the protein contacting step can occur in vivo.

In a preferred embodiment, the agent and the 2504-, 15977-, or a 14760-polypeptide or nucleic acid are contacted in vitro or ex vivo.

In a preferred embodiment, the contacting step is effected in vivo in a subject, e.g., as part of a therapeutic or prophylactic protocol. Preferably, the subject is a human, e.g., a patient with an immune, cardiovascular, proliferative, or liver disorder. In other embodiments, the subject is a non-human animal, e.g., an experimental animal.

The contacting step(s) can be repeated.

In a preferred embodiment, the agent decreases the proliferation and/or enhances the differentiation of the cell, e.g., the 2504-, 15977-, or a 14760-expressing cell. Such agents can be used to treat or prevent cancers, e.g., leukemic cancers such as erythroid leukemias, or carcinomas, In preferred embodiments, the methods involve treatment or prevention of disorder related to aberrant activity or expression of the 2504, 15977, or 14760 polypeptides or nucleic acids, such as conditions involving aberrant or deficient cellular proliferation or differentiation, neural disorders, immune disorders, cardiovascular disorders, liver, skin, and skeletal muscle disorders, among others. The method includes administering to the subject an effective amount of an agent that modulates the activity or expression of a 2504, 15977, and 14760 polypeptide or nucleic acid such that the disorder is ameliorated or prevented.

In a preferred embodiment, the 2504, 15977, and 14760 polypeptide has an amino acid sequence identical to, or substantially identical to, SEQ ID NO:2, 5 or 8. In other embodiments, the 2504, 15977, and 14760 polypeptide is a fragment of at least 15, 20, 50, 100, 150, or more contiguous amino acids of SEQ ID NO:2, 5 or 8.

In a preferred embodiment, the 2504, 15977, and 14760 nucleic acid has a nucleotide sequence identical to, or substantially identical to, SEQ ID NO:1, 3, 4, 6, 7 or 9. In other embodiments, the 2504-, 15977-, or a 14760 nucleic acid is a fragment of at least 50, 100, 150, 200, 250, 300, 350, 400, 450, 500, or more contiguous nucleotides of SEQ ID NO:1, 3, 4, 6, 7 or 9.

In a preferred embodiment, the agent modulates (e.g., increases or decreases) protein kinase activity.

In a preferred embodiment, the agent modulates (e.g., increases or decreases) expression of the 2504, 15977, and 14760 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or a 2504, 15977, and 14760 nucleic acid, or any combination thereof.

In a preferred embodiment, the agent is administered in combination with a cytotoxic agent.

In a preferred embodiment, the subject is a human, e.g., a patient with a disorder described herein. In other embodiments, the subject is a non-human animal, e.g., an experimental animal.

In a preferred embodiment, the agent decreases the proliferation and/or enhances the differentiation of a cell, e.g., a 2504, 15977, and 14760-expressing cell, e.g., a hematopoietic cell, in the subject. Such agents can be used to treat or prevent cancers, e.g., leukemic cancers such as erythroid leukemias, or carcinomas.

In a preferred embodiment, the disorder is an immune disorder, a cardiovascular disorder, a neural disorder, a liver disorder, among others.

The administration of the agent and/or protein can be repeated.

The invention also provides assays for determining the activity of or the presence or absence of 2504, 15977, or 14760 polypeptides or nucleic acid molecules in a biological sample, including for disease diagnosis.

In further aspect the invention provides assays for determining the presence or absence of a genetic alteration in a 2504, 15977, or 14760 polypeptide or nucleic acid molecule, including for disease diagnosis.

The invention also features a method of diagnosing, or staging, a disorder, e.g., a disorder as described herein, in a subject. The method includes evaluating the expression or activity of a 2504, 15977, and 14760 nucleic acid, or a 2504, 15977, and 14760 polypeptide, such that, a difference in the level of 2504, 15977, and 14760 nucleic acid, or 2504, 15977, and 14760 polypeptide relative to a normal subject or a cohort of normal subjects is indicative of the disorder, or a stage in the disorder.

In a preferred embodiment, the subject is a human.

In a preferred embodiment, the evaluating step occurs in vitro or ex vivo. For example, a sample, e.g., a blood sample or biopsy, is obtained from the subject.

In a preferred embodiment, the evaluating step occurs in vivo. For example, by administering to the subject a detectably labeled agent that interacts with the 2504, 15977, and 14760 nucleic acid or polypeptide, such that a signal is generated relative to the level of activity or expression of the 2504, 15977, and 14760 nucleic acid or polypeptide.

In still another aspect, the invention features a method for evaluating the efficacy of a treatment of a disorder (e.g., a disorder as described herein), in a subject. The method includes treating a subject with a protocol under evaluation; assessing the expression of a 2504, 15977, or 14760 nucleic acid, or 2504, 15977, or 14760 polypeptide, such that a change in the level of the 2504, 15977, or 14760 nucleic acid, or the 2504, 15977, or 14760 polypeptide after treatment, relative to the level before treatment, is indicative of the efficacy of the treatment of the disorder.

In yet another aspect, the invention features a method for identifying an agent, e.g., a compound, which modulates the activity or expression of a 2504, 15977, and 14760 polypeptide, e.g., a 2504, 15977, and 14760 polypeptide as described herein, or a 2504, 15977, and 14760 nucleic acid, e.g., a 2504, 15977, and 14760 nucleic acid as described herein. The method includes contacting the 2504, 15977, and 14760 polypeptide or nucleic acid with a test agent (e.g., a test compound); and determining the effect of the test compound on the activity of the polypeptide or nucleic acid to thereby identify a compound which modulates the activity of the polypeptide or nucleic acid.

In a preferred embodiment, the activity of the 2504, 15977, and 14760 polypeptide is a protein kinase activity.

In a preferred embodiment, the activity of the 2504, 15977, and 14760 polypeptide is proliferation, differentiation, and/or survival of a cell, e.g., a 2504, 15977, and 14760-expressing cell, e.g., a neural cell, a cardiovascular cell, a hematopoietic cell (e.g., a bone marrow cell such as a glycophorin-positive cell, an erythroid cell, a megakaryocyte).

In preferred embodiments, the agent is a peptide, a phosphopeptide, a small molecule, e.g., a member of a combinatorial library, or an antibody, or any combination thereof.

In additional preferred embodiments, the agent is an antisense, a ribozyme, or a triple helix molecule, or an 2504, 15977, and 14760 nucleic acid, or any combination thereof.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 2504, 15977, and 14760 molecule. In one embodiment, the capture probe is a nucleic acid, e.g., a probe complementary to a 2504, 15977, and 14760 nucleic acid sequence. In another embodiment, the capture probe is a polypeptide, e.g., an antibody specific for 2504, 15977, and 14760 polypeptides. Also featured is a method of analyzing a sample by contacting the sample to the aforementioned array and detecting binding of the sample to the array.

BRIEF DESCRIPTION OF THE DRAWINGS

FIGS. 1A–1B depict the cDNA sequence (SEQ ID NO:1) and predicted amino acid sequence (SEQ ID NO:2) of human 2504. The methionine-initiated open reading frame of human 2504 (without the 5' and 3' untranslated regions) extends from nucleotide position 154 to position 1656 of SEQ ID NO:1 (coding sequence shown in SEQ ID NO:3).

FIG. 3A depicts an alignment of the eukaryotic protein kinase domain of human 2504 with a consensus amino acid sequence derived from a hidden Markov model. The upper sequence is the consensus amino acid sequence (SEQ ID NO:10), while the lower amino acid sequence corresponds to amino acids 37 to 286 of SEQ ID NO:2.

FIG. 3B depicts an alignment of the serine/threonine kinase domain of human 2504 with a consensus amino acid sequence derived from a hidden Markov model. The upper sequence is the consensus amino acid sequence (SEQ ID NO:11), while the lower amino acid sequence corresponds to amino acids 24 to 286 of SEQ ID NO:2.

FIGS. 4A–4C depict the cDNA sequence (SEQ ID NO:4) and predicted amino acid sequence (SEQ ID NO:5) of human 15977. The methionine-initiated open reading frame of human 15977 (without the 5' and 3' untranslated regions) extends from nucleotide position 337 to position 1713 of SEQ ID NO:4 (coding sequence shown in SEQ ID NO:6).

FIG. 6A depicts an alignment of the eukaryotic protein kinase domain of human 15977 with a consensus amino acid sequence derived from a hidden Markov model. The upper sequence is the consensus amino acid sequence (SEQ ID NO:12), while the lower amino acid sequence corresponds to amino acids 44 to 276 of SEQ ID NO:5.

FIG. 6B depicts an alignment of the serine/threonine kinase domain of human 15977 with a consensus amino acid sequence derived from a hidden Markov model. The upper sequence is the consensus amino acid sequence (SEQ ID NO:11), while the lower amino acid sequence corresponds to amino acids 44 to 329 of SEQ ID NO:5.

FIGS. 7A–7B depict the cDNA sequence (SEQ ID NO:7) and predicted amino acid sequence (SEQ ID NO:8) of human 14760. The methionine-initiated open reading frame of human 14760 (without the 5' and 3' untranslated regions) extends from nucleotide position 119 to position 1906 of SEQ ID NO:7 (coding sequence shown in SEQ ID NO:9).

FIG. 9A depicts an alignment of the eukaryotic protein kinase domain of human 14760 with a consensus amino acid sequence derived from a hidden Markov model. The upper sequence is the consensus amino acid sequence (SEQ ID NO:13), while the lower amino acid sequence corresponds to amino acids 285 to 540 of SEQ ID NO:8.

FIG. 9B depicts an alignment of the serine/threonine kinase domain of human 14760 with a consensus amino acid sequence derived from a hidden Markov model. The upper sequence is the consensus amino acid sequence (SEQ ID NO:11), while the lower amino acid sequence corresponds to amino acids 285 to 540 of SEQ ID NO:8.

FIG. 11 is a bar graph depicting relative 15977 mRNA expression as determined by TaqMan assays on mRNA derived from the following human tissues. Columns are numbered at five-column intervals at the bottom of the Figure (i.e., columns 1–46), and correspond to the following: (1) Aorta/normal; (2) Fetal heart/normal; (3) Heart normal; (4) Heart/congestive heart failure (CHF); (5) Vein/Normal; (6) Smooth muscle cells (SMC) (Aortic); (7) Spinal cord/Normal; (8) Brain cortex/Normal; (9) Brain hypothalamus/Normal; (10) Glial cells (Astrocytes); (11) Brain/Glioblastoma; (12) Breast/Normal; (13) Breast tumor/(invasive carcinoma (IDC); (14) Ovary/Normal; (15) Ovary/Tumor; (16) Pancreas; (17) Prostate/Normal; (18) Prostate/Tumor; (19) Colon/normal; (20) Colon/tumor; (21) Colon/IBD; (22) Kidney/normal; (23) Liver/normal; (24) Liver fibrosis; (25) Fetal Liver/normal; (26) Lung/normal; (27) Lung/tumor; (28) Lung/COPD; (29) Spleen/normal; (30) Tonsil/normal; (31) Lymph node/normal; (32) Thymus/normal; (33) Epithelial Cells (prostate); (34) Endothelial Cells (aortic); (35) Skeletal Muscle/Normal; (36) Fibroblasts (Dermal); (37) Skin/normal; (38) Adipose/Normal; (39) Osteoblasts (primary); (40) Osteoblasts (undifferentiated); (41) Osteoblasts (Diff); (42) Osteoclasts; (43) Aortic smooth muscle cells (SMC) Early; (44) Aortic SMC Late; (45) Shear human umbilical vein endothelial cells (HUVEC); and (46) Static HUVEC. Elevated 15977 mRNA expression was observed in epithelial cells, astrocytes (glial cells), normal brain (e.g., cortex and hypothalamus), HUVEC, and normal fetal liver.

DETAILED DESCRIPTION OF THE INVENTION

Human 2504

Figure 2:
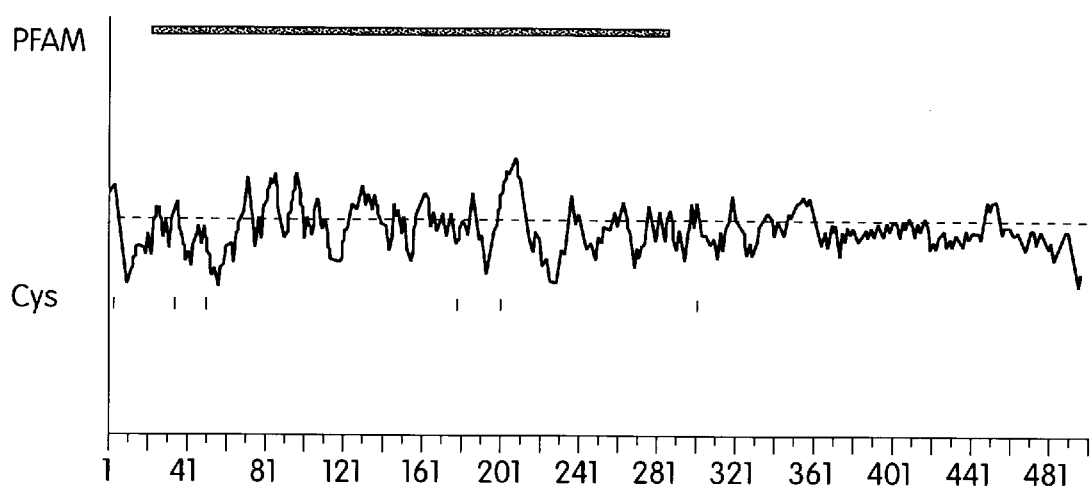
FIG. 2 depicts a hydropathy plot of human 2504. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 2504 are indicated.
Figure 5:
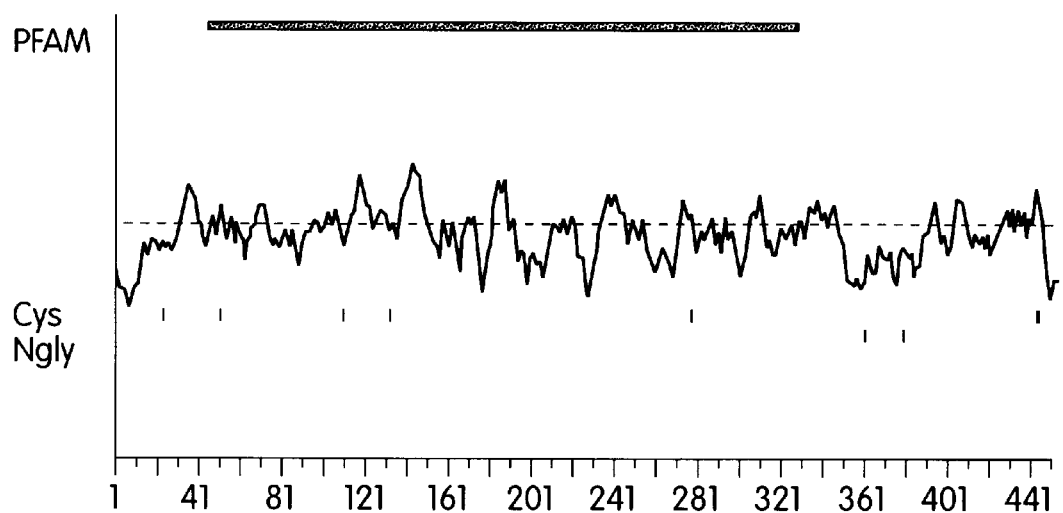
FIG. 5 depicts a hydropathy plot of human 15977. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 15977 are indicated.
Figure 8:
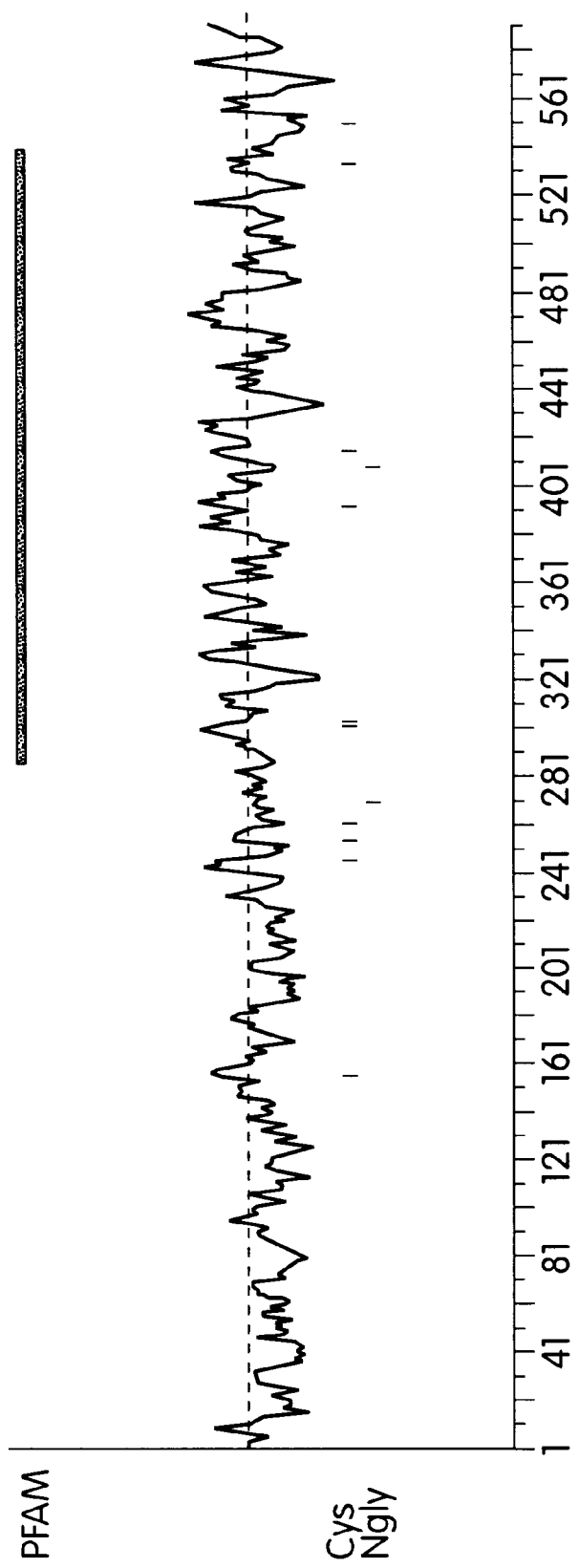
FIG. 8 depicts a hydropathy plot of human 14760. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 14760 are indicated.

The human 2504 sequence (FIGS. 1A–1B; SEQ ID NO:1), which is approximately 2297 nucleotides long including untranslated regions, contains a predicted methionine-initiated coding sequence of about 1503 nucleotides (nucleotides 154–1656 of SEQ ID NO:1; SEQ ID NO:3). The coding sequence encodes a 501 amino acid protein (SEQ ID NO:2).

This mature protein form is approximately 501 amino acid residues in length (from about amino acid 1 to amino acid 501 of SEQ ID NO:2). Human 2504 contains the following regions or other structural features (FIGS. 3A and 3B): a eukaryotic protein kinase domain (PFAM Accession PF00069) located at about amino acid residues 37 to 286 of SEQ ID NO:2; and a serine/threonine kinase domain located at about amino acid residues 24 to 286 of SEQ ID NO:2.

The 2504 protein also includes the following domains: 12 predicted Protein Kinase C phosphorylation sites (PS00005) located at about amino acids 21 to 23, 46–48, 51–53, 91–93, 103–105, 118–120, 138–140, 292–294, 422–424, 482–484, and 495–497 of SEQ ID NO:2; 10 predicted Casein Kinase II phosphorylation sites (PS00006) located at about amino 7–10, 91–94, 103–106, 118–121, 276–279, 341–344, 364–367, 470–473, 483–486, and 495–498 of SEQ ID NO:2; two predicted tyrosine kinase phosphorylation sites (PS00007) located at about amino acids 127–135 and 484–491 of SEQ ID NO:2; two predicted N-myristoylation sites (PS00008) located at about amino acids 288–293 and 349–354 of SEQ ID NO:2; and one predicted amidation site located at about amino acids 59–62 of SEQ ID NO:2.

For general information regarding PFAM identifiers, PS prefix and PF prefix domain identification numbers, refer to Sonnhammer et al. (1997) *Protein* 28:405–420 and http://www.psc.edu/general/software/packages/pfam/pfam.html.

A plasmid containing the nucleotide sequence encoding human 2504 (clone Fbh2504FL) was deposited with American Type Culture Collection (ATCC), 10801 University Boulevard, Manassas, Va. 20110-2209, on May 9, 2000 and assigned Accession Number 1843. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Human 15977

The human 15977 sequence (FIGS. 4A–4C; SEQ ID NO:4), which is approximately 4417 nucleotides long including untranslated regions, contains a predicted methionine-initiated coding sequence of about 1377 nucleotides (nucleotides 337–1713 of SEQ ID NO:4; SEQ ID NO:6). The coding sequence encodes a 459 amino acid protein (SEQ ID NO:5).

This mature protein form is approximately 459 amino acid residues in length (from about amino acid 1 to amino acid 459 of SEQ ID NO:5). Human 15977 contains the following regions or other structural features (FIGS. 6A and 6B): a eukaryotic protein kinase domain (PFAM Accession PF00069) located at about amino acid residues 44 to 276 of SEQ ID NO:5; and a serine/threonine kinase domain located at about amino acid residues 44 to 329 of SEQ ID NO:5.

The 15977 protein also includes the following domains: two predicted N-glycosylation sites (PS00001) located at about amino acids 370–373 and 388–391 of SEQ ID NO:5; two cAMP- and cGMP-dependent protein kinase phosphorylation sites (PS00004) located at about amino acids 270–273 and 451–454 SEQ ID NO:5; nine predicted Protein Kinase C phosphorylation sites (PS00005) located at about amino acids 14–16, 137–139, 199–201, 214–216, 229–231, 258–260, 269–271, 355–357, and 373–375 of SEQ ID NO:5; eight predicted Casein Kinase II sites (PS00006) located at about amino 96–99, 124–127, 150–153, 229–232, 258–261, 273–276, 355–358, and 411–414 of SEQ ID NO:5; two predicted N-myristoylation sites (PS00008) located at about amino 30–35 and 422–427 of SEQ ID NO:2; one predicted amidation site (PS00009) located at about amino acids 46–49 of SEQ ID NO:5; and a Serine/Threonine protein kinase active-site signature (PS 00108) located at about amino acids 160–172 of SEQ ID NO:5.

For general information regarding PFAM identifiers, PS prefix and PF prefix domain identification numbers, refer to Sonnhammer et al, (1997) *Protein* 28:405–420 and http://www.psc.edu/general/software/packages/pfam/pfam.html.

Human 14760

The human 14760 sequence (FIGS. 7A–7B; SEQ ID NO:7), which is approximately 2046 nucleotides long including untranslated regions, contains a predicted methionine-initiated coding sequence of about 1788 nucleotides (nucleotides 119–1906 of SEQ ID NO:7; SEQ ID NO:9). The coding sequence encodes a 596 amino acid protein (SEQ ID NO:8).

This mature protein form is approximately 596 amino acid residues in length (from about amino acid 1 to amino acid 596 of SEQ ID NO:2). Human 14760 contains the following regions or other structural features (FIGS. 9A and 9B): a eukaryotic protein kinase domain (PFAM Accession PF00069) located at about amino acid residues 285 to 540 of SEQ ID NO:8; and a serine/threonine kinase domain located at about amino acid residues 285 to 540 of SEQ ID NO:8.

The 14760 protein also includes the following domains: two predicted N-glycosylation sites (PS00001) located at about amino acids 278–281 and 416–419 of SEQ ID NO:8; three cAMP- and cGMP-dependent protein kinase phosphorylation sites (PS00004) located at about amino acids 140–143, 317–320, and 583–586 SEQ ID NO:8; 11 predicted Protein Kinase C phosphorylation sites (PS00005) located at about amino acids 17–19, 49–51, 59–61, 107–109, 159–161, 203–205, 224–226, 235–237, 247–249, 320–322, and 460–462 of SEQ ID NO:8; eight predicted Casein Kinase II phosphorylation sites (PS00006) located at about amino 157–160, 184–187, 203–206, 247–250, 301–304, 320–323, 351–354, and 379–382 of SEQ ID NO:8; one predicted tyrosine kinase phosphorylation sites (PS00007) located at about amino acids 370–376 of SEQ ID NO:8; nine predicted N-myristoylation sites (PS00008) located at about amino acids 83–88, 116–121, 135–140, 178–183, 241–246, 277–282, 293–298, 308–313, and 589–594 of SEQ ID NO:8; one predicted amidation site (PS00009) located at about amino acids 128–131 of SEQ ID NO:8; a protein kinases ATP-binding region signature located at about amino acids 291–299 of SEQ ID NO:8; and a Serine/Threonine protein kinase active-site signature (PS 00108) located at about amino acids 402–414 of SEQ ID NO:8.

For general information regarding PFAM identifiers, PS prefix and PF prefix domain identification numbers, refer to Sonnhammer et al. (1997) *Protein* 28:405–420 and http://www.psc.edu/general/software/packages/pfam/pfam.html.

own phosphorylation state or the phosphorylation state of another protein or polypeptide. Protein kinases can have a specificity for (i.e., a specificity to phosphorylate) serine/threonine residues, tyrosine residues, or both serine/threonine and tyrosine residues, e.g., the dual specificity kinases. As referred to herein, protein kinases preferably include a catalytic domain of about 200–400 amino acid residues in length, preferably about 200–300 amino acid residues in length, or more preferably about 250–300 amino acid residues in length. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42–52) the contents of which are incorporated herein by reference). These subdomains are also described in further detail herein.

Protein kinases play a role in signaling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. Thus, the molecules of the present invention may be involved in: 1) the regulation of transmis-

TABLE 1

Summary of Sequence Information for 2504, 15977, and 14760

| Gene | cDNA | ORF | Polypeptide | FIG. | ATCC Accession Number |
|---|---|---|---|---|---|
| 2504 | SEQ ID NO:1 | SEQ ID NO:3 | SEQ ID NO:2 | FIG. 1A-B | 1843 |
| 15977 | SEQ ID NO:4 | SEQ ID NO:6 | SEQ ID NO:5 | FIG. 4A-C | |
| 14760 | SEQ ID NO:7 | SEQ ID NO:9 | SEQ ID NO:8 | FIG. 7A-B | |

TABLE 2

Summary of Domains of 2504, 15977, and 14760

| Protein | Protein Kinase Domain | Serine/Threonine Kinase Domain |
|---|---|---|
| 2504 | About amino acids 37–286 of SEQ ID NO:2 | About amino acids 24–286 of SEQ ID NO:2 |
| 15977 | About amino acids 44–276 of SEQ ID NO:5 | About amino acids 44–329 of SEQ ID NO:5 |
| 14760 | About amino acids 285–540 of SEQ ID NO:8 | About amino acids 285–540 of SEQ ID NO:8 |

The 2504, 15977, and 14760 proteins contains a significant number of structural characteristics in common with members of the protein kinase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

A 2504, 15977, or 14760 polypeptide can include a "protein kinase domain" or regions homologous with a "protein kinase domain".

As used herein, the term "protein kinase" includes a protein or polypeptide which is capable of modulating its sion of signals from cellular receptors, e.g., cell growth factor receptors; 2) the modulation of the entry of cells, e.g., precursor cells, into mitosis; 3) the modulation of cellular differentiation; 4) the modulation of cell death; and 5) the regulation of cytoskeleton function, e.g., actin bundling.

Inhibition or over stimulation of the activity of protein kinases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma.

As used herein, the term "protein kinase domain" includes an amino acid sequence of about 150 to 400 amino acid residues in length and having a bit score for the alignment of the sequence to the protein kinase domain (HMM) of at least 50. Preferably, a protein kinase domain includes at least about 200–400 amino acids, more preferably about 200–300 amino acid residues, or about 220–270 amino acids and has a bit score for the alignment of the sequence to the protein kinase domain (HMM) of at least 120 or greater. The protein kinase domain (HMM) has been assigned the PFAM Accession PF00069 (http://genome.wustl.edu/Pfam/html). An alignment of the protein kinase domain (amino acids 37 to 286 of SEQ ID NO:2) of human 2504 with a consensus amino acid sequence derived from a hidden Markov model is depicted in FIG. 3A. An alignment of the protein kinase domain (amino acids 44 to 276 of SEQ ID NO:5) of human 15977 with a consensus amino acid sequence derived from a hidden Markov model is depicted in FIG. 6A. An alignment of the protein kinase domain (amino acids 285 to 540 of SEQ ID NO:8) of human 14760 with a consensus amino acid sequence derived from a hidden Markov model is depicted in FIG. 9A.

In a preferred embodiment 2504, 15977, or 14760 polypeptide or protein has a "protein kinase domain" or a region which includes at least about 200–400 more preferably about 200–300 or 220–270 amino acid residues and has at least about 70% 80% 90% 95%, 99%, or 100% homology with a "protein kinase domain," e.g., the protein kinase domain of human 2504, 15977, or 14760 (e.g., residues 37–286 of SEQ ID NO:2; residues 44–276 of SEQ ID NO:5, or residues 285–540 of SEQ ID NO:8).

A 2504, 15977, or 14760 molecule can further include a "serine/threonine kinase domain."

As used herein, the term "serine/threonine kinase domain" includes an amino acid sequence of about 150 to 400 amino acid residues in length and having a bit score for the alignment of the sequence to the protein kinase domain (HMM) of at least 15. Preferably, a serine/threonine kinase domain includes at least about 200–400 amino acids, more preferably about 200–300 amino acid residues, or about 220–270 amino acids and has a bit score for the alignment of the sequence to the serine/threonine kinase domain (HMM) of at least 50 or greater. An alignment of the serine/threonine kinase domain (amino acids 24 to 286 of SEQ ID NO:2) of human 2504 with a consensus amino acid sequence derived from a hidden Markov model is depicted in FIG. 3B. An alignment of the serine/threonine kinase domain (amino acids 44 to 329 of SEQ ID NO:5) of human 15977 with a consensus amino acid sequence derived from a hidden Markov model is depicted in FIG. 6B. An alignment of the serine/threonine kinase domain (amino acids 285 to 540 of SEQ ID NO:8) of human 14760 with a consensus amino acid sequence derived from a hidden Markov model is depicted in FIG. 9A.

In a preferred embodiment 2504, 15977, or 14760 polypeptide or protein has a "serine/threonine kinase domain" or a region which includes at least about 200–400 more preferably about 200–300 or 220–270 amino acid residues and has at least about 70% 80% 90% 95%, 99%, or 100% homology with a "serine/threonine kinase domain," e.g., the serine/threonine kinase domain of human 2504, 15977, or 14760 (e.g., residues 24–286 of SEQ ID NO:2; residues 44–329 of SEQ ID NO:5, or residues 285–540 of SEQ ID NO:8).

To identify the presence of a "protein kinase" domain or a "serine/threonine kinase"domain in a 2504, 15977, or 14760 protein sequence, and make the determination that a polypeptide or protein of interest has a particular profile, the amino acid sequence of the protein can be searched against a database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al.(1987) *Proc. Natl. Acad. Sci. USA* 84:4355–4358; Krogh et al.(1994) *J. Mol. Biol.* 235:1501–1531; and Stultz et al.(1993) *Protein Sci.* 2:305–314, the contents of which are incorporated herein by reference.

A 2504, 15977, or 14760 family member can include a protein kinase domain, e.g. a serine/threonine kinase domain.

As the 2504, 15977, or 14760 polypeptides of the invention may modulate 2504, 15977, or 14760-mediated activities, they may be useful as of for developing novel diagnostic and therapeutic agents for 2504, 15977, or 14760-mediated or related disorders, as described below.

As used herein, a "2504, 15977, or 14760 activity", "biological activity of 2504, 15977, or 14760" or "functional activity of 2504, 15977, or 14760", refers to an activity exerted by a 2504, 15977, or 14760 protein, polypeptide or nucleic acid molecule on e.g., a 2504, 15977, or 14760-responsive cell or on a 2504, 15977, or 14760 substrate, e.g., a protein substrate, as determined in vivo or in vitro. In one embodiment, a 2504, 15977, or 14760 activity is a direct activity, such as an association with a 2504, 15977, or 14760 target molecule. A "target molecule" or "binding partner" is a molecule with which a 2504, 15977, or 14760 protein binds or interacts in nature, e.g., a protein containing one or more serine and or threonine residues. A 2504, 15977, or 14760 activity can also be an indirect activity, e.g., a cellular signaling activity mediated by interaction of the 2504, 15977, or 14760 protein with a 2504, 15977, or 14760 receptor. For example, the 2504, 15977, or 14760 proteins of the present invention can have one or more of the following activities: 1) the regulation of transmission of signals from cellular receptors, e.g., cell growth factor receptors; 2) the modulation of the entry of cells, e.g., precursor cells, into mitosis; 3) the modulation of cellular differentiation, 4) the modulation of cell death; 5) the regulation of cytoskeleton function, e.g., actin bundling; or 6) the ability to phosphorylate a substrate.

Based on the above-described sequence similarities, the 2504, 15977, and 14760 molecules of the present invention are predicted to have similar biological activities as protein kinase family members. Thus, the 2504, 15977, and 14760 molecules can act as novel diagnostic targets and therapeutic agents for controlling one or more of cellular proliferative and/or differentiative disorders, disorders associated with bone metabolism, immune disorders, hematopoietic disorders, cardiovascular disorders, liver disorders, viral diseases, pain or metabolic disorders.

Figure 10:
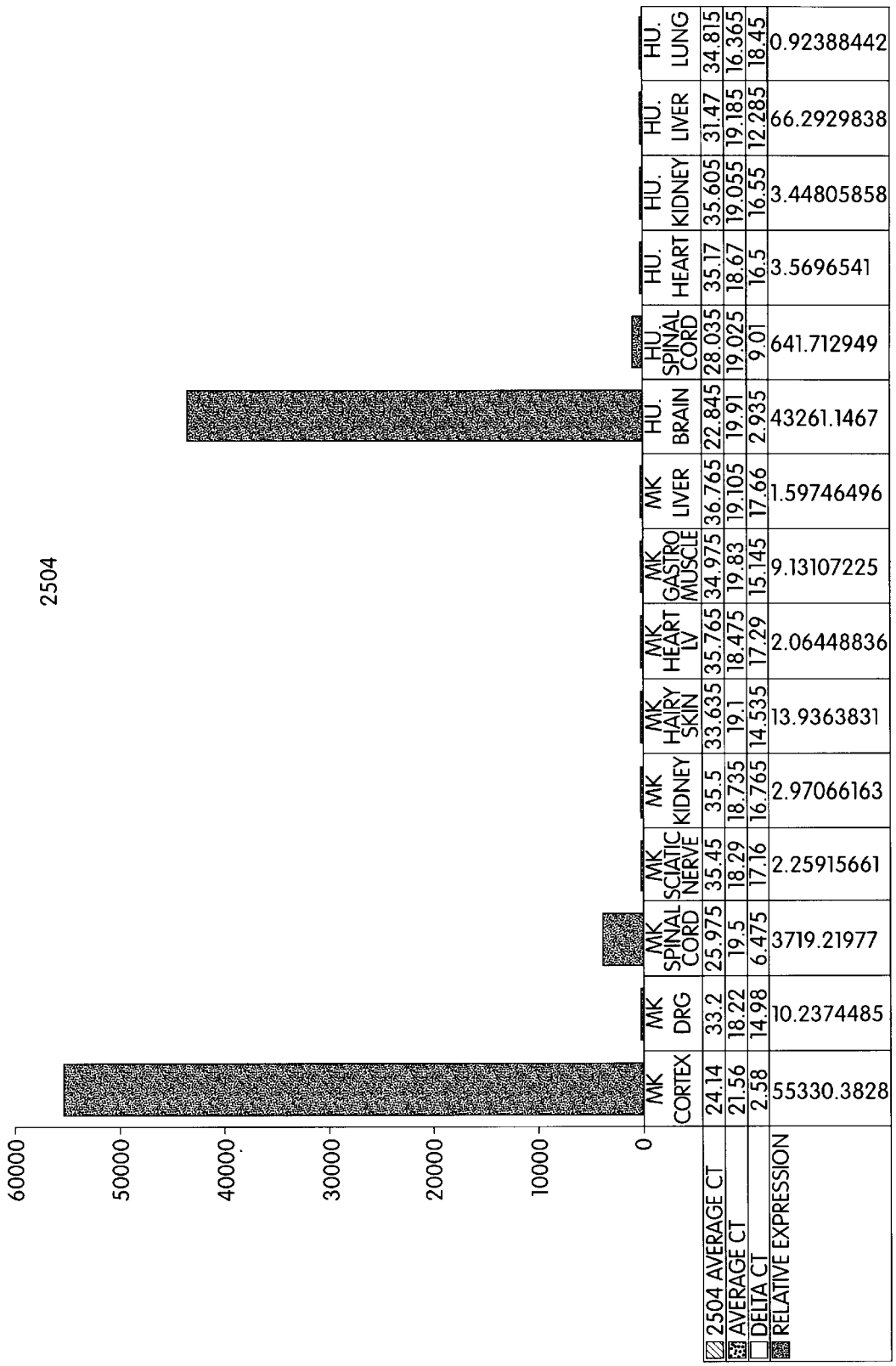
FIG. 10 is a bar graph depicting relative 2504 mRNA expression as determined by TaqMan assays on mRNA derived from the following tissues: MK (monkey) cortex; MK dorsal root ganglion; MK spinal cord; MK sciatic nerve; MK kidney; MK hairy skin; MK heart left ventricle; MK gastro muscle; MK liver; human brain; human spinal cord; human heart; human kidney; human liver; and human lung. The highest 2504 mRNA expression was observed in MK cortex, human brain, and MK and human spinal cord.
Figure 12A:
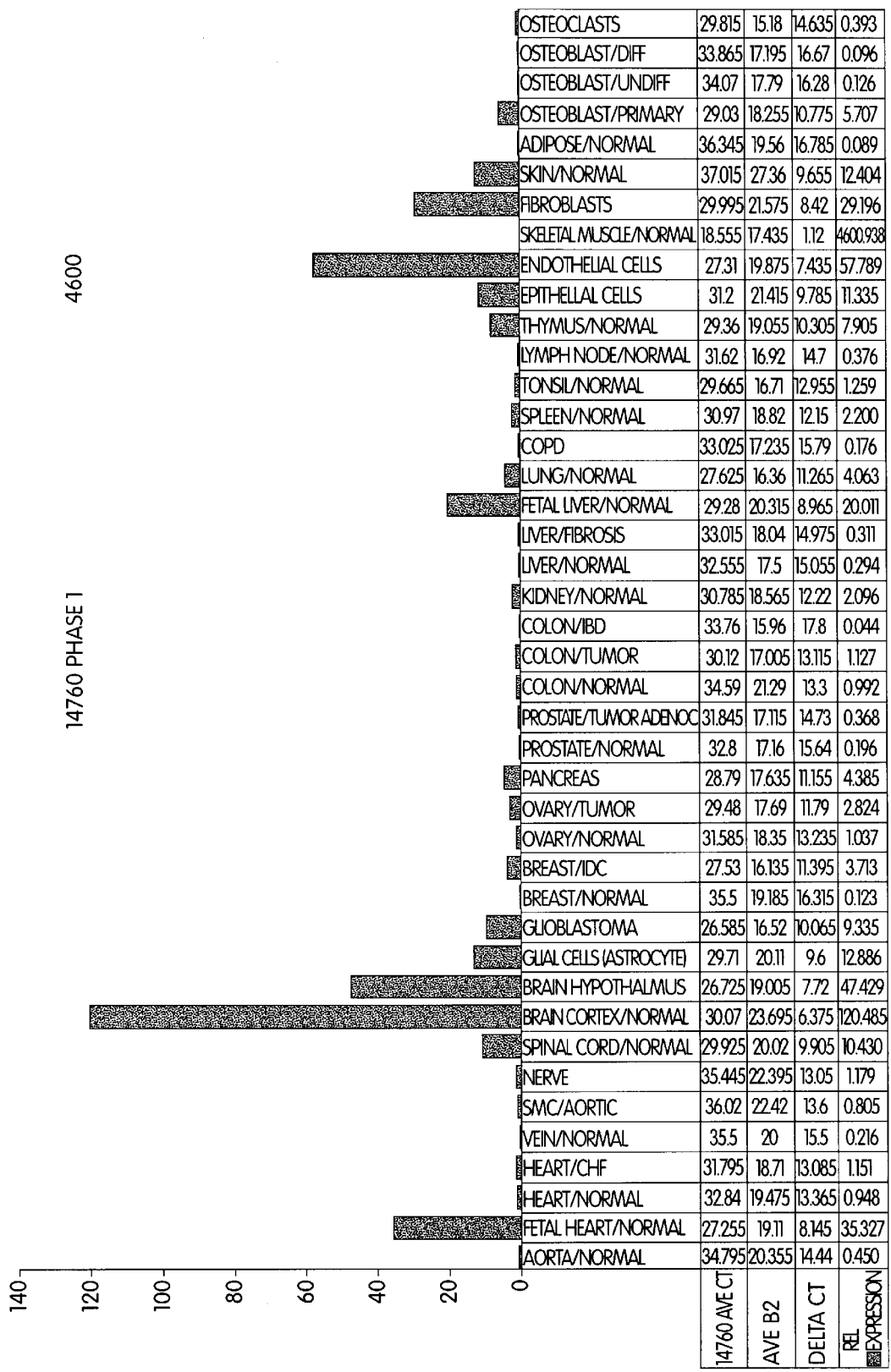
FIG. 12A is a bar graph depicting relative 14760 mRNA expression as determined by TaqMan assays on mRNA derived from the following human tissues. Columns are numbered at five-column intervals at the bottom of the Figure (i.e., columns 1–42), and correspond to the following: (1) Aorta/Normal; (2) Fetal Heart/Normal; (3) Heart/Normal; (4) Heart/CHF; (5) Vein/Normal; (6) SMC/aortic; (7) Nerve; (8) Spinal Cord/Normal; (9) Brain Cortex/Normal; (10) Brain hypothalamus; (11) Glial Cells (astrocytes); (12) Glioblastoma; (13) Breast/Normal; (14) Breast/IDC; (15) Ovary/Normal; (16) Ovary/Tumor; (17) Pancreas; (18) Prostate/Normal; (19) Prostate/tumor adenocarcinoma; (20) Colon/Normal; (21) Colon/Tumor; (22) Colon/IBD; (23) Kidney/Normal; (24) Liver/Normal; (25) Liver/Fibrosis; (26) Fetal Liver/Normal; (27) Lung/Normal; (28) COPD; (29) Spleen/Normal; (30) Tonsil/Normal; (31) Lymph Node/Normal; (32) Thymus/Normal; (33) Epithelial Cells; (34) Endothelial cells; (35) Skeletal Muscle/Normal; (36) Fibroblasts; (37) Skin/Normal; (38) Adipose/normal; (39) Osteoblast/Primary; (40) Osteoblast/undifferentiated; (41) Osteoblast/differentiated; and (42) Osteoclasts. Elevated 14760 mRNA expression was observed in normal brain (e.g., cortex and hypothalamus), and normal fetal liver and fetal heart.
Figure 12B:
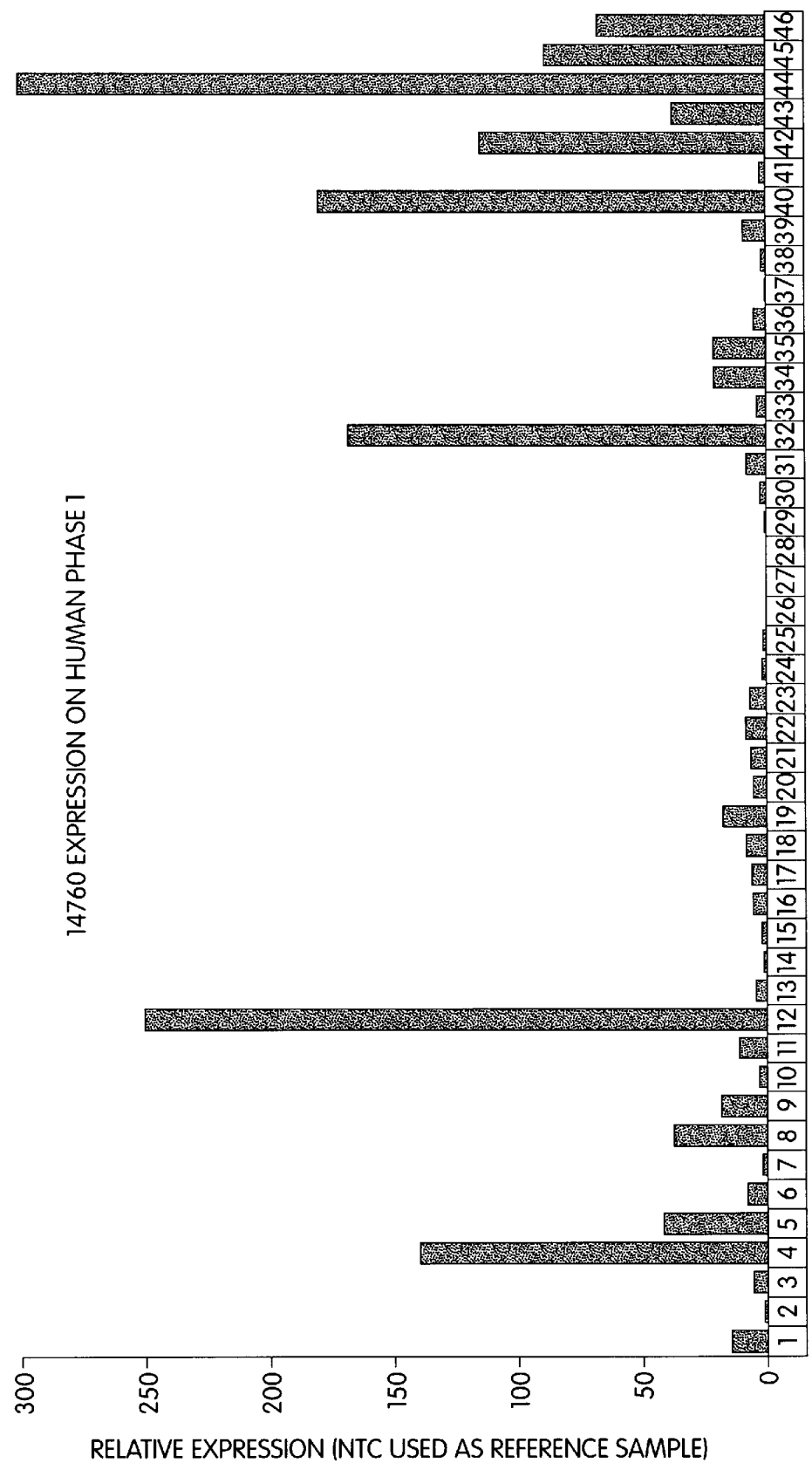
FIG. 12B is a bar graph depicting relative 14760 mRNA expression as determined by TaqMan assays on mRNA derived from the following tissues and cell lines. Columns are numbered at five-column intervals at the bottom of the Figure (i.e., columns 1–46), and correspond to the following: (1) Heart; (2) Lung; (3) Kidney; (4) Fetal Liver; (5) Spleen; (6) Granulocytes.; (7) NHDF mock; (8) NHLF mock; (9) NHLF TGF; (10) HepG2 Mock; (11) HepG2 TGF; (12) Pass Stell; (13) Liver Pool; (14) Control liver; (15) LF/NDR 191; (16) LF/NDR 193; (17) LF/NDR 079; (18) LN NDR 173; (19) Tonsil; (20) TH1 24 hr. MP39; (21) TH2 24 hr. MP39; (22) TH1 24 hr. MP21; (23) TH2 24 hr. MP21; (24) CD4; (25) CD8; (26) CD19; (27) CD3 MP42 rest; (28) CD14; (29) PBMC MOCK; (30) Bone marrow mononuclear cells (BM MNC); (31) CD34-positive cells (MPB CD34+); (32) Bone marrow glycophorin-positive cells (BM GPA+); (33) Cord Blood; (34) Erythroid; (35) Megakaryocytes; (36) Neutrophils (Neut) after 14 days in culture (dl4); (37) CD14-/CD15+; (38) MBM CD11b; (39) HepG2; (40) HepG2.2.15; (41) MAI 01; (42) HL60; (43) K562; (44) Molt 4; (45) Hep3B Normoxia; and (46) Hep3B Hypoxia. Elevated 14760 mRNA expression was observed in pass stell, bone marrow glycophorin-positive cell lines, MOLT-4 cell lines and fetal liver.
Figure 12C:
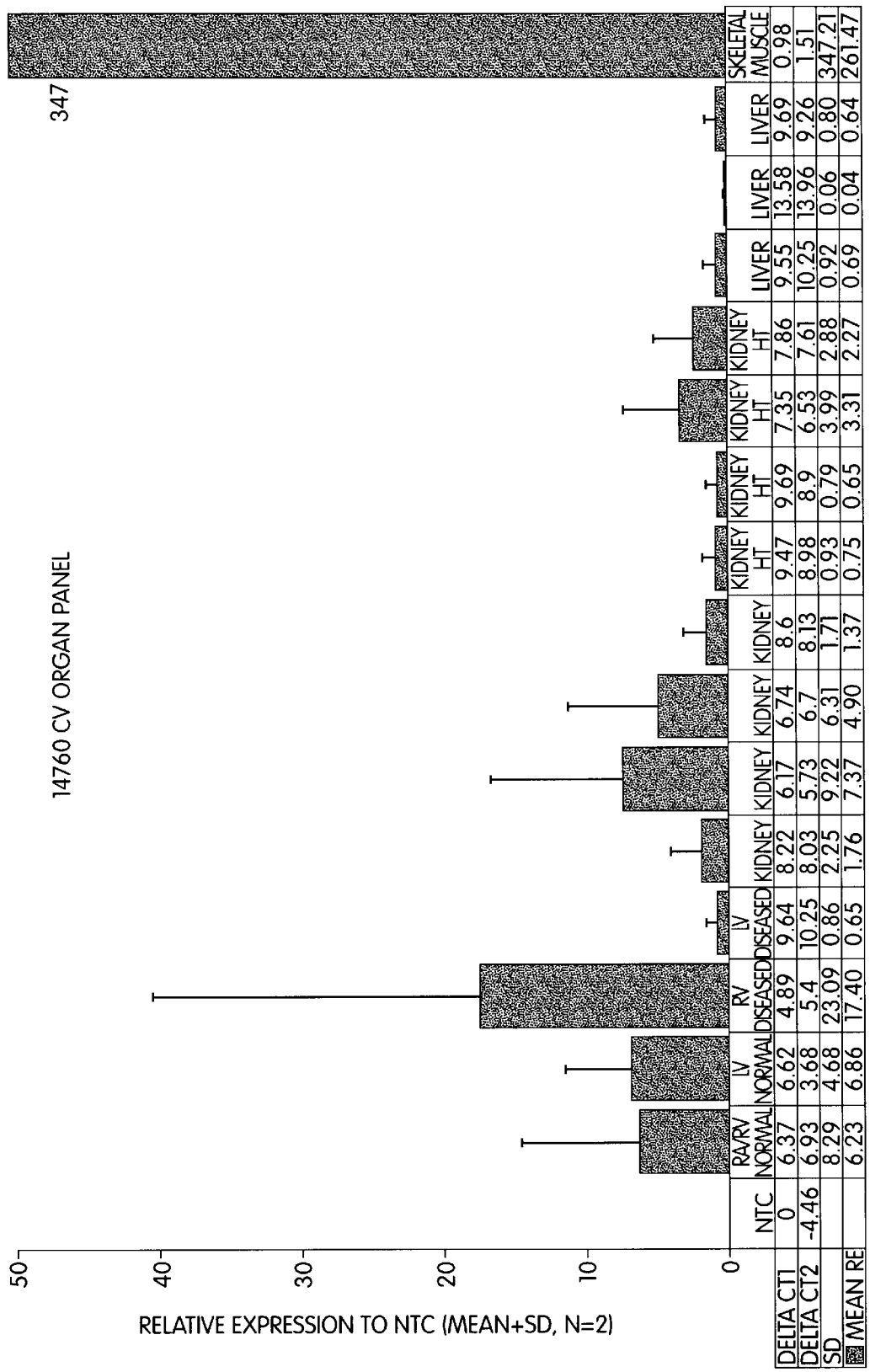
FIG. 12C is a bar graph (cardiovascular organ panel) depicting relative 14760 mRNA expression as determined by TaqMan assays on mRNA derived from the following cardiovascular tissues: normal atria; normal left ventricle; diseased right ventricle; diseased left ventricle; kidney; liver; and skeletal muscle. Elevated 14760 mRNA expression was observed in skeletal muscle and cardiovascular tissues.

In addition, the 2504, 15977, and 14760 molecules of the invention may modulate physiological and pathological processes in the cells or tissues where they are expressed. For example, Taq Man studies described herein show abundant expression of 2504, 15977, and 14760 mRNAs in neural tissues, including the brain cortex and hypothalamus (FIGS. 10, 11 and 12A). 15977 mRNA is also highly expressed in epithelial cells, astrocytes (glial cells), HUVEC cells, smooth muscle cells and fetal liver (FIG. 11). 14760 mRNA is also abundantly expressed in the fetal liver, endothelial cells, fetal heart, fibroblasts, bone marrow glycophorin-positive cells, hepatocytes, cardiovascular cells, and skeletal muscle. Accordingly, these molecules can act as novel diagnostic targets and therapeutic agents of disorders involving the cells or tissues where they are expressed, e.g., neural (e.g., brain or astrocytic) disorders; cardiovascular and blood vessel (smooth muscle or endothelial cell) disorders; immune disorders (e.g., disorders involving glycophorin-positive cells); hepatic or liver disorders; skin disorders; skeletal disorders, among others.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Aberrant expression and/or activity of 2504, 15977, or 14760 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 2504, 15977, or 14760 molecules effects in bone cells, e.g. osteoclasts and osteoblasts, that may in turn result in bone formation and degeneration. For example, 2504, 15977, or 14760 molecules may support different activities of bone resorbing osteoclasts such as the stimulation of differentiation of monocytes and mononuclear phagocytes into osteoclasts. Accordingly, 2504, 15977, or 14760 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The 2504, 15977, or 14760 nucleic acid and protein of the invention can be used to treat and/or diagnose a variety of immune disorders. Exemplary immune disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:2267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Additional examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions,leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of cardiovascular disorders include, but are not limited to, heart failure, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts-early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyangiitis (microscopic polyarteritis, hypersensitivity or leukocytoclastic angiitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, Al-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 2504, 15977, or 14760 molecules may play an important role in the etiology of certain viral diseases, including but not limited to Hepatitis B, Hepatitis C and Herpes Simplex Virus (HSV). Modulators of 2504, 15977, or 14760 activity could be used to control viral diseases. The modulators can be used in the treatment and/or diagnosis of viral infected tissue or virus-associated tissue fibrosis, especially liver and liver fibrosis. Also, 2504, 15977, or 14760 modulators can be used in the treatment and/or diagnosis of virus-associated carcinoma, especially hepatocellular cancer.

Additionally, 2504, 15977, or 14760 may play an important role in the regulation of metabolism or pain disorders. Diseases of metabolic imbalance include, but are not limited to, obesity, anorexia nervosa, cachexia, lipid disorders diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with muscoloskeletal disorders, e.g., joint pain; tooth pain; headaches; pain associated with surgery; pain related to irritable bowel syndrome; or chest pain.

Disorders involving the skeletal muscle include tumors such as rhabdomyosarcoma. Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

The 2504, 15977, or 14760 protein, fragments thereof, and derivatives and other variants of the sequence in SEQ ID NO:2, SEQ ID NO:5, or SEQ ID NO:8 thereof are collectively referred to as "polypeptides or proteins of the invention" or "2504, 15977, or 14760 polypeptides or proteins". Nucleic acid molecules encoding such polypeptides or proteins are collectively referred to as "nucleic acids of the invention" or "2504, 15977, or 14760 nucleic acids." 2504, 15977, or 14760 molecules refer to 2504, 15977, or 14760 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5 M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 2504, 15977, or 14760 protein, preferably a mammalian 2504, 15977, or 14760 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 2504, 15977, or 14760 protein having less than about 30%, 20%, 10% and more preferably 5% (by dry weight), of non-2504, 15977, or 14760 protein (also referred to herein as a "contaminating protein"), or of chemical precursors or non-2504, 15977, or 14760 chemicals. When the 2504, 15977, or 14760 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 2594, 15977, or 14760 (e.g., the sequence of SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843) without abolishing or more preferably, without substantially altering a biological activity, whereas an "essential" amino acid residue results in such a change. For example, amino acid residues that are conserved among the polypeptides of the present invention, e.g., those present in the protein kinase or serine/threonine kinase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine. arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus. a predicted nonessential amino acid residue in a 2504, 15977, or 14760 protein is preferably replaced with another amino acid residue from the same side chain family. Alternatively, in another embodiment, mutations can be introduced randomly along all or part of a 2504, 15977, or 14760 coding sequence, such as by saturation mutagenesis, and the resultant mutants can be screened for 2504, 15977, or 14760 biological activity to identify mutants that retain activity. Following mutagenesis of SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843, the encoded protein can be expressed recombinantly and the activity of the protein can be determined.

As used herein, a "biologically active portion" of a 2504, 15977, or 14760 protein includes a fragment of a 2504, 15977, or 14760 protein which participates in an interaction between a 2504, 15977, or 14760 molecule and a non-2504, 15977, or 14760 molecule. Biologically active portions of a 2504, 15977, or 14760 protein include peptides comprising amino acid sequences sufficiently homologous to or derived from the amino acid sequence of the 2504, 15977, or 14760 protein, e.g., the amino acid sequence shown in SEQ ID NO:2, SEQ ID NO:5, or SEQ ID NO:8, which include less amino acids than the full length 2504, 15977, or 14760 proteins, and exhibit at least one activity of a 2504, 15977, or 14760 protein. Typically, biologically active portions comprise a domain or motif with at least one activity of the 2504, 15977, or 14760 protein, e.g., protein kinase activity. A biologically active portion of a 2504, 15977, or 14760 protein can be a polypeptide which is, for example, 10, 25, 50, 100, 200 or more amino acids in length. Biologically active portions of a 2504, 15977, or 14760 protein can be used as targets for developing agents which modulate a 2504, 15977, or 14760 mediated activity, e.g., protein kinase activity.

Particularly preferred 2504, 15977, 14760 polypeptides of the present invention have an amino acid sequence substantially identical to the amino acid sequence of SEQ ID NO:2, 5 or 8. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2, 5 or 8 are termed sufficiently or substantially identical. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1, 3, 4, 6, 7 or 9 are termed substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 2504 amino acid sequence of SEQ ID NO:2 having 150 amino acid residues, at least 200, preferably at least 250, more preferably at least 300, even more preferably at least 350, and even more preferably at least 400, 450 or 501 amino acid residues are aligned; when aligning a second sequence to the 15977 amino acid sequence of SEQ ID NO:5 having 137 amino acid residues, at least 183, preferably at least 229, more preferably at least 275, even more preferably at least 321, and even more preferably at least 367, 413 or 459 amino acid residues are aligned; when aligning a second sequence to the 14760 amino acid sequence of SEQ ID NO:8 having 178 amino acid residues, at least 238, preferably at least 298, more preferably at least 357, even more preferably at least 417, and even more preferably at least 476, 536, or 596 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol Biol.* 215:403–10. BLAST nucleotide searches can be performed with the NBLAST program, score=100, wordlength=12 to obtain nucleotide sequences homologous to 2504, 15977, or 14760 nucleic acid molecules of the invention. BLAST protein searches can be performed with the XBLAST program, score=50, wordlength=3 to obtain amino acid sequences homologous to 2504, 15977, or 14760 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 2504, 15977, or 14760 polypeptide described herein, e.g., a full length 2504, 15977, or 14760 protein or a fragment thereof, e.g., a biologically active portion of 2504, 15977, or 14760 protein. Also included is a nucleic acid fragment suitable for use as a hybridization probe, which can be used, e.g., to a identify nucleic acid molecule encoding a polypeptide of the invention, 2504, 15977, or 14760 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, SEQ ID NO:4, SEQ ID NO:7, or the nucleotide sequence of the DNA insert of the plasmid deposited with ATCC as Accession Number 1843, or a portion of any of these nucleotide sequences. In one embodiment, the nucleic acid molecule includes sequences encoding the human 2504, 15977, or 14760 protein (i.e., "the coding region", from nucleotides 154–1656 of SEQ ID NO:1, nucleotides 337–1713 of SEQ ID NO:4. and nucleotides 119–1906 of SEQ ID NO:7), as well as 5' untranslated sequences (nucleotides 1660–2297 of SEQ ID NO:1, nucleotides 1717–4417 of SEQ ID NO:4, nucleotides 1910–2046 of SEQ ID NO:7). Alternatively, the nucleic acid molecule can include only the coding region of SEQ ID NO:1, SEQ ID NO:4, or SEQ ID NO:7, (e.g., nucleotides 154–1656 of SEQ ID NO:1, corresponding to SEQ ID NO:3; nucleotides 337–1713 of SEQ ID NO:4, corresponding to SEQ ID NO:6; or nucleotides 119–1906 of SEQ ID NO:7, corresponding to SEQ ID NO:9) and, e.g., no flanking sequences which normally accompany the subject sequence. In another embodiment, the nucleic acid molecule encodes a sequence corresponding to the mature protein of SEQ ID NO:2, SEQ ID NO:5, or SEQ ID NO:8.

In another embodiment, an isolated nucleic acid molecule of the invention includes a nucleic acid molecule which is a complement of the nucleotide sequence shown in SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843, or a portion of any of these nucleotide sequences. In other embodiments, the nucleic acid molecule of the invention is sufficiently complementary to the nucleotide sequence shown in SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843 such that it can hybridize to the nucleotide sequence shown in SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843, thereby forming a stable duplex.

In one embodiment, an isolated nucleic acid molecule of the present invention includes a nucleotide sequence which is at least about 60%, 65%, 70%, 75%, 80%, 85%, 90%, 91%, 92% 93%, 94%, 95%, 96%, 97%, 98%, 99%, or more homologous to the nucleotide sequence shown in SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843. In the case of an isolated nucleic acid molecule which is longer than or equivalent in length to the reference sequence, e.g., SEQ ID NO:1, the comparison is made with the full length of the reference sequence. Where the isolated nucleic acid molecule is shorter that the reference sequence, e.g., shorter than SEQ ID NO:1, SEQ ID NO:3, SEQ ID NO:4, SEQ ID NO:6, SEQ ID NO:7, or SEQ ID NO:9, the comparison is made to a segment of the reference sequence of the same length (excluding any loop required by the homology calculation).

2504, 15977, or 14760 Nucleic Acid Fragments

A nucleic acid molecule of the invention can include only a portion of the nucleic acid sequence of SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843. For example, such a nucleic acid molecule can include a fragment which can be used as a probe or primer or a fragment encoding a portion of a 2504, 15977, or 14760 protein, e.g., an immunogenic or biologically active portion of a 2504, 15977, or 14760 protein. A fragment can comprise: nucleotides 262–1011 of SEQ ID NO:1, which encodes a protein kinase domain of human 2504; nucleotides 223–1011 of SEQ ID NO:1, which encodes a serine/threonine kinase domain of human 2504; nucleotides 466–1164 of SEQ ID NO:4, which encodes a protein kinase domain of human 15977; nucleotides 466–1323 of SEQ ID NO:4, which encodes a serine/threonine kinase domain of human 15977; nucleotides 971–1738 of SEQ ID NO:7, which encodes a protein kinase domain of human 14760; nucleotides 971–1738 of SEQ ID NO:7, which encodes a serine/threonine kinase domain of human 14760. The nucleotide sequence determined from the cloning of the 2504, 15977, or 14760 gene allows for the generation of probes and primers designed for use in identifying and/or cloning other 2504, 15977, or 14760 family members, or fragments thereof, as well as 2504, 15977, or 14760 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 200 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include a protein kinase domain, e.g., a serine/threonine kinase domain. In a preferred embodiment the fragment is at least, 50, 100, 200, 300, 400, 500, 600, 700, or 900 base pairs in length.

2504, 15977, or 14760 probes and primers are provided. Typically a probe/primer is an isolated or purified oligonucleotide. The oligonucleotide typically includes a region of nucleotide sequence that hybridizes under a stringent condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843, or of a naturally occurring allelic variant or mutant of SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a protein kinase domain (e.g., about amino acid residues 37–286 of SEQ ID NO:2; about amino acid residues 44–276 of SEQ ID NO:5; or about amino acid residues 285–540 of SEQ ID NO:8) or a serine/threonine kinase domain (e.g., about amino acid residues 24–286 of SEQ ID NO:2; about amino acid residues 44–329 of SEQ ID NO:5; or about amino acid residues 285–540 of SEQ ID NO:8).

In another embodiment a set of primers is provided, e.g., primers suitable for use in a PCR, which can be used to amplify a selected region of a 2504, 15977, or 14760 sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the following regions are provided: a protein kinase domain (e.g., about amino acid residues 37–286 of SEQ ID NO:2; about amino acid residues 44–276 of SEQ ID NO:5; or about amino acid residues 285–540 of SEQ ID NO:8) or a serine/threonine kinase domain (e.g., about amino acid residues 24–286 of SEQ ID NO:2; about amino acid residues 44–329 of SEQ ID NO:5; or about amino acid residues 285–540 of SEQ ID NO:8).

A nucleic acid fragment can encode an epitope bearing region of a polypeptide described herein.

A nucleic acid fragment encoding a "biologically active portion of a 2504, 15977, or 14760 polypeptide" can be prepared by isolating a portion of the nucleotide sequence of SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843, which encodes a polypeptide having a 2504, 15977, or 14760 biological activity (e.g., the biological activities of the 2504, 15977, or 14760 proteins are described herein), expressing the encoded portion of the 2504, 15977, or 14760 protein (e.g., by recombinant expression in vitro) and assessing the activity of the encoded portion of the 2504, 15977, or 14760 protein. For example, a nucleic acid fragment encoding a biologically active portion of 2504, 15977, or 14760 includes a protein kinase domain (e.g., about amino acid residues 37–286 of SEQ ID NO:2, about amino acid residues 44–276 of SEQ ID NO:5, or about amino acid residues 285–540 of SEQ ID NO:8) or a serine/threonine kinase domain (e.g., about amino acid residues 24–286 of SEQ ID NO:2; about amino acid residues 44–329 of SEQ ID NO:5; or about amino acid residues 285–540 of SEQ ID NO:8).

A nucleic acid fragment encoding a biologically active portion of a 2504, 15977, or 14760 polypeptide may comprise a nucleotide sequence that is greater than about 300 or more nucleotides in length (e.g., greater than about 400 nucleotides in length).

In a preferred embodiment, the fragment is at least 300, 400, 450, 500, 550, 600, 650, 700, 750, 800, 850, 900, 950, 1000, 1100, 1200, 1300, or 1400 nucleotides in length, or more nucleotides in length and hybridizes under a stringent hybridization condition described herein to a nucleic acid molecule of SEQ ID NO:1, 3, 4, 6, 7 or 9.

In a preferred embodiment, a nucleic acid fragment includes a nucleotide sequence comprising nucleotides SEQ ID NO:1, 3, 4, 6, 7 or 9, or a portion thereof, wherein each portion is about 400 or longer nucleotides and hybridizes under a stringent hybridization condition described herein to a nucleic acid molecule of SEQ ID NO:1, 3, 4, 6, 7 or 9.

2504, 15977, or 14760 Nucleic Acid Variants

The invention further encompasses nucleic acid molecules that differ from the nucleotide sequence shown in SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843. Such differences can be due to degeneracy of the genetic code (and result in a nucleic acid which encodes the same 2504, 15977, or 14760 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, SEQ ID NO:5, or SEQ ID NO:8. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non preferred, for a particular expression system. E.g., the nucleic acid can be one in which at least one colon, at preferably at least 10%, or 20% of the codons has been altered such that the sequence is optimized for expression in e. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843, e.g., as follows: by at least one but less than 10, 20, 30, or 40 nucleotides; at least one but less than 1%, 5%, 10% or 20% of the in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:2, SEQ ID NO:5, SEQ ID NO:8 or a fragment of one of these sequences. Such nucleic acid molecules can readily be identified as being able to hybridize under a stringent condition described herein, to the nucleotide sequence shown in SEQ ID NO:3, SEQ ID NO:6, SEQ ID NO:9, or a fragment of one of these sequences. Nucleic acid molecules corresponding to orthologs, homologs, and allelic variants of the 2504, 15977, or 14760 cDNAs of the invention can further be isolated by mapping to the same chromosome or locus as the 2504, 15977, or 14760 gene.

Preferred variants include those that are correlated with protein kinase activity.

Allelic variants of 2504, 15977, or 14760, e.g., human 2504, 15977, or 14760, include both functional and non-functional proteins. Functional allelic variants are naturally occurring amino acid sequence variants of the 2504, 15977, or 14760 protein within a population that maintain the ability to modulate the phosphorylation state of itself or another protein or polypeptide. Functional allelic variants will typically contain only conservative substitution of one or more amino acids of SEQ ID NO:2, SEQ ID NO:5, SEQ ID NO:8, or substitution, deletion or insertion of non-critical residues in non-critical regions of the protein. Non-functional allelic variants are naturally-occurring amino acid sequence variants of the 2504, 15977, or 14760, e.g., human 2504, 15977, or 14760, protein within a population that do not have the ability to modulate the phosphorylation state of itself or another protein or polypeptide. Non-functional allelic variants will typically contain a non-conservative substitution, a deletion, or insertion, or premature truncation of the amino acid sequence of SEQ ID NO:2, SEQ ID NO:5, SEQ ID NO:8, or a substitution, insertion, or deletion in critical residues or critical regions of the protein.

Moreover, nucleic acid molecules encoding other 2504, 15977, or 14760 family members and, thus, which have a nucleotide sequence which differs from the 2504, 15977, or 14760 sequences of SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 1843 are intended to be within the scope of the invention.

Antisense Nucleic Acid Molecules, Ribozymes and Modified 2504, 15977, or 14760 Nucleic Acid Molecules In another aspect, the invention features, an isolated nucleic acid molecule which is antisense to 2504, 15977, or 14760. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 2504, 15977, or 14760 coding strand, or to only a portion thereof (e.g., the coding region of human 2504, 15977, or 14760 corresponding to SEQ ID NO:3, SEQ ID NO:6, or SEQ ID NO:9). In another embodiment, the antisense nucleic acid molecule is anti-sense to a "noncoding region" of the coding strand of a nucleotide sequence encoding 2504, 15977, or 14760 (e.g., the 5' and 3' untranslated regions).

An antisense nucleic acid can be designed such that it is complementary to the entire coding region of 2504, 15977, or 14760 mRNA, but more preferably is an oligonucleotide which is antisense to only a portion of the coding or noncoding region of 2504, 15977, or 14760 mRNA. For example, the antisense oligonucleotide can be complementary to the region surrounding the translation start site of 2504, 15977, or 14760 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 2504, 15977, or 14760 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 2504, 15977, or 14760-encoding nucleic acid can include one or more sequences complementary to the nucleotide sequence of a 2504, 15977, or 14760 cDNA disclosed herein (i.e., SEQ ID NO:1, SEQ ID NO:3, SEQ ID NO:4, SEQ ID NO:6, SEQ ID NO:7, or SEQ ID NO:9), and a sequence having known catalytic sequence responsible for mRNA cleavage (see U.S. Pat. No. 5,093,246 or Haseloff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a 2504, 15977, or 14760-encoding mRNA. See, e.g., Cech et al. U.S. Pat. No. 4,987,071; and Cech et al. U.S. Pat. No. 5,116,742. Alternatively, 2504, 15977, or 14760 mRNA can be used to select a catalytic RNA having a specific ribonuclease activity from a pool of RNA molecules. See, e.g., Bartel, D. and Szostak, J. W. (1993) *Science* 261:1411–1418.

2504, 15977, or 14760 gene expression can be inhibited by targeting nucleotide sequences complementary to the regulatory region of the 2504, 15977, or 14760 (e.g., the 2504, 15977, or 14760 promoter and/or enhancers) to form triple helical structures that prevent transcription of the 2504, 15977, or 14760 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15. The potential sequences that can be targeted for triple helix formation can be increased by creating a so called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 2504, 15977, or 14760 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of 2504, 15977, or 14760 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 2504, 15977, or 14760 nucleic acid molecules can also be used in the analysis of single base pair mutations in a gene, (e.g., by PNA-directed PCR clamping); as 'artificial restriction enzymes' when used in combination with other enzymes, (e.g., SI nucleases (Hyrup B. (1 996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 2504, 15977, or 14760 nucleic acid of the invention, two complementary regions one having a fluorophore and one a quencher such that the molecular beacon is useful for quantitating the presence of the 2504, 15977, or 14760 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 2504, 15977, or 14760 Polypeptides

In another aspect, the invention features, an isolated 2504, 15977, or 14760 protein, or fragment, e.g., a biologically active portion, for use as immunogens or antigens to raise or test (or more generally to bind) anti-2504, 15977, or 14760 antibodies. 2504, 15977, or 14760 protein can be isolated from cells or tissue sources using standard protein purification techniques. 2504, 15977, or 14760 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events The polypeptide can be expressed in systems, e.g., cultured cells, which result in substantially the same postranslational modifications present when expressed the polypeptide is expressed in a native cell, or in systems which result in the alteration or omission of postranslational modifications, e.g., gylcosylation or cleavage, present when expressed in a native cell.

In a preferred embodiment, a 2504, 15977, or 14760 polypeptide has one or more of the following characteristics:

(i) it has the ability to promote the modulation of its own phosphorylation state or the phosphorylation state of another protein or polypeptide;

(ii) it has a molecular weight, e.g., a deduced molecular weight, amino acid composition or other physical characteristic of a 2504, 15977, or 14760 polypeptide, e.g., the polypeptide of SEQ ID NO:2, SEQ ID NO:5, or SEQ ID NO:8;

(iii) it has an overall sequence similarity of at least 60%, more preferably at least 70, 80, 90, or 95%, with a polypeptide of SEQ ID NO:2, SEQ ID NO:5, or SEQ ID NO:8;

(iv) it has a protein kinase domain which preferably has an overall sequence similarity of about 70%, 80%, 90% or 95% with amino acid residues 37–286 of SEQ ID NO:2, amino acid residues 44–276 of SEQ ID NO:5, or amino acid residues 285–540 of SEQ ID NO:5;

(v) it has at least 70%, preferably 80%, and most preferably 95% of the cysteines found amino acid sequence of the native protein.

In a preferred embodiment the 2504, 15977, or 14760 protein, or fragment thereof, differs from the corresponding sequence in SEQ ID NO:2, SEQ ID NO:5, or SEQ ID NO:8. In one embodiment it differs by at least one but by less than 15, 10 or 5 amino acid residues. In another it differs from the corresponding sequence in SEQ ID NO:2, SEQ ID NO:5, or SEQ ID NO:8 by at least one residue but less than 20%, 15%, 10% or 5% of the residues in it differ from the corresponding sequence in SEQ ID NO:2, SEQ ID NO:5, or SEQ ID NO:8. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the protein kinase domain. In another preferred embodiment one or more differences are in non-active site residues, e.g. outside of the protein kinase domain.

Other embodiments include a protein that contain one or more changes in amino acid sequence, e.g., a change in an amino acid residue which is not essential for activity. Such 2504, 15977, or 14760 proteins differ in amino acid sequence from SEQ ID NO:2, SEQ ID NO:5, or SEQ ID NO:8, yet retain biological activity.

In one embodiment, the protein includes an amino acid sequence at least about 60%, 65%, 70%, 75%, 80%, 85%, 90%, 95%, 98% or more homologous to SEQ ID NO:2, SEQ ID NO:5, or SEQ ID NO:8.

A 2504, 15977, or 14760 protein or fragment is provided which varies from the sequence of SEQ ID NO:2, SEQ ID NO:5, or SEQ ID NO:8 in non-active site residues by at least one but by less than 15, 10 or 5 amino acid residues in the protein or fragment but which does not differ from SEQ ID NO:2, SEQ ID NO:5, or SEQ ID NO:8 in regions having protein kinase activity. (If this comparison requires alignment the sequences should be aligned for maximum homology. "Looped" out sequences from deletions or insertions, or mismatches, are considered differences.) In some embodiments the difference is at a non essential residue or is a conservative substitution, while in others the difference is at an essential residue or is a non conservative substitution.

In one embodiment, a biologically active portion of a 2504, 15977, or 14760 protein includes a protein kinase domain, e.g. a serine/threonine kinase domain. Moreover, other biologically active portions, in which other regions of the protein are deleted, can be prepared by recombinant techniques and evaluated for one or more of the functional activities of a native 2504, 15977, or 14760 protein.

In a preferred embodiment, the 2504, 15977, or 14760 protein has an amino acid sequence shown in SEQ ID NO:2, SEQ ID NO:5, or SEQ ID NO:8. In other embodiments, the 2504, 15977, or 14760 protein is substantially identical to SEQ ID NO:2, SEQ ID NO:5, or SEQ ID NO:8. In yet another embodiment, the 2504, 15977, or 14760 protein is substantially identical to SEQ ID NO:2, SEQ ID NO:5, or SEQ ID NO:8 and retains the functional activity of the protein of SEQ ID NO:2, SEQ ID NO:5, or SEQ ID NO:8, as described in detail in subsection 1 above. Accordingly, in another embodiment, the 2504, 15977, or 14760 protein is a protein which includes an amino acid sequence at least about 50%, 55%, 60%, 65%, 70%, 75%, 80%, 85%, 90%, 95%, 98% or more identical to SEQ ID NO:2, SEQ ID NO:5, or SEQ ID NO:8.

2504, 15977, or 14760 Chimeric or Fusion Proteins

In another aspect, the invention provides 2504, 15977, or 14760 chimeric or fusion proteins. As used herein, a 2504, 15977, or 14760 "chimeric protein" or "fusion protein" includes a 2504, 15977, or 14760 polypeptide linked to a non-2504, 15977, or 14760 polypeptide. A "non-2504, 15977, or 14760 polypeptide" refers to a polypeptide having an amino acid sequence corresponding to a protein which is not substantially homologous to the 2504, 15977, or 14760 protein, e.g., a protein which is different from the 2504, 15977, or 14760 protein and which is derived from the same or a different organism. The 2504, 15977, or 14760 polypeptide of the fusion protein can correspond to all or a portion e.g., a fragment described herein of a 2504, 15977, or 14760 amino acid sequence. In a preferred embodiment, a 2504, 15977, or 14760 fusion protein includes at least one (or two) biologically active portion of a 2504, 15977, or 14760 protein. The non-2504, 15977, or 14760 polypeptide can be fused to the N-terminus or C-terminus of the 2504, 15977, or 14760 polypeptide.

The fusion protein can include a moiety which has a high affinity for a ligand. For example, the fusion protein can be a GST-2504, 15977, or 14760 fusion protein in which the 2504, 15977, or 14760 sequences are fused to the C-terminus of the GST sequences. Such fusion proteins can facilitate the purification of recombinant 2504, 15977, or 14760. Alternatively, the fusion protein can be a 2504, 15977, or 14760 protein containing a heterologous signal sequence at its N-terminus. In certain host cells (e.g., mammalian host cells), expression and/or secretion of 2504, 15977, or 14760 can be increased through use of a heterologous signal sequence.

Fusion proteins can include all or a part of a serum protein, e.g., an IgG constant region, or human serum albumin.

The 2504, 15977, or 14760 fusion proteins of the invention can be incorporated into pharmaceutical compositions and administered to a subject in vivo. The 2504, 15977, or 14760 fusion proteins can be used to affect the bioavailability of a 2504, 15977, or 14760 substrate. 2504, 15977, or 14760 fusion proteins may be useful therapeutically for the treatment of disorders caused by, for example, (i) aberrant modification or mutation of a gene encoding a 2504, 15977, or 14760 protein; (ii) mis-regulation of the 2504, 15977, or 14760 gene; and (iii) aberrant post-translational modification of a 2504, 15977, or 14760 protein.

Moreover, the 2504, 15977, or 14760-fusion proteins of the invention can be used as immunogens to produce anti-2504, 15977, or 14760 antibodies in a subject, to purify 2504, 15977, or 14760 ligands and in screening assays to identify molecules which inhibit the interaction of 2504, 15977, or 14760 with a 2504, 15977, or 14760 substrate.

Expression vectors are commercially available that already encode a fusion moiety (e.g., a GST polypeptide). A 2504, 15977, or 14760-encoding nucleic acid can be cloned into such an expression vector such that the fusion moiety is linked in-frame to the 2504, 15977, or 14760 protein.

Variants of 2504, 15977, or 14760 Proteins

In another aspect, the invention also features a variant of a 2504, 15977, or 14760 polypeptide, e.g., which functions as an agonist (mimetics) or as an antagonist. Variants of the 2504, 15977, or 14760 proteins can be generated by mutagenesis, e.g., discrete point mutation, the insertion or deletion of sequences or the truncation of a 2504, 15977, or 14760 protein. An agonist of the 2504, 15977, or 14760 proteins can retain substantially the same, or a subset, of the biological activities of the naturally occurring form of a 2504, 15977, or 14760 protein. An antagonist of a 2504, 15977, or 14760 protein can inhibit one or more of the activities of the naturally occurring form of the 2504, 15977, or 14760 protein by, for example, competitively modulating a 2504, 15977, or 14760-mediated activity of a 2504, 15977, or 14760 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 2504, 15977, or 14760 protein.

Variants of a 2504, 15977, or 14760 protein can be identified by screening combinatorial libraries of mutants, e.g., truncation mutants, of a 2504, 15977, or 14760 protein for agonist or antagonist activity.

Libraries of fragments e.g., N terminal, C terminal, or internal fragments, of a 2504, 15977, or 14760 protein coding sequence can be used to generate a variegated population of fragments for screening and subsequent selection of variants of a 2504, 15977, or 14760 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 2504, 15977, or 14760 variants (Arkin and Yourvan (1992) *Proc. Natl. Acad. Sci. USA* 89:7811–7815; Delgrave et al. (1993) *Protein Engineering* 6(3):327–331).

Cell based assays can be exploited to analyze a variegated 2504, 15977, or 14760 library. For example, a library of expression vectors can be transfected into a cell line, e.g., a cell tine, which ordinarily responds to 2504, 15977, or 14760 in a substrate-dependent manner. The transfected cells are then contacted with 2504, 15977, or 14760 and the effect of the expression of the mutant on signaling by the 2504, 15977, or 14760 substrate can be detected, e.g., by measuring protein kinase activity. Plasmid DNA can then be recovered from the cells which score for inhibition, or alternatively, potentiation of signaling by the 2504, 15977, or 14760 substrate, and the individual clones further characterized.

In another aspect, the invention features a method of making a 2504, 15977, or 14760 polypeptide, e.g., a peptide having a non-wild type activity, e.g., an antagonist, agonist, or super agonist of a naturally occurring 2504, 15977, or 14760 polypeptide, e.g., a naturally occurring 2504, 15977, or 14760 polypeptide. The method includes: altering the sequence of a 2504, 15977, or 14760 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 2504, 15977, or 14760 polypeptide a biological activity of a naturally occurring 2504, 15977, or 14760 polypeptide. The method includes: altering the sequence, e.g., by substitution or deletion of one or more residues, of a 2504, 15977, or 14760 polypeptide, e.g., altering the sequence of a non-conserved region, or a domain or residue described herein, and testing the altered polypeptide for the desired activity.

Anti-2504, 15977, or 14760 Antibodies

In another aspect, the invention provides an anti-2504, 15977, and 14760 antibody. The term "antibody" as used herein refers to an immunoglobulin molecule or immunologically active portion thereof, i.e., an antigen-binding portion. The antibody can be a polyclonal, monoclonal, recombinant, e.g., a chimeric or humanized, fully human, non-human, e.g., murine, a single chain antibody, a recombinantly produced antibody, or a fragment thereof (e.g., immunologically active fragments thereof). Examples of immunologically active fragments of immunoglobulin molecules include F(ab) and F(ab')$_2$ fragments which can be generated by treating the antibody with an enzyme such as pepsin.

In other embodiments, the antibody can be fully human (e.g., antibodies made in a mouse which has been genetically engineered to produce antibodies from human immunoglobulin sequences), or non-human, e.g., murine or rat. An antibody can be one in which the variable region, or a portion thereof, e.g., the CDR's, are generated in a nonhuman organism, e.g., a rat or mouse. Chimeric, CDR-grafted, humanized are within the invention. Antibodies generated in a nonhuman organism, e.g., a rat or mouse, and then modified, e.g., in the variable framework or constant region, to decrease antigenicity in a human are within the invention. A humanized or CDR-grafted antibody will have at least one or two but generally all three recipient CDR's (of heavy and or light chains) replaced with a donor CDR. In a preferred embodiment a humanized antibody will have framework residues identical to the donor framework residue or to another amino acid other than the recipient framework residue. In preferred embodiments, the donor will be a rodent antibody, e.g., a rat or mouse antibody, and the recipient will be a human framework or a human consensus framework.

In a preferred embodiment, the antibody has: effector function; and can fix complement. In other embodiments the antibody does not; recruit effector cells; or fix complement.

The antibody can be coupled to a toxin, e.g., a polypeptide toxin, e,g, ricin or diptheria toxin or active fragement hereof, or a radionuclide, or imaging agent, e.g. a radioactive, enzymatic, or other, e.g., imaging agent,e.g., a NMR contrast agent. Labels which produce detectable radioactive emissions or fluorescence are preferred.

In preferred embodiments an antibody can be made by immunizing with purified 2504, 15977, and 14760 antigen, or a fragment thereof, e.g., a fragment described herein. A full-length 2504, 15977, and 14760 protein or, antigenic peptide fragment of 2504, 15977, and 14760 can be used as an immunogen or can be used to identify anti-2504, 15977, and 14760 antibodies made with other immunogens, e.g., cells, and the like. The antigenic peptide of 2504, 15977, and 14760 should include at least 8 amino acid residues of the amino acid sequence shown in SEQ ID NO:2, 5 or 8 and encompasses an epitope of 2504, 15977, and 14760. Preferably, the antigenic peptide includes at least 10 amino acid residues, more preferably at least 15 amino acid residues, even more preferably at least 20 amino acid residues, and most preferably at least 30 amino acid residues.

Antibodies which bind only native 2504, 15977, and 14760 protein, only denatured or otherwise non-native 2504, 15977, and 14760 protein, or which bind both, are with in the invention. Antibodies with linear or conformational epitopes are within the invention. Conformational epitopes can sometimes be identified by identifying antibodies which bind to native but not denatured 2504, 15977, and 14760 protein.

Fragments of 2504, 15977, or 14760 which include, e.g., residues 220–235 of SEQ ID NO:2, residues 261–391 of SEQ ID NO:5, or residues 21–81 of SEQ ID NO:8, can be used to make, e.g., used as immunogens, or used to characterize the specificity of an antibody or antibodies against what are believed to be hydrophilic regions of the 2504, 15977, or 14760 protein. Similarly, a fragment of 2504, 15977, or 14760 which includes, e.g., residues 203–219 of SEQ ID NO:2 or residues 466–483 of SEQ ID NO:8 can be used to make an antibody against what is believed to be a hydrophobic region of the 2504, 15977, or 14760 protein; a fragment of 2504, 15977, or 14760 which includes residues 37–286 of SEQ ID NO:2, residues 44–276 of SEQ ID NO:5, or residues 285–540 of SEQ ID NO:8 can be used to make an antibody against the protein kinase region of the 2504, 15977, or 14760 protein; a fragment of 2504, 15977, or 14760 which includes residues 24–286 of SEQ ID NO:2, residues 44–329 of SEQ ID NO:5, or residues 285–540 of SEQ ID NO:8 can be used to make an antibody against the serine/threonine kinase region of the 2504, 15977, or 14760 protein.

Antibodies reactive with, or specific for, any of these regions, or other regions or domains described herein are provided.

Preferred epitopes encompassed by the antigenic peptide are regions of 2504, 15977, or 14760 are located on the surface of the protein, e.g., hydrophilic regions, as well as regions with high antigenicity. For example, an Emini surface probability analysis of the human 2504, 15977, or 14760 protein sequence can be used to indicate the regions that have a particularly high probability of being localized to the surface of the 2504, 15977, or 14760 protein and are thus likely to constitute surface residues useful for targeting antibody production.

In a preferred embodiment the antibody binds an epitope on any domain or region on 2504, 15977, or 14760 proteins described herein.

Chimeric, humanized, but most preferably, completely human antibodies are desirable for applications which include repeated administration, e.g., therapeutic treatment (and some diagnostic applications) of human patients.

The anti-2504, anti-15977, or anti-14760 antibody can be a single chain antibody. A single-chain antibody (scFV) may be engineered (see, for example, Colcher, D., et al. *Ann N Y Acad Sci* 1999 Jun 30;880:263–80; and Reiter, Y. *Clin Cancer Res* 1996 Feb;2(2):245–52). The single chain antibody can be dimerized or multimerized to generate multivalent antibodies having specificities for different epitopes of the same target 2504, 15977, or 14760 protein.

An anti-2504, 15977, or 14760 antibody (e.g., monoclonal antibody) can be used to isolate 2504, 15977, or 14760 by standard techniques, such as affinity chromatography or immunoprecipitation. Moreover, an anti-2504, 15977, or 14760 antibody can be used to detect 2504, 15977, or 14760 protein (e.g., in a cellular lysate or cell supernatant) in order to evaluate the abundance and pattern of expression of the protein. Anti-2504, 15977, or 14760 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

The invention also includes a nucleic acid that encodes an anti-2504, 15977, and 14760 antibody, e.g., an anti-2504, 15977, and 14760 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-2504, 15977, and 14760 antibody, e.g., and antibody described herein, and method of using said cells to make a 2504, 15977, and 14760 antibody.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 2504, 15977, or 14760 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 2504, 15977, or 14760 proteins, mutant forms of 2504, 15977, or 14760 proteins, fusion proteins, and the like).

The recombinant expression vectors of the invention can be designed for expression of 2504, 15977, or 14760 proteins in prokaryotic or eukaryotic cells. For example, polypeptides of the invention can be expressed in *E. coi*, insect cells (e.g., using baculovirus expression vectors), yeast cells or mammalian cells. Suitable host cells are discussed further in Goeddel, *Gene Expression Technology. Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 2504, 15977, or 14760 activity assays, (e.g., direct assays or competitive assays described in detail below), or to generate antibodies specific for 2504, 15977, or 14760 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six (6) weeks).

To maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 2504, 15977, or 14760 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, *Reviews-Trends in Genetics*, Vol. 1(1) 1986.

Another aspect the invention provides a host cell which includes a nucleic acid molecule described herein, e.g., a 2504, 15977, or 14760 nucleic acid molecule within a recombinant expression vector or a 2504, 15977, or 14760 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 2504, 15977, or 14760 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-inediated transfection, lipofection, or electroporation A host cell of the invention can be used to produce (i.e., express) a 2504, 15977, or 14760 protein. Accordingly, the invention further provides methods for producing a 2504, 15977, or 14760 protein using the host cells of the invention. In one embodiment, the method includes culturing the host cell of the invention (into which a recombinant expression vector encoding a 2504, 15977, or 14760 protein has been introduced) in a suitable medium such that a 2504, 15977, or 14760 protein is produced. In another embodiment, the method further includes isolating a 2504, 15977, or 14760 protein from the medium or the host cell.

In another aspect, the invention features, a cell or purified preparation of cells which include a 2504, 15977, or 14760 transgene, or which otherwise misexpress 2504, 15977, or 14760. The cell preparation can consist of human or non human cells, e.g., rodent cells, e.g., mouse or rat cells, rabbit cells, or pig cells. In preferred embodiments, the cell or cells include a 2504, 15977, or 14760 transgene, e.g., a heterologous form of a 2504, 15977, or 14760, e.g., a gene derived from humans (in the case of a non-human cell). The 2504, 15977, or 14760 transgene can be misexpressed, e.g., overexpressed or underexpressed. In other preferred embodiments, the cell or cells include a gene which misexpress an endogenous 2504, 15977, or 14760, e.g., a gene the expression of which is disrupted, e.g., a knockout. Such cells can serve as a model for studying disorders which are related to mutated or mis-expressed 2504, 15977, or 14760 alleles or for use in drug screening.

In another aspect, the invention features, a human cell, e.g., a hematopoietic stem cell, transformed with nucleic acid which encodes a subject 2504, 15977, or 14760 polypeptide.

Also provided are cells, e.g., human cells, e.g., human hematopoietic or fibroblast cells in which an endogenous 2504, 15977, or 14760 is under the control of a regulatory sequence that does not normally control the expression of the endogenous 2504, 15977, or 14760 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 2504, 15977, or 14760 gene. For example, an endogenous 2504, 15977, or 14760 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 2504, 15977, and 14760 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (200 1) *Nat. Biotechnol.* 19:3 5; and U.S. Pat. No. 5,876,742. Production of 2504, 15977, and 14760 polypeptide can be regulated in the subject by administering an agent (e.g., a steroid hormone) to the subject. In another preferred embodiment, the implanted recombinant cells express and secrete an antibody specific for a 2504, 15977, and 14760 polypeptide. The antibody can be any antibody or any antibody derivative described herein.

Transgenic Animals

The invention provides non-human transgenic animals. Such animals are useful for studying the function and/or activity of a 2504, 15977, or 14760 protein and for identifying and/or evaluating modulators of 2504, 15977, or 14760 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 2504, 15977, or 14760 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 2504, 15977, or 14760 protein to particular cells. A transgenic founder animal can be identified based upon the presence of a 2504, 15977, or 14760 transgene in its genome and/or expression of 2504, 15977, or 14760 mRNA in tissues or cells of the animals. A transgenic founder animal can then be used to breed additional animals carrying the transgene. Moreover, transgenic animals carrying a transgene encoding a 2504, 15977, or 14760 protein can further be bred to other transgenic animals carrying other transgenes.

2504, 15977, or 14760 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 2504, 15977, or 14760 protein (e.g., via a recombinant expression vector in a host cell in gene therapy applications), to detect a 2504, 15977, or 14760 mRNA (e.g., in a biological sample) or a genetic alteration in a 2504, 15977, or 14760 gene, and to modulate 2504, 15977, or 14760 activity, as described further below. The 2504, 15977, or 14760 proteins can be used to treat disorders characterized by insufficient or excessive production of a 2504, 15977, or 14760 substrate or production of 2504, 15977, or 14760 inhibitors. In addition, the 2504, 15977, or 14760 proteins can be used to screen for naturally occurring 2504, 15977, or 14760 substrates, to screen for drugs or compounds which modulate 2504, 15977, or 14760 activity, as well as to treat disorders characterized by insufficient or excessive production of 2504, 15977, or 14760 protein or production of 2504, 15977, or 14760 protein forms which have decreased, aberrant or unwanted activity compared to 2504, 15977, or 14760 wild type protein. Such disorders include those characterized by aberrant signaling or aberrant, e.g., hyperproliferative, cell growth. Moreover, the anti-2504, 15977, or 14760 antibodies of the invention can be used to detect and isolate 2504, 15977, or 14760 proteins, regulate the bioavailability of 2504, 15977, or 14760 proteins, and modulate 2504, 15977, or 14760 activity.

A method of evaluating a compound for the ability to interact with, e.g., bind, a subject 2504, 15977, or 14760 polypeptide is provided. The method includes: contacting the compound with the subject 2504, 15977, or 14760 polypeptide; and evaluating ability of the compound to interact with, e.g., to bind or form a complex with the subject 2504, 15977, or 14760 polypeptide. This method can be performed in vitro, e.g., in a cell free system, or in vivo, e.g., in a two-hybrid interaction trap assay. This method can be used to identify naturally occurring molecules which interact with subject 2504, 15977, or 14760 polypeptide. It can also be used to find natural or synthetic inhibitors of subject 2504, 15977, or 14760 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 2504, 15977, or 14760 proteins, have a stimulatory or inhibitory effect on, for example, 2504, 15977, or 14760 expression or 2504, 15977, or 14760 activity, or have a stimulatory or inhibitory effect on, for example, the expression or activity of a 2504, 15977, or 14760 substrate. Compounds thus identified can be used to modulate the activity of target gene products (e.g., 2504, 15977, or 14760 genes) in a therapeutic protocol, to elaborate the biological function of the target gene product, or to identify compounds that disrupt normal target gene interactions.

In one embodiment, the invention provides assays for screening candidate or test compounds which are substrates of a 2504, 15977, or 14760 protein or polypeptide or a biologically active portion thereof. In another embodiment, the invention provides assays for screening candidate or test compounds which bind to or modulate the activity of a 2504, 15977, or 14760 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. *J. Med. Chem.* 1994, 37: 2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Nati. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner USP 5,223,409), spores (Ladner USP '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a 2504, 15977, or 14760 protein or biologically active portion thereof is contacted with a test compound, and the ability of the test compound to modulate 2504, 15977, or 14760 activity is determined.

Determining the ability of the test compound to modulate 2504, 15977, or 14760 activity can be accomplished by monitoring, for example, protein kinase activity. The cell, for example, can be of mammalian origin, e.g., human.

The ability of the test compound to modulate 2504, 15977, or 14760 binding to a compound, e.g., a 2504, 15977, or 14760 substrate, or to bind to 2504, 15977, or 14760 can also be evaluated. This can be accomplished, for example, by coupling the compound, e.g., the substrate, with a radioisotope or enzymatic label such that binding of the compound, e.g., the substrate, to 2504, 15977, or 14760 can be determined by detecting the labeled compound, e.g., substrate, in a complex. Alternatively, 2504, 15977, or 14760 could be coupled with a radioisotope or enzymatic label to monitor the ability of a test compound to modulate 2504, 15977, or 14760 binding to a 2504, 15977, or 14760 substrate in a complex. For example, compounds (e.g., 2504, 15977, or 14760 substrates) can be labeled with $125I$, $^{35}S$, $^{14}C$, or 3H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 2504, 15977, or 14760 substrate) to interact with 2504, 15977, or 14760 with or without the labeling of any of the interactants can be evaluated. For example, a microphysiometer can be used to detect the interaction of a compound with 2504, 15977, or 14760 without the labeling of either the compound or the 2504, 15977, or 14760. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 2504, 15977, or 14760.

In yet another embodiment, a cell-free assay is provided in which a 2504, 15977, or 14760 protein or biologically active portion thereof is contacted with a test compound and the ability of the test compound to bind to the 2504, 15977, or 14760 protein or biologically active portion thereof is evaluated. Preferred biologically active portions of the 2504, 15977, or 14760 proteins to be used in assays of the present invention include fragments which participate in interactions with non-2504, 15977, or 14760 molecules, e.g., fragments with high surface probability scores.

Soluble and/or membrane-bound forms of isolated proteins (e.g., 2504, 15977, or 14760 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethyl-amminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In one embodiment, assays are performed where the ability of an agent to block protein kinase activity within a cell is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 2504, 15977, or 14760 protein to bind to a target molecule can be accomplished using real-time Biomolecular Interaction Analysis (BIA) (see, e.g., Sjolander, S. and Urbaniczky, C. (1991) *Anal. Chem.* 63:2338–20 2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 2504, 15977, or 14760, an anti 2504, 15977, or 14760 antibody or its target molecule to facilitate separation of complexed from uncomplexed forms of one or both of the proteins, as well as to accommodate automation of the assay. Binding of a test compound to a 2504, 15977, or 14760 protein, or interaction of a 2504, 15977, or 14760 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/2504, 15977, or 14760 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 2504, 15977, or 14760 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 2504, 15977, or 14760 binding or activity determined using standard techniques.

Other techniques for immobilizing either a 2504, 15977, or 14760 protein or a target molecule on matrices include using conjugation of biotin and streptavidin. Biotinylated 2504, 15977, or 14760 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 2504, 15977, or 14760 protein or target molecules but which do not interfere with binding of the 2504, 15977, or 14760 protein to its target molecule. Such antibodies can be derivatized to the wells of the plate, and unbound target or 2504, 15977, or 14760 protein trapped in the wells by antibody conjugation. Methods for detecting such complexes, in addition to those described above for the GST-immobilized complexes, include immunodetection of complexes using antibodies reactive with the 2504, 15977, or 14760 protein or target molecule, as well as enzyme-linked assays which rely on detecting an enzymatic activity associated with the 2504, 15977, or 14760 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci* 1993 Aug;18(8):284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., *J. Mol Recognit* 1998 Winter; 11(1–6):141–8; Hage, D. S., and Tweed, S. A. *J. Chromatogr B Biomed Sci Appl* 1997 Oct 10;699(1–2):499–525). Further, fluorescence energy transfer may also be conveniently utilized, as described herein, to detect binding without further purification of the complex from solution.

In a preferred embodiment, the assay includes contacting the 2504, 15977, or 14760 protein or biologically active portion thereof with a known compound which binds 2504, 15977, or 14760 to form an assay mixture, contacting the assay mixture with a test compound, and determining the ability of the test compound to interact with a 2504, 15977, or 14760 protein, wherein determining the ability of the test compound to interact with a 2504, 15977, or 14760 protein includes determining the ability of the test compound to preferentially bind to 2504, 15977, or 14760 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 2504, 15977, or 14760 genes herein identified. In an alternative embodiment, the invention provides methods for determining the ability of the test compound to modulate the activity of a 2504, 15977, or 14760 protein through modulation of the activity of a downstream effector of a 2504, 15977, or 14760 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 2504, 15977, or 14760 proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with 2504, 15977, or 14760 ("2504, 15977, or 14760-binding proteins" or "2504, 15977, or 14760-bp") and are involved in 2504, 15977, or 14760 activity. Such 2504, 15977, or 14760-bps can be activators or inhibitors of signals by the 2504, 15977, or 14760 proteins or 2504, 15977, or 14760 targets as, for example, downstream elements of a 2504, 15977, or 14760-mediated signaling pathway.

The two-hybrid system is based on the modular nature of most transcription factors, which consist of separable DNA-binding and activation domains. Briefly, the assay utilizes two different DNA constructs. In one construct, the gene that codes for a 2504, 15977, or 14760 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 2504, 15977, or 14760 protein can be the fused to the activator domain.) If the "bait" and the "prey" proteins are able to interact, in vivo, forming a 2504, 15977, or 14760-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 2504, 15977, or 14760 protein.

In another embodiment, modulators of 2504, 15977, or 14760 expression are identified. For example, a cell or cell free mixture is contacted with a candidate compound and the expression of 2504, 15977, or 14760 mRNA or protein evaluated relative to the level of expression of 2504, 15977, or 14760 mRNA or protein in the absence of the candidate compound. When expression of 2504, 15977, or 14760 mRNA or protein is greater in the presence of the candidate compound than in its absence, the candidate compound is identified as a stimulator of 2504, 15977, or 14760 mRNA or protein expression. Alternatively, when expression of 2504, 15977, or 14760 mRNA or protein is less (statistically significantly less) in the presence of the candidate compound than in its absence, the candidate compound is identified as an inhibitor of 2504, 15977, or 14760 mRNA or protein expression. The level of 2504, 15977, or 14760 mRNA or protein expression can be determined by methods described herein for detecting 2504, 15977, or 14760 mRNA or protein.

In another aspect, the invention pertains to a combination of two or more of the assays described herein. For example, a modulating agent can be identified using a cell-based or a cell free assay, and the ability of the agent to modulate the activity of a 2504, 15977, or 14760 protein can be confirmed in vivo, e.g., in an animal.

This invention further pertains to residues 203–219 (SEQ ID NO:2), novel agents identified by the above-described screening assays. Accordingly, it is within the scope of this invention to further use an agent identified as described herein (e.g., a 2504, 15977, or 14760 modulating agent, an antisense 2504, 15977, or 14760 nucleic acid molecule, a 2504, 15977, or 14760-specific antibody, or a 2504, 15977, or 14760-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 2504, 15977, or 14760 with a disease; (ii) identify an individual from a minute biological sample (tissue typing); and (iii) aid in forensic identification of a biological sample. These applications are described in the subsections below.

Chromosome Mapping

The 2504, 15977, or 14760 nucleotide sequences or portions thereof can be used to map the location of the 2504, 15977, or 14760 genes on a chromosome. This process is called chromosome mapping. Chromosome mapping is useful in correlating the 2504, 15977, or 14760 sequences with genes associated with disease.

Briefly, 2504, 15977, or 14760 genes can be mapped to chromosomes by preparing PCR primers (preferably 15–25 bp in length) from the 2504, 15977, or 14760 nucleotide sequences. These primers can then be used for PCR screening of somatic cell hybrids containing individual human chromosomes. Only those hybrids containing the human gene corresponding to the 2504, 15977, or 14760 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 2504, 15977, or 14760 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the 2504, 15977, or 14760 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 2504, 15977, or 14760 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 2504, 15977, or 14760 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 2504, 15977, or 14760 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 2504, 15977, or 14760 Sequences in Forensic Biology

DNA-based identification techniques can also be used in forensic biology, To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:4, or SEQ ID NO:7 (e.g., fragments derived from the noncoding regions of SEQ ID NO:1, SEQ ID NO:4, or SEQ ID NO:7 having a length of at least 20 bases, preferably at least 30 bases) are particularly appropriate for this use.

The 2504, 15977, or 14760 nucleotide sequences described herein can further be used to provide polynucleotide reagents, e.g., labeled or labelable probes which can be used in, for example, an in situ hybridization technique, to identify a specific tissue, e.g., a tissue containing protein kinase activity. This can be very useful in cases where a forensic pathologist is presented with a tissue of unknown origin. Panels of such 2504, 15977, or 14760 probes can be used to identify tissue by species and/or by organ type.

In a similar fashion, these reagents, e.g., 2504, 15977, or 14760 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 2504, 15977, or 14760.

Such disorders include, e.g., a disorder associated with the misexpression of 2504, 15977, or 14760, or a cellular growth related disorder.

The method includes one or more of the following:

detecting, in a tissue of the subject, the presence or absence of a mutation which affects the expression of the 2504, 15977, or 14760 gene, or detecting the presence or absence of a mutation in a region which controls the expression of the gene, e.g., a mutation in the 5' control region;

detecting, in a tissue of the subject, the presence or absence of a mutation which alters the structure of the 2504, 15977, or 14760 gene;

detecting, in a tissue of the subject, the misexpression of the 2504, 15977, or 14760 gene, at the mRNA level, e.g., detecting a non-wild type level of a mRNA;

detecting, in a tissue of the subject, the misexpression of the gene, at the protein level, e.g., detecting a non-wild type level of a 2504, 15977, or 14760 polypeptide.

In preferred embodiments the method includes: ascertaining the existence of at least one of: a deletion of one or more nucleotides from the 2504, 15977, or 14760 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, SEQ ID NO:4, SEQ ID NO:7, or naturally occurring mutants thereof or 5' or 3' flanking sequences naturally associated with the 2504, 15977, or 14760 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 2504, 15977, or 14760 gene; the presence of a non-wild type splicing pattern of a messenger RNA transcript of the gene; or a non-wild type level of 2504, 15977, or 14760.

Methods of the invention can be used prenatally or to determine if a subject's offspring will be at risk for a disorder.

In preferred embodiments the method includes determining the structure of a 2504, 15977, or 14760 gene, an abnormal structure being indicative of risk for the disorder.

In preferred embodiments the method includes contacting a sample form the subject with an antibody to the 2504, 15977, or 14760 protein or a nucleic acid, which hybridizes specifically with the gene. There and other embodiments are discussed below, Diagnostic and Prognostic Assays Diagnostic and prognostic assays of the invention include method for assessing the expression level of 2504, 15977 and 14760 molecules and for identifying variations and mutations in the sequence of 2504, 15977 and 14760 molecules.

Expression Monitoring and Profiling

The presence, level, or absence of a 2504, 15977 or 14760 protein or nucleic acid in a biological sample can be evaluated by obtaining a biological sample from a test subject and contacting the biological sample with a compound or an agent capable of detecting 2504, 15977 and 14760 protein or nucleic acid (e.g., mRNA, genomic DNA) that encodes 2504, 15977 and 14760 protein such that the presence of 2504, 15977 and 14760 protein or nucleic acid is detected in the biological sample. The term "biological sample" includes tissues, cells and biological fluids isolated from a subject, as well as tissues, cells and fluids present within a subject. A preferred biological sample is serum. The level of expression of the 2504, 15977 and 14760 gene can be measured in a number of ways, including, but not limited to: measuring the mRNA encoded by the 2504, 15977 and 14760 genes; measuring the amount of protein encoded by the 2504, 15977 and 14760 genes; or measuring the activity of the protein encoded by the 2504, 15977 and 14760 genes.

The level of mRNA corresponding to the 2504, 15977 and 14760 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 2504, 15977 and 14760 nucleic acid, such as the nucleic acid of SEQ ID NO:1, 4 or 7, or a portion thereof, such as an oligonucleotide of at least 7, 15, 30, 50, 100, 250 or 500 nucleotides in length and sufficient to specifically hybridize under stringent conditions to 2504, 15977 and 14760 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. The probe can be disposed on an address of an array, e.g., an array described below. A skilled artisan can adapt known mRNA detection methods for use in detecting the level of mRNA encoded by the 2504, 15977 and 14760 genes.

The level of mRNA in a sample that is encoded by one of 2504, 15977 and 14760 can be evaluated with nucleic acid amplification, e.g., by rtPCR (Mullis, 1987, U.S. Pat. No. 4,683,202), ligase chain reaction (Barany, 1991, Proc. Natl. Acad. Sci. USA 88:189–193), self sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 2504, 15977 or 14760 gene being analyzed.

In another embodiment, the methods further contacting a control sample with a compound or agent capable of detecting 2504, 15977 and 14760 mRNA, or genomic DNA, and comparing the presence of 2504, 15977 and 14760 mRNA or genomic DNA in the control sample with the presence of 2504, 15977 and 14760 mRNA or genomic DNA in the test sample.

A variety of methods can be used to determine the level of protein encoded by 2504, 15977 and 14760. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 2504, 15977 and 14760 protein in a biological sample in vitro as well as in vivo. In vitro techniques for detection of 2504, 15977 and 14760 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 2504, 15977 and 14760 protein include introducing into a subject a labeled anti-2504, 15977 and 14760 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-2504, 15977 or 14760 antibody positioned on an antibody array (as described below). The sample can be detected, e.g., with avidin coupled to a fluorescent label.

In another embodiment, the methods further include contacting the control sample with a compound or agent capable of detecting 2504, 15977 or 14760 protein, and comparing the presence of 2504, 15977 or 14760 protein in the control sample with the presence of 2504, 15977 or 14760 protein in the test sample.

The invention also includes kits for detecting the presence of 2504, 15977 and 14760 in a biological sample. For example, the kit can include a compound or agent capable of detecting 2504, 15977 or 14760 protein or mRNA in a biological sample; and a standard. The compound or agent can be packaged in a suitable container. The kit can further comprise instructions for using the kit to detect 2504, 15977 or 14760 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit, The diagnostic methods described herein can identify subjects having, or at risk of developing, a disease or disorder associated with misexpressed or aberrant or unwanted 2504, 15977 and 14760 expression or activity. As used herein, the term "unwanted" includes an unwanted phenomenon involved in a biological response such as pain or deregulated cell proliferation.

In one embodiment, a disease or disorder associated with aberrant or unwanted 2504, 15977 and 14760 expression or activity is identified. A test sample is obtained from a subject and 2504, 15977 and 14760 protein or nucleic acid (e.g., mRNA or genomic DNA) is evaluated, wherein the level, e.g., the presence or absence, of 2504, 15977 and 14760 protein or nucleic acid is diagnostic for a subject having or at risk of developing a disease or disorder associated with aberrant or unwanted 2504, 15977 and 14760 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 2504, 15977 and 14760 expression or activity. For example, such methods can be used to determine whether a subject can be effectively treated with an agent that modulates 2504, 15977 and 14760 expression or activity.

In another aspect, the invention features a computer medium having a plurality of digitally encoded data records. Each data record includes a value representing the level of expression of 2504, 15977 and 14760 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 2504, 15977 and 14760 (e.g., other genes associated with a 2504, 15977 and 14760-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 2504, 15977 and 14760 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a DISORDERA disorder in a subject wherein an increase in 2504, 15977 and 14760 expression is an indication that the subject has or is disposed to having a disorders as described herein. The method can be used to monitor a treatment for such disorders in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) Science 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 2504, 15977 and 14760 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an un-contacted cell.

In another aspect, the invention features a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 2504, 15977 or 14760 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 2504, 15977 or 14760 expression.

Arrays and Uses Thereof

In another aspect, the invention features an array that includes a substrate having a plurality of addresses. At least one address of the plurality includes a capture probe that binds specifically to a 2504, 15977 or 14760 molecule (e.g., a 2504, 15977 or 14760 nucleic acid or a 2504, 15977 or 14760 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 2504, 15977 or 14760 nucleic acid, e.g., the sense or anti-sense strand. In one preferred embodiment, a subset of addresses of the plurality of addresses has a nucleic acid capture probe for 2504, 15977 or 14760. Each address of the subset can include a capture probe that hybridizes to a different region of a 2504, 15977 and 14760 nucleic acid. In another preferred embodiment, addresses of the subset include a capture probe for a 2504, 15977 and 14760 nucleic acid. Each address of the subset is unique, overlapping, and complementary to a different variant of 2504, 15977 or 14760 (e.g., an allelic variant, or all possible hypothetical variants). The array can be used to sequence 2504, 15977 or 14760 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 2504, 15977 or 14760 polypeptide or fragment thereof. The polypeptide can be a naturally-occurring interaction partner of 2504, 15977 or 14760 polypeptide. Preferably, the polypeptide is an antibody, e.g., an antibody described herein (see "Anti-2504, 15977 and 14760 Antibodies," above), such as a monoclonal antibody or a single-chain antibody.

In another aspect, the invention features a method of analyzing the expression of 2504, 15977 or 14760. The method includes providing an array as described above; contacting the array with a sample and detecting binding of a 2504, 15977 or 14760-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 2504, 15977 or 14760. If a sufficient number of diverse samples is analyzed, clustering (e.g., hierarchical clustering, k-means clustering, Bayesian clustering and the like) can be used to identify other genes which are co-regulated with 2504, 15977 or 14760. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 2504, 15977 or 14760 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 2504, 15977 or 14760-associated disease or disorder; and processes, such as a cellular transformation associated with a 2504, 15977 or 14760-associated disease or disorder. The method can also evaluate the treatment and/or progression of a 2504, 15977 or 14760-associated disease or disorder The array is also useful for ascertaining differential expression patterns of one or more genes in normal and abnormal cells. This provides a battery of genes (e.g., including 2504, 15977 and 14760) that could serve as a molecular target for diagnosis or therapeutic intervention.

In another aspect, the invention features an array having a plurality of addresses. Each address of the plurality includes a unique polypeptide. At least one address of the plurality has disposed thereon a 2504, 15977 or 14760 polypeptide or fragment thereof. Methods of producing polypeptide arrays are described in the art, e.g., in De Wildt et al. (2000). *Nature Biotech.* 18, 989–994; Lueking et al. (1999). *Anal. Biochem.* 270, 103–111; Ge, H. (2000). *Nucleic Acids Res.* 28, e3, I-VII; MacBeath, G., and Schreiber, S. L. (2000). *Science* 289, 1760–1763; and WO 99/51773A1. In a preferred embodiment, each addresses of the plurality has disposed thereon a polypeptide at least 60, 70, 80, 85, 90, 95 or 99% identical to a 2504, 15977 or 14760 polypeptide or fragment thereof. For example, multiple variants of a 2504, 15977 and 14760 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 2504, 15977 or 14760 binding compound, e.g., an antibody in a sample from a subject with specificity for a 2504, 15977 and 14760 polypeptide or the presence of a 2504, 15977 or 14760-binding protein or ligand.

The array is also useful for ascertaining the effect of the expression of a gene on the expression of other genes in the same cell or in different cells (e.g., ascertaining the effect of 2504, 15977 or 14760 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 2504, 15977 or 14760 or from a cell or subject in which a 2504, 15977 or 14760 mediated response has been elicited, e.g., by contact of the cell with 2504, 15977 or 14760 nucleic acid or protein, or administration to the cell or subject 2504, 15977 or 14760 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 2504, 15977 or 14760 (or does not express as highly as in the case of the 2504, 15977 or 14760 positive plurality of capture probes) or from a cell or subject which in which a 2504, 15977 or 14760 mediated response has not been elicited (or has been elicited to a lesser extent than in the first sample); contacting the array with one or more inquiry probes (which is preferably other than a 2504, 15977 or 14760 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody, In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 2504, 15977 or 14760 or from a cell or subject in which a 2504, 15977 or 14760-mediated response has been elicited, e.g., by contact of the cell with 2504, 15977 or 14760 nucleic acid or protein, or administration to the cell or subject 2504, 15977 or 14760 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 2504, 15977 or 14760 (or does not express as highly as in the case of the 2504, 15977 or 14760 positive plurality of capture probes) or from a cell or subject which in which a 2504, 15977 or 14760 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 2504, 15977 or 14760, e.g., analyzing structure, function, or relatedness to other nucleic acid or amino acid sequences. The method includes: providing a 2504, 15977 or 14760 nucleic acid or amino acid sequence; comparing the 2504, 15977 or 14760 sequence with one or more preferably a plurality of sequences from a collection of sequences, e.g., a nucleic acid or protein sequence database; to thereby analyze 2504, 15977 or 14760.

Detection of Variations or Mutations

The methods of the invention can also be used to detect genetic alterations in a 2504, 15977 or 14760 gene, thereby determining if a subject with the altered gene is at risk for a disorder characterized by mis-regulation in 2504, 15977 or 14760 protein activity or nucleic acid expression, such as an immune disorder, a neurodegenerative disorder, or a cardiovascular disorder. In preferred embodiments, the methods include detecting, in a sample from the subject, the presence or absence of a genetic alteration characterized by at least one of an alteration affecting the integrity of a gene encoding a 2504, 15977 or 14760-protein, or the mis-expression of the 2504, 15977 or 14760 gene. For example, such genetic alterations can be detected by ascertaining the existence of at least one of 1) a deletion of one or more nucleotides from a 2504, 15977 or 14760 gene; 2) an addition of one or more nucleotides to a 2504, 15977 or 14760 gene; 3) a substitution of one or more nucleotides of a 2504, 15977 or 14760 gene, 4) a chromosomal rearrangement of a 2504, 15977 or 14760 gene; 5) an alteration in the level of a messenger RNA transcript of a 2504, 15977 or 14760 gene, 6) aberrant modification of a 2504, 15977 or 14760 gene, such as of the methylation pattern of the genomic DNA, 7) the presence of a non-wild type splicing pattern of a messenger RNA transcript of a 2504, 15977 or 14760 gene, 8) a non-wild type level of a 2504, 15977 or 14760-protein, 9) allelic loss of a 2504, 15977 or 14760 gene, and 10) inappropriate post-translational modification of a 2504, 15977 or 14760-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 2504, 15977 or 14760-gene. This method can include the steps of collecting a sample of cells from a subject, isolating nucleic acid (e.g., genomic, mRNA or both) from the sample, contacting the nucleic acid sample with one or more primers which specifically hybridize to a 2504, 15977 or 14760 gene under conditions such that hybridization and amplification of the 2504, 15977 or 14760-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or other nucleic acid amplification methods, followed by the detection of the amplified molecules using techniques known to those of skill in the art.

In another embodiment, mutations in a 2504, 15977 or 14760 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 2504, 15977 or 14760 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) *Human Mutation* 7:244–255; Kozal, M. J. et al. (1996) *Nature Medicine* 2: 753–759). For example, genetic mutations in 2504, 15977 and 14760 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 2504, 15977 or 14760 gene and detect mutations by comparing the sequence of the sample 2504, 15977 or 14760 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 2504, 15977 or 14760 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 2504, 15977 and 14760 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 2504, 15977 or 14760 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 2504, 15977 and 14760 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 2504, 15977 or 14760 nucleic acid.

In a preferred embodiment the set includes a first and a second oligonucleotide. The first and second oligonucleotide can hybridize to the same or to different locations of SEQ ID NO:1, 3, 4, 6, 7 or 9, or the complement of SEQ ID NO:1, 3, 4, 6, 7 or 9. Different locations can be different but overlapping or or nonoverlapping on the same strand. The first and second oligonucleotide can hybridize to sites on the same or on different strands.

The set can be useful, e.g., for identifying SNP's, or identifying specific alleles of 2504, 15977 or 14760. In a preferred embodiment, each oligonucleotide of the set has a different nucleotide at an interrogation position. In one embodiment, the set includes two oligonucleotides, each complementary to a different allele at a locus, e.g., a biallelic or polymorphic, locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 2504, 15977 or 14760 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 2504, 15977 or 14760 gene.

Use of 2504, 15977 and 14760 Molecules as Surrogate Markers

The 2504, 15977 and 14760 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 2504, 15977 and 14760 molecules of the invention may be detected, and may be correlated with one or more biological states in vivo. For example, the 2504, 15977 and 14760 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 2504, 15977 and 14760 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 2504, 15977 or 14760 marker) transcription or expression, the amplified marker may be in a quantity which is more readily detectable than the drug itself. Also, the marker may be more easily detected due to the nature of the marker itself; for example, using the methods described herein, anti-2504, 15977 or 14760 antibodies may be employed in an immune-based detection system for a 2504, 15977 and 14760 protein marker, or 2504, 15977 and 14760-specific radiolabeled probes may be used to detect a 2504, 15977 or 14760 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21-S24; and Nicolau (I999) *Am, J. Health-Syst. Pharm.* 56 Suppl. 3: S16-S20.

The 2504, 15977 or 14760 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 2504, 15977 or 14760 protein or RNA) for specific tumor markers in a subject, a drug or course of treatment may be selected that is optimized for the treatment of the specific tumor likely to be present in the subject. Similarly, the presence or absence of a specific sequence mutation in 2504, 15977 or 14760 DNA may correlate 2504, 15977 or 14760 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-2504, 15977, or 14760 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indeces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 2504, 15977, or 14760 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 2504, 15977, or 14760 molecules of the present invention or 2504, 15977, or 14760 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 2504, 15977, or 14760 expression or activity, by administering to the subject a 2504, 15977, or 14760 or an agent which modulates 2504, 15977, or 14760 expression or at least one 2504, 15977, or 14760 activity. Subjects at risk for a disease which is caused or contributed to by aberrant or unwanted 2504, 15977, or 14760 expression or activity can be identified by, for example, any or a combination of diagnostic or prognostic assays as described herein. Administration of a prophylactic agent can occur prior to the manifestation of symptoms characteristic of the 2504, 15977, or 14760 aberrance, such that a disease or disorder is prevented or, alternatively, delayed in its progression. Depending on the type of 2504, 15977, or 14760 aberrance, for example, a 2504, 15977, or 14760, 2504, 15977, or 14760 agonist or 2504, 15977, or 14760 antagonist agent can be used for treating the subject. The appropriate agent can be determined based on screening assays described herein.

It is possible that some 2504, 15977, or 14760 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 2504, 15977, or 14760 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 2504, 15977, or 14760 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 2504, 15977, or 14760 expression is through the use of aptamer molecules specific for 2504, 15977, or 14760 protein. Aptamers are nucleic acid molecules having a tertiary structure which permits them to specifically bind to protein ligands (see, e.g., Osborne, et al. Curr. Opin. Chem Biol. 1997, 1(1): 5–9; and Patel, D. J. Curr Opin Chem Biol 1997 June;1(1):32–46). Since nucleic acid molecules may in many cases be more conveniently introduced into target cells than therapeutic protein molecules may be, aptamers offer a method by which 2504, 15977, or 14760 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 2504, 15977, or 14760 disorders. For a description of antibodies, see the Antibody section above.

In circumstances wherein injection of an animal or a human subject with a 2504, 15977, or 14760 protein or epitope for stimulating antibody production is harmful to the subject, it is possible to generate an immune response against 2504, 15977, or 14760 through the use of anti-idiotypic antibodies (see, for example, Herlyn, D. Ann Med 1999;31(1):66–78; and Bhattacharya-Chatterjee, M., and Foon, K. A. Cancer Treat Res 1998;94:51–68). If an anti-idiotypic antibody is introduced into a mammal or human subject, it should stimulate the production of anti-anti-idiotypic antibodies, which should be specific to the 2504, 15977, or 14760 protein. Vaccines directed to a disease characterized by 2504, 15977, or 14760 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993, *Proc. Natl. Acad. Sci. USA* 90:7889–7893).

The identified compounds that inhibit target gene expression, synthesis and/or activity can be administered to a patient at therapeutically effective doses to prevent, treat or ameliorate 2504, 15977, or 14760 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 2504, 15977, or 14760 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of 2504, 15977, or 14760 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142–2144.

Another aspect of the invention pertains to methods of modulating 2504, 15977, or 14760 expression or activity for therapeutic purposes. Accordingly, in an exemplary embodiment, the modulatory method of the invention involves contacting a cell with a 2504, 15977, or 14760 or agent that modulates one or more of the activities of 2504, 15977, or 14760 protein activity associated with the cell. An agent that modulates 2504, 15977, or 14760 protein activity can be an agent as described herein, such as a nucleic acid or a protein, a naturally-occurring target molecule of a 2504, 15977, or 14760 protein (e.g., a 2504, 15977, or 14760 substrate or receptor), a 2504, 15977, or 14760 antibody, a 2504, 15977, or 14760 agonist or antagonist, a peptidomimetic of a 2504, 15977, or 14760 agonist or antagonist, or other small molecule.

In one embodiment, the agent stimulates one or 2504, 15977, or 14760 activities. Examples of such stimulatory agents include active 2504, 15977, or 14760 protein and a nucleic acid molecule encoding 2504, 15977, or 14760. In another embodiment, the agent inhibits one or more 2504, 15977, or 14760 activities. Examples of such inhibitory agents include antisense 2504, 15977, or 14760 nucleic acid molecules, anti2504, 15977, or 14760 antibodies, and 2504, 15977, or 14760 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 2504, 15977, or 14760 protein or nucleic acid molecule. In one embodiment, the method involves administering an agent (e.g., an agent identified by a screening assay described herein), or combination of agents that modulates (e.g., upregulates or downregulates) 2504, 15977, or 14760 expression or activity. In another embodiment, the method involves administering a 2504, 15977, or 14760 protein or nucleic acid molecule as therapy to compensate for reduced, aberrant, or unwanted 2504, 15977, or 14760 expression or activity.

Stimulation of 2504, 15977, or 14760 activity is desirable in situations in which 2504, 15977, or 14760 is abnormally downregulated and/or in which increased 2504, 15977, or 14760 activity is likely to have a beneficial effect. For example, stimulation of 2504, 15977, or 14760 activity is desirable in situations in which a 2504, 15977, or 14760 is downregulated and/or in which increased 2504, 15977, or 14760 activity is likely to have a beneficial effect. Likewise, inhibition of 2504, 15977, or 14760 activity is desirable in situations in which 2504, 15977, or 14760 is abnormally upregulated and/or in which decreased 2504, 15977, or 14760 activity is likely to have a beneficial effect.

Pharmacogenomics

The 2504, 15977, or 14760 molecules of the present invention, as well as agents, or modulators which have a stimulatory or inhibitory effect on 2504, 15977, or 14760 activity (e.g., 2504, 15977, or 14760 gene expression) as identified by a screening assay described herein can be administered to individuals to treat (prophylactically or therapeutically) 2504, 15977, or 14760 associated disorders (e.g., cellular growth related disorders) associated with aberrant or unwanted 2504, 15977, or 14760 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 2504, 15977, or 14760 molecule or 2504, 15977, or 14760 modulator as well as tailoring the dosage and/or therapeutic regimen of treatment with a 2504, 15977, or 14760 molecule or 2504, 15977, or 14760 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 2504, 15977, or 14760 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 2504, 15977, or 14760 molecule or 2504, 15977, or 14760 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 2504, 15977, or 14760 molecule or 2504, 15977, or 14760 modulator, such as a modulator identified by one of the exemplary screening assays described herein.

The present invention further provides methods for identifying new agents, or combinations, that are based on identifying agents that modulate the activity of one or more of the gene products encoded by one or more of the 2504, 15977, or 14760 genes of the present invention, wherein these products may be associated with resistance of the cells to a therapeutic agent. Specifically, the activity of the proteins encoded by the 2504, 15977, or 14760 genes of the present invention can be used as a basis for identifying agents for overcoming agent resistance. By blocking the activity of one or more of the resistance proteins, target cells, e.g., cancer cells, will become sensitive to treatment with an agent that the unmodified target cells were resistant to.

Monitoring the influence of agents (e.g., drugs) on the expression or activity of a 2504, 15977, or 14760 protein can be applied in clinical trials. For example, the effectiveness of an agent determined by a screening assay as described herein to increase 2504, 15977, or 14760 gene expression, protein levels, or upregulate 2504, 15977, or 14760 activity, can be monitored in clinical trials of subjects exhibiting decreased 2504, 15977, or 14760 gene expression, protein levels, or downregulated 2504, 15977, or 14760 activity. Alternatively, the effectiveness of an agent determined by a screening assay to decrease 2504, 15977, or 14760 gene expression, protein levels, or downregulate 2504, 15977, or 14760 activity, can be monitored in clinical trials of subjects exhibiting increased 2504, 15977, or 14760 gene expression, protein levels, or upregulated 2504, 15977, or 14760 activity. In such clinical trials, the expression or activity of a 2504, 15977, or 14760 gene, and preferably, other genes that have been implicated in, for example, a 2504, 15977, or 14760-associated disorder can be used as a "read out" or markers of the phenotype of a particular cell.

Informatics

The sequence of a 2504, 15977 or 14760 molecule is provided in a variety of media to facilitate use thereof. A sequence can be provided as a manufacture, other than an isolated nucleic acid or amino acid molecule, which contains a 2504, 15977 or 14760. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 2504, 15977 or 14760 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device. As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network).

Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 2504, 15977 or 14760, e.g., analyzing structure, function, or relatedness to one or more other nucleic acid or amino acid sequences. The method includes: providing a 2504, 15977 or 14760 nucleic acid or amino acid sequence; comparing the 2504, 15977 or 14760 sequence with a second sequence, e.g., one or more preferably a plurality of sequences from a collection of sequences, e.g., a nucleic acid or protein sequence database to thereby analyze 2504, 15977 or 14760. The method can be performed in a machine, e.g., a computer, or manually by a skilled artisan.

The method can include evaluating the sequence identity between a 2504, 15977 or 14760 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 2504, 15977 or 14760 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 2504, 15977 or 14760 sequence, or record, in machine-readable form; comparing a second sequence to the 2504, 15977 or 14760 sequence; thereby analyzing a sequence. Comparison can include comparing to sequences for sequence identity or determining if one sequence is included within the other, e.g., determining if the 2504, 15977 or 14760 sequence includes a sequence being compared. In a preferred embodiment the 2504, 15977 or 14760 or second sequence is stored on a first computer, e.g., at a first site and the comparison is performed, read, or recorded on a second computer, e.g., at a second site. E.g., the 2504, 15977 or 14760 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof, the 5' end of the translated region.

In another aspect, the invention provides a machine-readable medium for holding instructions for performing a method for determining whether a subject has a 2504, 15977 or 14760-associated disease or disorder or a pre-disposition to a 2504, 15977 or 14760-associated disease or disorder, wherein the method comprises the steps of determining 2504, 15977 or 14760 sequence information associated with the subject and based on the 2504, 15977 or 14760 sequence information, determining whether the subject has a 2504, 15977 or 14760-associated disease or disorder or a pre-disposition to a 2504, 15977 or 14760-associated disease or disorder and/or recommending a particular treatment for the disease, disorder or pre-disease condition.

The invention further provides in an electronic system and/or in a network, a method for determining whether a subject has a 2504, 15977 or 14760-associated disease or disorder or a pre-disposition to a disease associated with a 2504, 15977 or 14760 wherein the method comprises the steps of determining 2504, 15977 or 14760 sequence information associated with the subject, and based on the 2504, 15977 or 14760 sequence information, determining whether the subject has a 2504, 15977 or 14760-associated disease or disorder or a pre-disposition to a 2504, 15977 or 14760-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 2504, 15977 or 14760 sequence of the subject to the 2504, 15977 or 14760 sequences in the database to thereby determine whether the subject as a 2504, 15977 or 14760-associated disease or disorder, or a pre-disposition for such.

The present invention also provides in a network, a method for determining whether a subject has a 2504, 15977 or 14760 associated disease or disorder or a pre-disposition to a 2504, 15977 or 14760-associated disease or disorder associated with 2504, 15977 or 14760, said method comprising the steps of receiving 2504, 15977 or 14760 sequence information from the subject and/or information related thereto, receiving phenotypic information associated with the subject, acquiring information from the network corresponding to 2504, 15977 or 14760 and/or corresponding to a 2504, 15977 or 14760-associated disease or disorder (e.g., a 2504, 15977 or 14760-mediated disorder as described herein), and based on one or more of the phenotypic information, the 2504, 15977 or 14760 information (e.g., sequence information and/or information related thereto), and the acquired information, determining whether the subject has a 2504, 15977 or 14760-associated disease or disorder or a pre-disposition to a 2504, 15977 or 14760-associated disease or disorder. The method may further comprise the step of recommending a particular treatment for the disease, disorder or pre-disease condition.

The present invention also provides a method for determining whether a subject has a 2504, 15977 or 14760-associated disease or disorder or a pre-disposition to a 2504, 15977 or 14760-associated disease or disorder, said method comprising the steps of receiving information related to 2504, 15977 or 14760 (e.g., sequence information and/or information related thereto), receiving phenotypic information associated with the subject, acquiring information from the network related to 2504, 15977 or 14760 and/or related to a 2504, 15977 or 14760-associated disease or disorder, and based on one or more of the phenotypic information, the 2504, 15977 or 14760 information, and the acquired information, determining whether the subject has a 2504, 15977 or 14760-associated disease or disorder or a pre-disposition to a 2504, 15977 or 14760-associated disease or disorder. The method may further comprise the step of recommending a particular treatment for the disease, disorder or pre-disease condition.

This invention is further illustrated by the following examples which should not be construed as limiting. The contents of all references, patents and published patent applications cited throughout this application are incorporated herein by reference.

EXAMPLES

Example 1
Identification and Characterization of Human 2504, 15977, or 14760 cDNA and Genomic Sequence The human 2504 sequence (FIG. 1A–B; SEQ ID NO:1), which is approximately 2297 nucleotides long including untranslated regions, contains a predicted methionine-initiated coding sequence of about 1503 nucleotides (nucleotides 154–1656 of SEQ ID NO:1; SEQ ID NO:3). The coding sequence encodes a 501 amino acid protein (SEQ ID NO:2).

The human 15977 sequence (FIG. 4A–C; SEQ ID NO:4), which is approximately 4417 nucleotides long including untranslated regions, contains a predicted methionine-initiated coding sequence of about 1377 nucleotides (nucleotides 337–1713 of SEQ ID NO:4; SEQ ID NO:6). The coding sequence encodes a 459 amino acid protein (SEQ ID NO:5).

The human 14760 sequence (FIG. 7A–B; SEQ ID NO:7), which is approximately 2046 nucleotides long including untranslated regions, contains a predicted methionine-initiated coding sequence of about 1788 nucleotides (nucleotides 119–1906 of SEQ ID NO:7; SEQ ID NO:9). The coding sequence encodes a 596 amino acid protein (SEQ ID NO:8).

Example 2
Tissue Distribution of 2504, 15977, or 14760 mRNA

Endogenous human 2504, 15977, and 14760 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Samples can be internally controlled by the addition of a second set of primers/probe specific for a housekeeping gene such as GAPDH which has been labeled with a different fluorophore on the 5' end (typically VIC).

To determine the level of 2504, 15977, and 14760 in various human tissues a primer/probe set was designed using Primer Express (Perkin-Elmer) software and primary cDNA sequence information. Total RNA was prepared from a series of human tissues using an RNeasy kit from Qiagen. First strand cDNA was prepared from 1 µg total RNA using an oligo-dT primer and Superscript II reverse transcriptase (Gibco/BRL). cDNA obtained from approximately 50 ng total RNA was used per TaqMan reaction. 2504, 15977, and 14760 mRNA levels were analyzed in a variety of samples of human tissues Northern blot hybridizations with various RNA samples can be performed under standard conditions and washed under stringent conditions, i.e., 0.2×SSC at 65° C. A DNA probe corresponding to all or a portion of the 2504, 15977, or 14760 cDNA (SEQ ID NO:1) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 3

Recombinant Expression of 2504, 15977, or 14760 in Bacterial Cells

In this example, 2504, 15977, or 14760 is expressed as a recombinant glutathione-S-transferase (GST) fusion polypeptide in E. coli and the fusion polypeptide is isolated and characterized. Specifically, 2504, 15977, or 14760 is fused to GST and this fusion polypeptide is expressed in E. coli, e.g., strain PEB 199. Expression of the GST-2504, 15977, or 14760 fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 2504, 15977, or 14760 Protein in COS Cells

To express the 2504, 15977, or 14760 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 2504, 15977, or 14760 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 2504, 15977, or 14760 DNA sequence is amplified by PCR using two primers. The 5' primer contains the restriction site of interest followed by approximately twenty nucleotides of the 2504, 15977, or 14760 coding sequence starting from the initiation codon; the 3' end sequence contains complementary sequences to the other restriction site of interest, a translation stop codon, the HA tag or FLAG tag and the last 20 nucleotides of the 2504, 15977, or 14760 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 2504, 15977, or 14760 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 2504, 15977, or 14760-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the 2504, 15977, or 14760 polypeptide is detected by radiolabelling ($^{35}$S-methionine or $^{35}$S-cysteine available from NEN, Boston, Mass., can be used) and immunoprecipitation (Harlow, E. and Lane, D. Antibodies. A Laboratory Manual, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 2504, 15977, or 14760 coding sequence is cloned directly into the polylinker of the pCDNA/Amp vector using the appropriate restriction sites. The resulting plasmid is transfected into COS cells in the manner described above, and the expression of the 2504, 15977, or 14760 polypeptide is detected by radiolabelling and immunoprecipitation using a 2504, 15977, or 14760 specific monoclonal antibody. Equivalents Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound which binds to a polypeptide comprising the amino acid sequence of SEQ ID NO:5, comprising the steps of:
   a) contacting the polypeptide, or a cell expressing the polypeptide with a test compound under conditions suitable for binding; and
   b) determining whether the polypeptide binds to the test compound.

2. The method of claim 1, wherein the binding of the test compound to the polypeptide is detected by a method selected from the group consisting of:
   a) direct detecting of test compound/polypeptide binding;
   b) a competition binding assay;
   c) an immunoassay;
   d) a yeast two-hybrid assay; and
   e) a protein kinase assay.

3. A method for identifying a compound which modulates the activity of a polypeptide comprising the amino acid sequence of SEQ ID NO:5, comprising:
   a) contacting the polypeptide, or a cell expressing the polypeptide with a test compound under conditions suitable for binding; and
   b) determining the effect of the test compound on the activity of the polypeptide to thereby identify a compound which modulates the activity of the polypeptide.

4. A method for identifying an agent which modulates the activity or expression of a polypeptide comprising the amino acid sequence of SEQ ID NO:5 or a nucleic acid sequence encoding the amino acid sequence of SEQ ID NO:5, comprising contacting the polypeptide or the nucleic acid with a test agent; and determining the effect of the test agent on the activity or expression of the polypeptide or nucleic acid.

5. The method of claim 4, wherein the activity is proliferation, differentiation, or survival of a cell expressing a polypeptide comprising the amino acid sequence of SEQ ID NO:5 or a nucleic acid sequence encoding the amino acid sequence of SEQ ID NO:5.

6. The method of claim 5, wherein the cell is selected from the group consisting of an epithelial cell, a cardiovascular cell, a hematopoietic cell, a skeletal muscle cell, and a neural cell.

* * * * *